(12) United States Patent
Zappacosta et al.

(10) Patent No.: US 12,396,763 B2
(45) Date of Patent: Aug. 26, 2025

(54) SPINOUS PROCESS FIXATION SYSTEM AND METHODS THEREOF

(71) Applicant: GLOBUS MEDICAL, INC., Audubon, PA (US)

(72) Inventors: Jason Zappacosta, Philadelphia, PA (US); Darren Clutter, Barto, PA (US); Robert Rightler, Pennsburg, PA (US)

(73) Assignee: Globus Medical, Inc., Audubon, PA (US)

( * ) Notice: Subject to any disclaimer, the term of this patent is extended or adjusted under 35 U.S.C. 154(b) by 90 days.

(21) Appl. No.: 18/449,781

(22) Filed: Aug. 15, 2023

(65) Prior Publication Data

US 2023/0380870 A1    Nov. 30, 2023

Related U.S. Application Data

(60) Continuation of application No. 17/379,619, filed on Jul. 19, 2021, now Pat. No. 11,723,695, which is a continuation of application No. 16/258,017, filed on Jan. 25, 2019, now Pat. No. 11,065,040, which is a continuation of application No. 15/268,995, filed on Sep. 19, 2016, now Pat. No. 10,226,283, which is a division of application No. 14/057,946, filed on Oct. 18, 2013, now Pat. No. 9,486,251, which is a continuation-in-part of application No. 13/799,364, filed on Mar. 13, 2013, now Pat. No. 9,198,697, which is a continuation-in-part of application No. 13/731,504, filed on Dec. 31, 2012, now Pat. No. 9,011,493.

(51) Int. Cl.
A61B 17/70  (2006.01)
A61B 17/00  (2006.01)

(52) U.S. Cl.
CPC ...... *A61B 17/7068* (2013.01); *A61B 17/7065* (2013.01); *A61B 2017/00858* (2013.01); *A61B 2017/00933* (2013.01)

(58) Field of Classification Search
None
See application file for complete search history.

(56) References Cited

U.S. PATENT DOCUMENTS 3,056,852 A    10/1962   Sachs
3,426,364 A    2/1969    Lumb
(Continued)

FOREIGN PATENT DOCUMENTS

JP    2012500057 A    1/2012
JP    2012522588 A    9/2012
(Continued)

*Primary Examiner* — Tessa M Matthews

(57) ABSTRACT

An implantable device may comprise a barrel, the barrel having an upper portion and a lower portion. The barrel may be configured to transition from a collapsed form having a first height to an expanded form having a second height and wherein the second height is greater than the first height. The implantable device may further include an actuator assembly disposed in the barrel, the actuator assembly comprising a front ramped actuator in engagement with the barrel, a rear ramped actuator in engagement with the barrel, and a central screw that extends from the rear ramped actuator through the front ramped actuator. The implantable device may further comprise a first plate and a second plate.

16 Claims, 55 Drawing Sheets

(56) References Cited

U.S. PATENT DOCUMENTS

| | | |
|---|---|---|
| 4,116,104 A | 9/1978 | Kennedy |
| 4,349,921 A | 9/1982 | Kuntz |
| 4,863,476 A | 9/1989 | Shepperd |
| 4,863,477 A | 9/1989 | Monson |
| 5,390,683 A | 2/1995 | Pisharodi |
| 5,403,316 A | 4/1995 | Ashman |
| 5,496,318 A | 3/1996 | Howland |
| 5,645,596 A | 7/1997 | Kim et al. |
| 5,665,122 A | 9/1997 | Kambin |
| 5,860,977 A | 1/1999 | Zucherman |
| 6,039,761 A | 3/2000 | Li |
| 6,045,579 A | 4/2000 | Hochshuler et al. |
| 6,068,630 A | 5/2000 | Zucherman |
| 6,080,193 A | 6/2000 | Hochshuler et al. |
| 6,099,531 A | 8/2000 | Bonutti |
| 6,126,689 A | 10/2000 | Brett |
| 6,176,882 B1 * | 1/2001 | Biedermann ............ A61F 2/447 623/17.11 |
| 6,258,125 B1 | 7/2001 | Paul et al. |
| 6,312,431 B1 | 11/2001 | Asfora |
| 6,364,883 B1 | 4/2002 | Santilli |
| 6,419,676 B1 | 7/2002 | Zucherman |
| 6,451,019 B1 | 9/2002 | Zucherman |
| 6,554,863 B2 | 4/2003 | Paul et al. |
| 6,562,074 B2 | 5/2003 | Gerbec |
| 6,576,016 B1 | 6/2003 | Hochshuler et al. |
| 6,641,614 B1 | 11/2003 | Wagner et al. |
| 6,648,917 B2 | 11/2003 | Gerbec |
| 6,652,527 B2 | 11/2003 | Zucherman |
| 6,666,891 B2 | 12/2003 | Boehm, Jr. |
| 6,692,495 B1 | 2/2004 | Zacouto |
| 6,695,842 B2 | 2/2004 | Zucherman |
| 6,706,070 B1 | 3/2004 | Wagner et al. |
| 6,752,832 B2 | 6/2004 | Neumann |
| 6,830,589 B2 | 12/2004 | Erickson |
| 6,849,093 B2 | 2/2005 | Michelson |
| 6,852,129 B2 | 2/2005 | Gerbec |
| 6,863,673 B2 | 3/2005 | Gerbec |
| 6,881,228 B2 | 4/2005 | Zdeblick |
| 7,018,415 B1 | 3/2006 | Mckay |
| 7,048,736 B2 | 5/2006 | Robinson |
| 7,201,751 B2 | 4/2007 | Zucherman |
| 7,217,291 B2 | 5/2007 | Zucherman |
| 7,282,063 B2 | 10/2007 | Cohen et al. |
| 7,335,203 B2 | 2/2008 | Winslow |
| 7,476,251 B2 | 1/2009 | Zucherman |
| 7,547,325 B2 | 6/2009 | Biedermann et al. |
| 7,621,953 B2 | 11/2009 | Braddock, Jr. |
| 7,641,693 B2 | 1/2010 | Gütlin |
| 7,682,396 B2 | 3/2010 | Beaurain |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | Mckinley |
| 7,815,683 B2 | 10/2010 | Melkent |
| 7,828,849 B2 | 11/2010 | Lim |
| 7,837,734 B2 | 11/2010 | Zucherman |
| 7,875,078 B2 | 1/2011 | Wysocki |
| 8,114,132 B2 | 2/2012 | Lyons |
| 8,206,420 B2 | 6/2012 | Patel |
| 8,357,181 B2 | 1/2013 | Lange |
| 8,382,842 B2 | 2/2013 | Greenhalgh |
| 8,435,298 B2 | 5/2013 | Weiman |
| 2002/0045945 A1 | 4/2002 | Liu |
| 2002/0091446 A1 | 7/2002 | Zucherman |
| 2003/0040746 A1 | 2/2003 | Mitchell |
| 2003/0216736 A1 | 11/2003 | Robinson |
| 2004/0049271 A1 | 3/2004 | Biedermann et al. |
| 2004/0153065 A1 | 8/2004 | Lim |
| 2005/0033432 A1 | 2/2005 | Gordon |
| 2005/0149188 A1 | 7/2005 | Cook et al. |
| 2005/0171541 A1 | 8/2005 | Boehm |
| 2005/0273171 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0058878 A1 | 3/2006 | Michelson |
| 2006/0122701 A1 | 6/2006 | Kiester |
| 2006/0129244 A1 | 6/2006 | Ensign |
| 2006/0149385 A1 | 7/2006 | Mckay |
| 2006/0195192 A1 | 8/2006 | Gordon |
| 2006/0229729 A1 | 10/2006 | Gordon |
| 2006/0247640 A1 | 11/2006 | Blackwell |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings |
| 2007/0055377 A1 | 3/2007 | Hanson |
| 2007/0162001 A1 | 7/2007 | Chin |
| 2007/0179500 A1 | 8/2007 | Chin |
| 2007/0191951 A1 | 8/2007 | Branch, Jr. |
| 2007/0233082 A1 | 10/2007 | Chin |
| 2007/0270812 A1 | 11/2007 | Peckham |
| 2007/0270840 A1 | 11/2007 | Chin |
| 2008/0021471 A1 | 1/2008 | Winslow |
| 2008/0021472 A1 | 1/2008 | Winslow |
| 2008/0021559 A1 | 1/2008 | Thramann |
| 2008/0065222 A1 | 3/2008 | Hamada |
| 2008/0140207 A1 | 6/2008 | Olmos |
| 2008/0167657 A1 | 7/2008 | Greenhalgh |
| 2008/0183204 A1 | 7/2008 | Greenhalgh |
| 2008/0183211 A1 | 7/2008 | Lamborne |
| 2008/0221692 A1 * | 9/2008 | Zucherman ........ A61B 17/7065 623/17.11 |
| 2008/0281346 A1 | 11/2008 | Greenhalgh |
| 2008/0281359 A1 | 11/2008 | Abdou |
| 2008/0288073 A1 | 11/2008 | Renganath |
| 2008/0300598 A1 | 12/2008 | Barriero et al. |
| 2008/0319549 A1 | 12/2008 | Greenhalgh |
| 2009/0024217 A1 | 1/2009 | Levy et al. |
| 2009/0125062 A1 | 5/2009 | Arnin |
| 2009/0149956 A1 | 6/2009 | Greenhalgh |
| 2009/0149959 A1 | 6/2009 | Conner |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner |
| 2009/0281628 A1 | 11/2009 | Oglaza |
| 2009/0292361 A1 | 11/2009 | Lopez |
| 2009/0299478 A1 | 12/2009 | Carls |
| 2010/0049324 A1 | 2/2010 | Valdevit |
| 2010/0070041 A1 | 3/2010 | Peterman |
| 2010/0082109 A1 | 4/2010 | Greenhalgh |
| 2010/0179657 A1 | 7/2010 | Greenhalgh |
| 2010/0185291 A1 | 7/2010 | Jimenez |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222884 A1 | 9/2010 | Greenhalgh |
| 2010/0234952 A1 | 9/2010 | Peterman |
| 2010/0249933 A1 | 9/2010 | Trieu |
| 2010/0280622 A1 | 11/2010 | Mckinley |
| 2010/0286779 A1 | 11/2010 | Thibodeau |
| 2010/0286780 A1 | 11/2010 | Dryer |
| 2010/0292796 A1 | 11/2010 | Greenhalgh |
| 2010/0305705 A1 | 12/2010 | Butler |
| 2010/0331981 A1 | 12/2010 | Mohammed |
| 2010/0331985 A1 | 12/2010 | Gordon |
| 2011/0022090 A1 | 1/2011 | Gordon |
| 2011/0035011 A1 | 2/2011 | Cain |
| 2011/0066186 A1 | 3/2011 | Boyer et al. |
| 2011/0093074 A1 | 4/2011 | Glerum |
| 2011/0144692 A1 | 6/2011 | Saladin |
| 2011/0184468 A1 | 7/2011 | Metcalf, Jr. |
| 2012/0150228 A1 | 6/2012 | Zappacosta et al. |

(56) References Cited

U.S. PATENT DOCUMENTS

2012/0265204 A1\* 10/2012 Schmierer .......... A61B 17/7062
                                                                              606/70
2013/0012996 A1    1/2013  Zamani et al.

FOREIGN PATENT DOCUMENTS

| JP | 2012228612 A | 11/2012 |
|----|--------------|---------|
| JP | 2014531921 A | 12/2014 |
| WO | 2006045094 A2 | 10/2005 |
| WO | 2006113080 A2 | 10/2006 |
| WO | 2008044057 A1 | 10/2007 |
| WO | 2011031924 A2 | 3/2011 |

\* cited by examiner

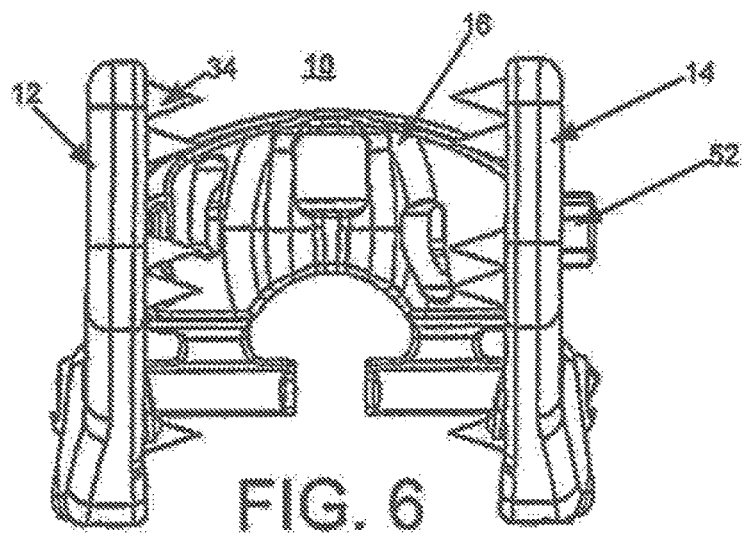
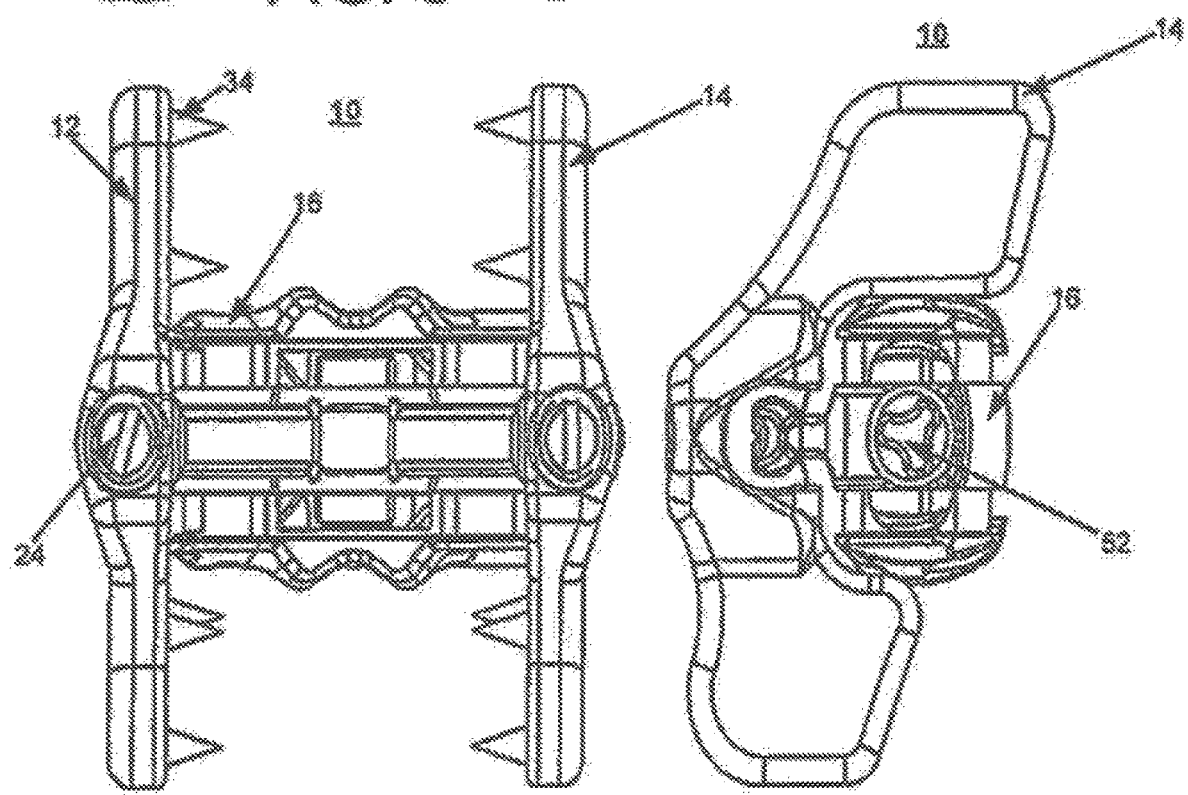
FIG. 6
FIG. 7
FIG. 8

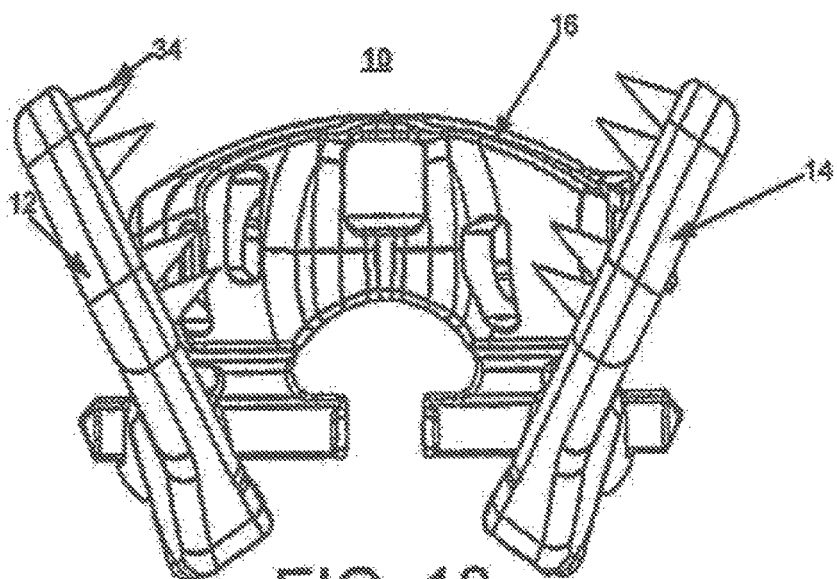
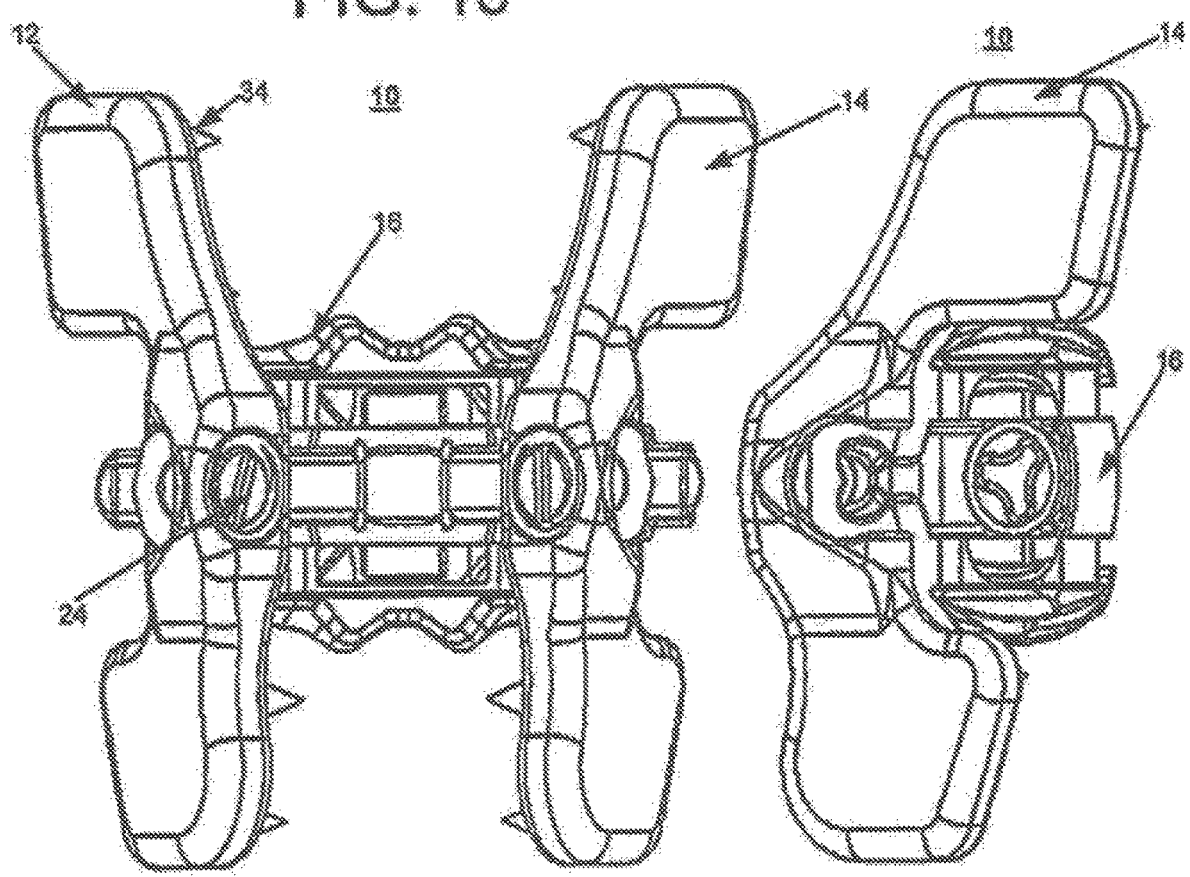
FIG. 18
FIG. 19   FIG. 20

DETAIL A
SCALE 20.000

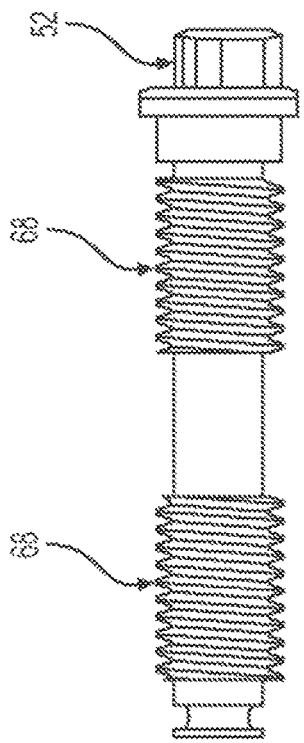
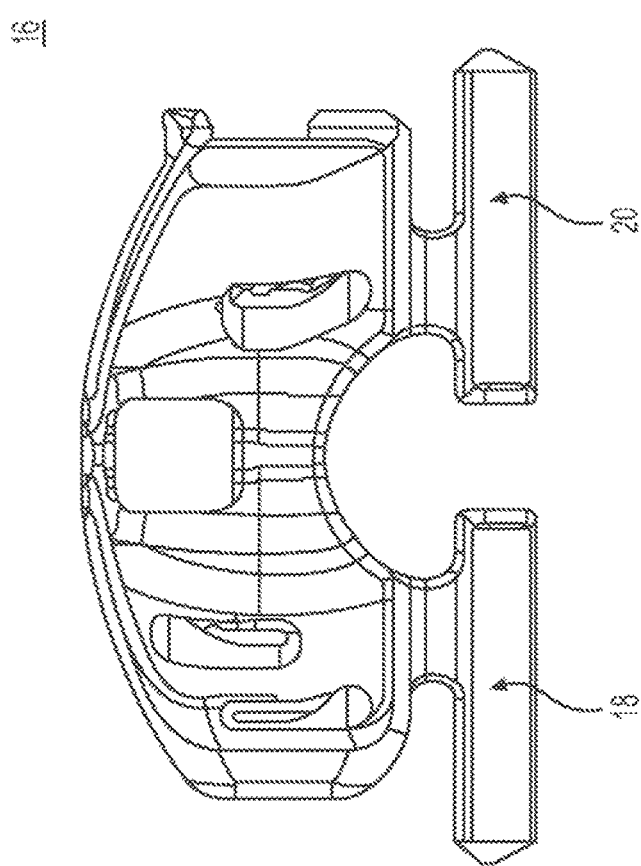
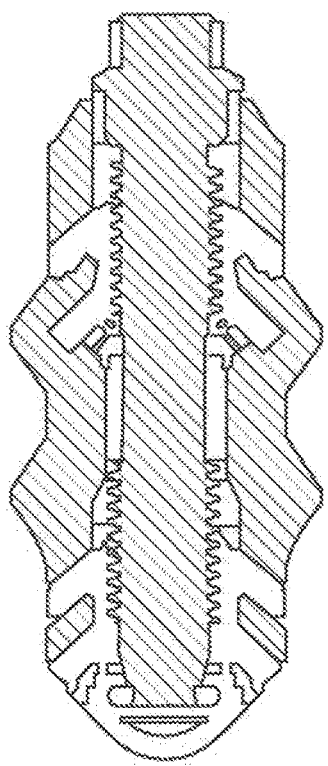
FIG. 30

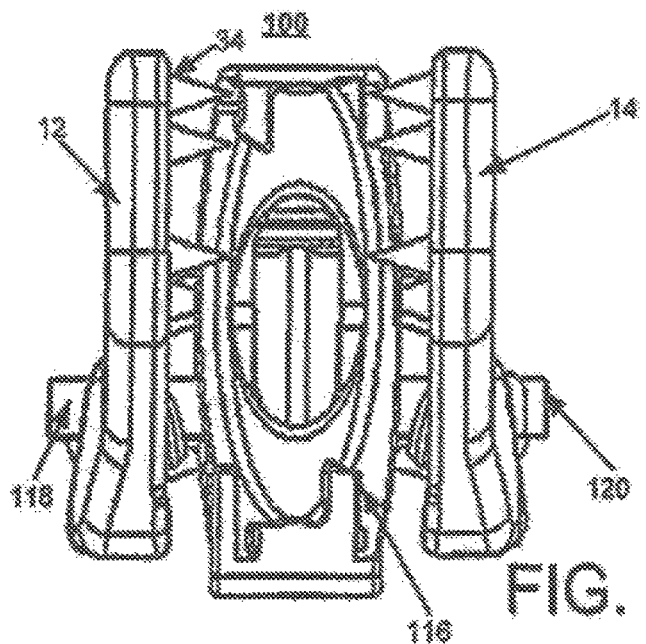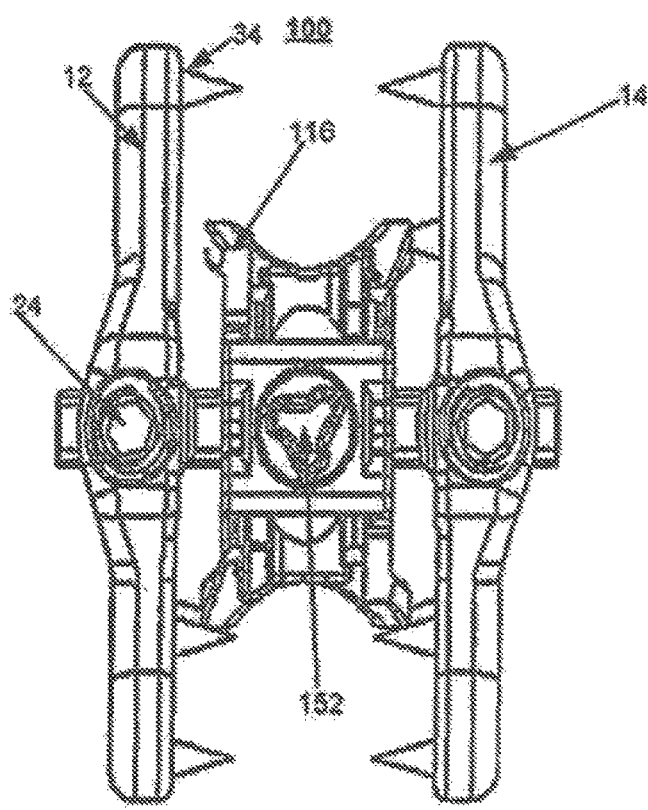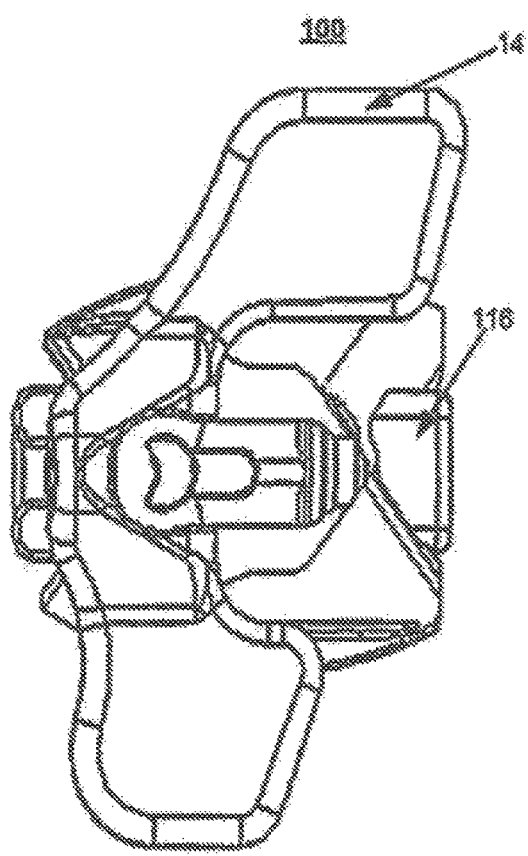
FIG. 36
FIG. 37
FIG. 38

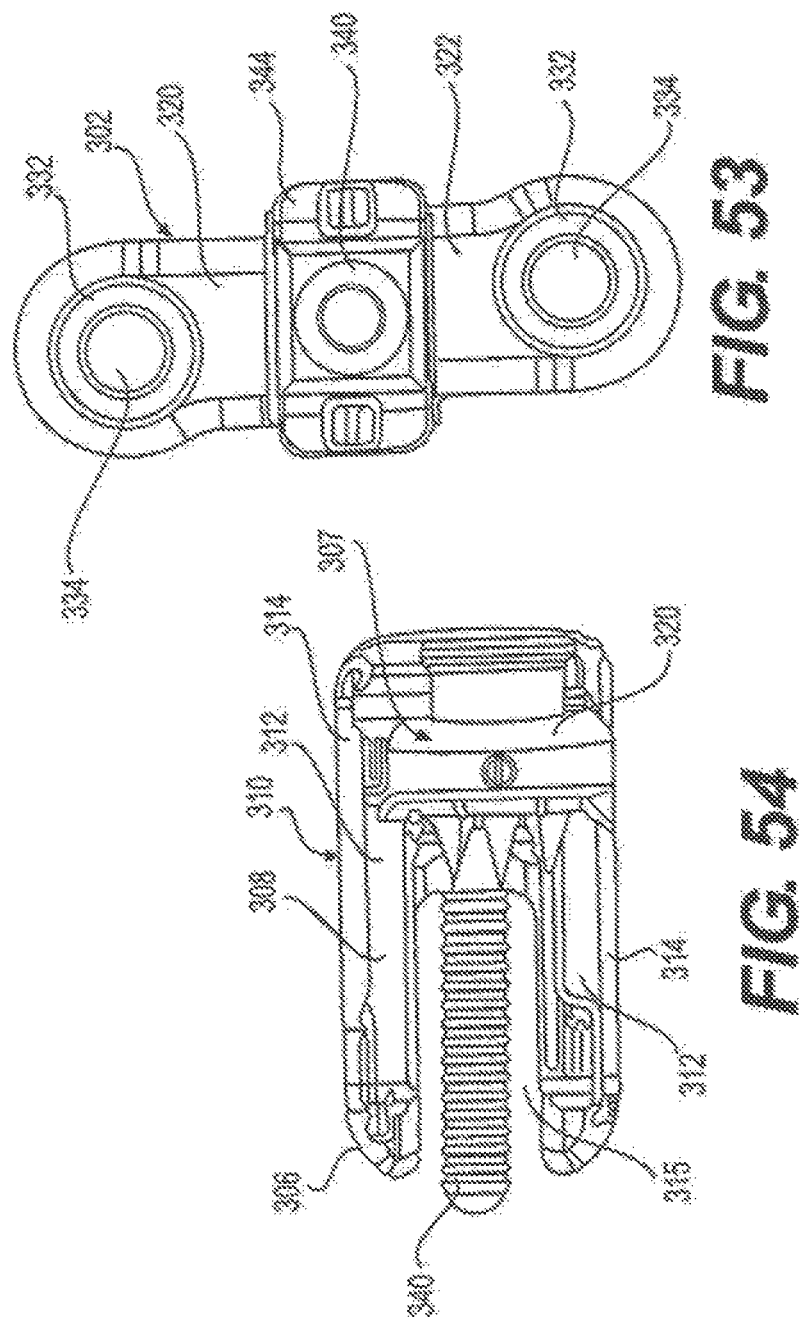

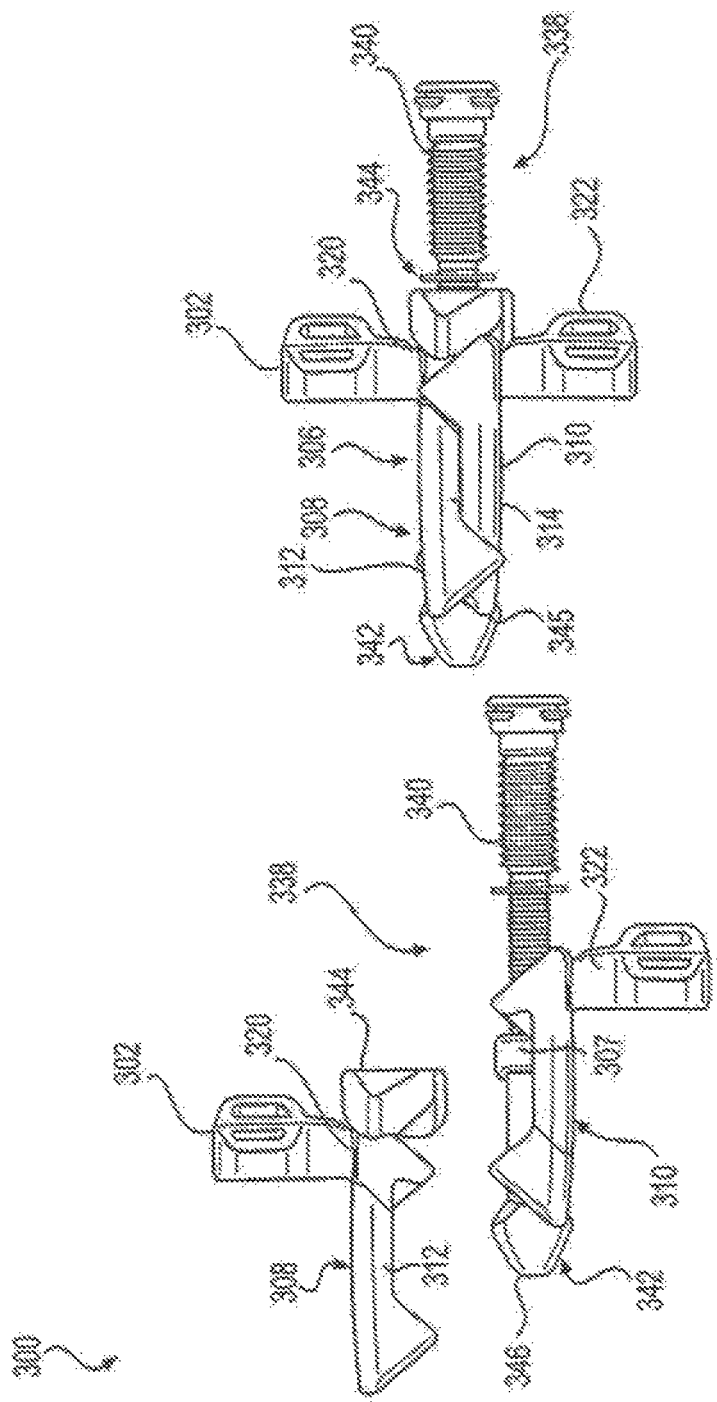

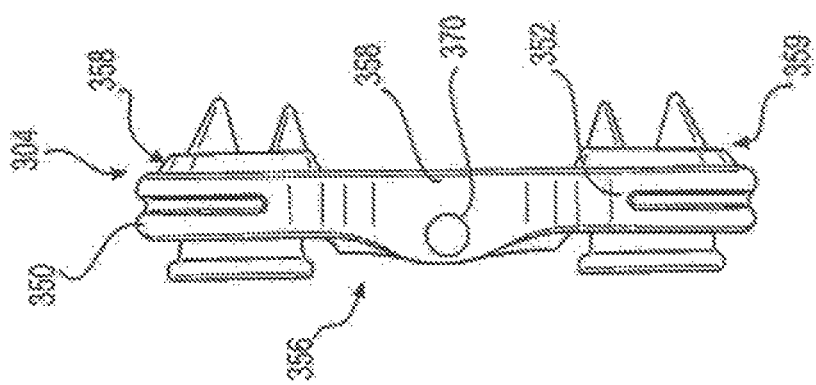

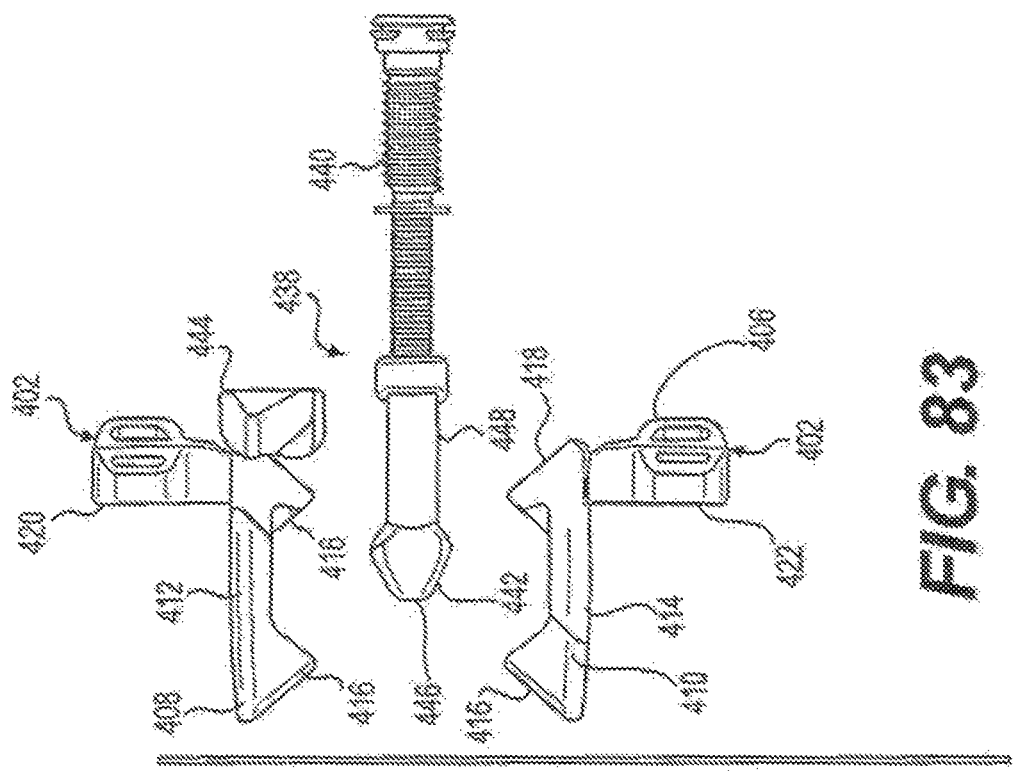
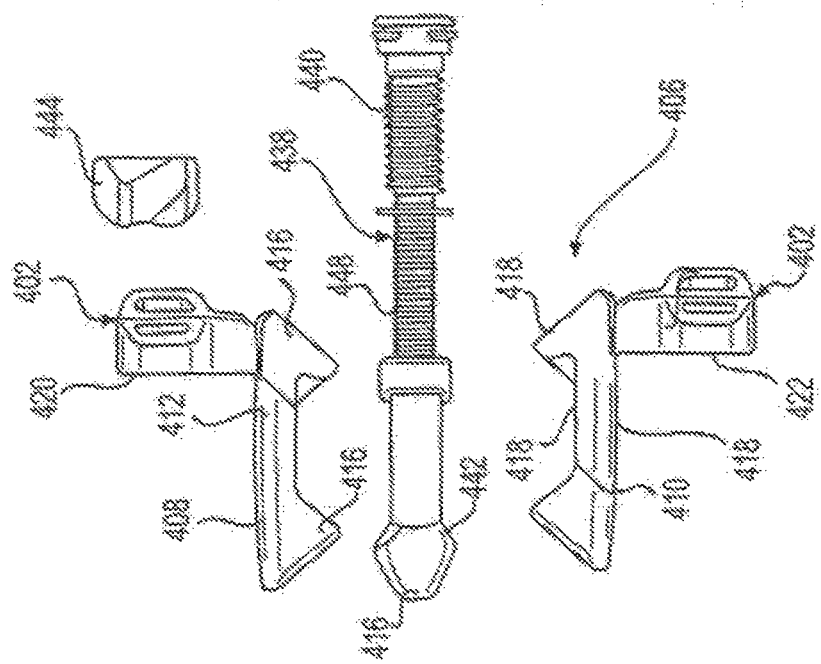

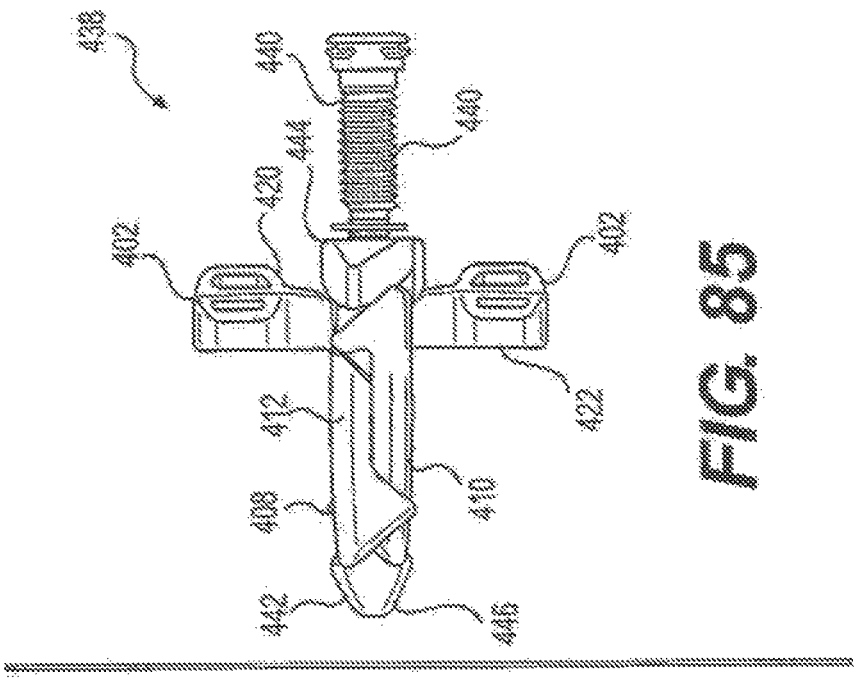
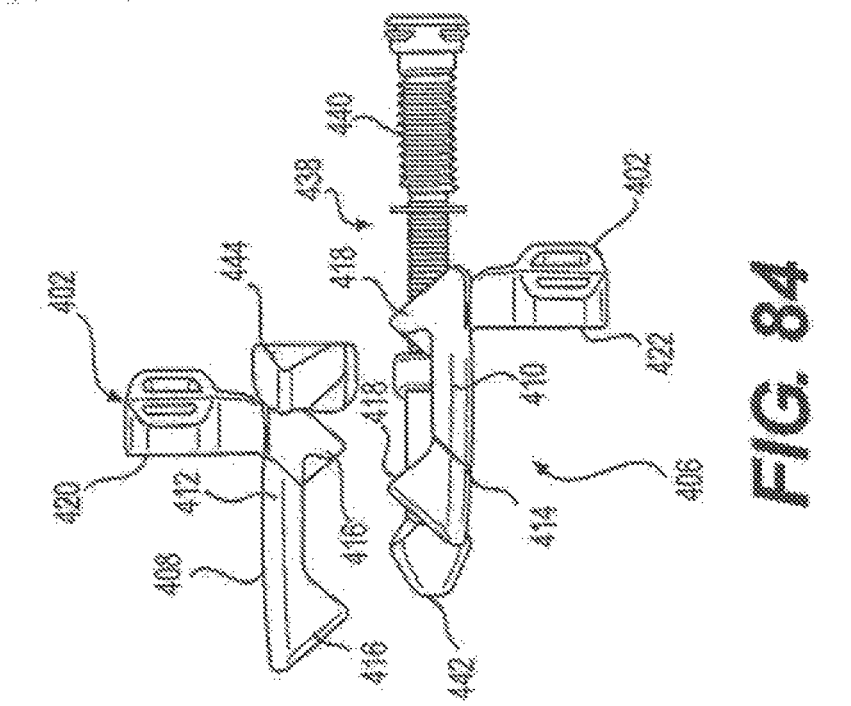

SPINOUS PROCESS FIXATION SYSTEM AND METHODS THEREOF

CROSS-REFERENCE TO RELATED APPLICATIONS

This application is a continuation of U.S. patent application Ser. No. 17/379,619, filed Jul. 19, 2021, which is a continuation of U.S. patent application Ser. No. 16/258,017, filed Jan. 25, 2019, which is a continuation of U.S. patent application Ser. No. 15/268,995, filed on Sep. 19, 2016 (published as U.S. Pat. Pub. No. 2017/0000529), which is a divisional of U.S. patent application Ser. No. 14/057,946, filed Oct. 18, 2013 (now U.S. Pat. No. 9,486,251), which is a continuation-in-part of U.S. patent application Ser. No. 13/799,364, filed Mar. 13, 2013 (now U.S. Pat. No. 9,198,697), which is a continuation-in-part of U.S. patent application Ser. No. 13/731,504, filed Dec. 31, 2012 (now U.S. Pat. No. 9,011,493), the entire disclosures of which are incorporated herein by reference for all purposes.

FIELD OF THE INVENTION

This description relates to medical devices and systems and more particularly to a spinous process fixation system and methods thereof. In particular, in one or more implementations, this description relates to spinous process fusion devices that distract and/or immobilize the spinous processes of adjacent vertebrae.

BACKGROUND

A variety of medical devices and medical device systems may be implanted within a body of a patient to provide support to a portion or portions of the patient's body. For example, some medical devices may be implanted and coupled to backbones or portions of a spine of a patient and may be configured to provide support to the spinal bone structure of the patient.

Typically, weaknesses in the spine are corrected using devices that fuse one or more vertebrae together. It may be desirable to have an implantable device that provides for structural stability to adjacent vertebrae and to achieve supplemental fusion to treat weaknesses in the spine due to degenerative disc disease, spondylolisthesis, trauma (i.e., fracture or dislocation), tumor and/or other causes.

SUMMARY

According to one general aspect, an implantable device includes a barrel. The barrel has a first portion and a second portion. The implantable device includes a first plate having multiple projections extending from one side of the first plate, where the first plate is configured to movably couple to the first portion of the barrel. The implantable device includes a second plate having multiple projections extending from one side of the second plate, where the second plate is configured to movably couple to the second portion of the barrel. The barrel is configured to transition from a collapsed form having a first height to an expanded form having a second height, where the second height is greater than the first height.

Implementations may include one or more of the following features. For example, the barrel may include a frame, a first endplate having a curved shape and a second endplate having a curved shape. The first endplate and the second endplate may be coupled to the frame to form the barrel, where the barrel has a bulleted shape in both a lateral direction and a posterior direction. The barrel may include a frame, a first endplate, a second endplate, a first actuator having a split ramp inserted into the frame, a second actuator having a split ramp inserted into the frame and a central screw inserted through the first actuator and the second actuator, where the first actuator and the second actuator are configured to act on the first endplate and the second endplate in response to a rotation of the central screw. The barrel may include a first window and a second window, where the first window and the second window may be configured to receive graft packing material. The barrel may include a first endplate having a shaped groove and a second endplate having a shaped groove.

For example, in one implementation, the first portion and the second portion may be rails that extend from a same side of the barrel. For example, in another implementation, the first portion and the second portion may be rails that each extend from a different side of the barrel.

For example, the first plate and the second plate are each shaped in a lordotic profile. The first plate may include a bushing to enable the first plate to angulate about the bushing and the second plate may include a bushing to enable the second plate to angulate about the bushing. The first plate may be locked in position using a first set screw at any position within a range of motion for the first plate and the second plate may be locked in position using a second set screw at any position within a range of motion for the second plate. The first set screw may include a cup-shaped end to lock the first plate in position and the second set screw may include a cup-shaped end to lock the second plate in position.

In another general aspect, an implantable device includes a barrel having a first portion and a second portion, a first plate having multiple projections extending from one side of the first plate, where the first plate is configured to movably couple to the first portion of the barrel and to angulate about an axis of the first portion, and a second plate having multiple projections extending from one side of the second plate, where the second plate is configured to movably couple to the second portion of the barrel and to angulate about an axis of the second portion. The first plate and the second plate are each shaped in a lordotic profile.

Implementations may include one or more of the following features. For example, the first plate may be configured to angulate up to about 25 degrees about the axis of the first portion and the second plate may be configured to angulate up to about 25 degrees about the axis of the second portion. In one implementation, the first portion and the second portion may be rails that extend from a same side of the barrel. In another implementation, the first portion and the second portion may be rails that each extend from a different side of the barrel.

For example, the barrel may be configured to transition from a collapsed form having a first height to an expanded form having a second height, where the second height is greater than the first height. The first plate may be locked in position using a first set screw at any position within a range of motion for the first plate, where the first set screw has a cup-shaped end, and the second plate may be locked in position using a second set screw at any position within a range of motion for the second plate, where the second set screw has a cup-shaped end.

In another general aspect, a method includes inserting a barrel of an implantable device into an interspinous space. The implantable medical device includes the barrel having a first portion and a second portion, a first plate having multiple projections extending from one side of the first plate and a second plate having multiple projections extending from one side of the second plate. The method includes expanding the barrel from a collapsed form having a first height to an expanded form having a second height, where the second height is greater than the first height, moving the first plate on the first portion to engage a spinous process and moving the second plate on the second portion to engage the spinous process.

Implementations may include one or more of the following features. For example, the method may include engaging set screws in the first plate and the second plate to lock the first plate and the second plate in position. The method may include positioning the first plate to a desired angle with respect to the first portion, positioning the second plate to a desired angle with respect to the second portion and engaging set screws in the first plate and the second plate to lock the first plate and the second plate in position.

In another general aspect, an implantable device may include a barrel, the barrel having an upper portion and a lower portion. The implantable device may further include an actuator assembly disposed in the barrel, the actuator assembly comprising a front ramped actuator in engagement with the barrel, a rear ramped actuator in engagement with the barrel, and a central screw that extends from the rear ramped actuator through the front ramped actuator. The implantable device may further include a first plate having multiple projections extending from one side of the first plate, the first plate comprising a first portion that extends from the upper portion and a second portion that extends form the lower portion. The implantable device may further include a second plate having multiple projections extending from one side of the second plate, the second plate configured to be received on the central screw. The barrel may be configured to transition from a collapsed form having a first height to an expanded form having a second height and wherein the second height is greater than the first height.

In another general aspect, a method may include implanting a medical device in a patient, the method comprising: inserting a barrel of the device between adjacent spinous process, the medical device comprising a first plate disposed on one end of the barrel; rotating a central screw disposed in the barrel to cause the barrel to expand from a collapsed form having a first height to an expanded form having a second height; and ratcheting a second plate onto the central screw such that the first plate and the second plate engage the adjacent spinous process, the second plate being free to rotate about its center within a range of motion.

In another general aspect, an implantable device may comprise a barrel, the barrel having an upper portion and a lower portion. The implantable device may further an actuator assembly disposed in the barrel, the actuator assembly comprising a front ramped actuator in engagement with the barrel, a rear ramped actuator in engagement with the barrel, and a central screw that extends from the rear ramped actuator through the front ramped actuator. The implantable device may further comprise a first plate. The first plate may comprise a first portion that extends from the upper portion, a second portion that extends form the lower portion, and a pivoting spike assembly disposed in the first plate. The pivoting spike assembly may comprise multiple projections extending from a first side of the first plate. The implantable device may further comprise a second plate having multiple projections extending from a first side of the second plate, the second plate configured to be received on the central screw. The barrel may be configured to transition from a collapsed form having a first height to an expanded form having a second height and wherein the second height is greater than the first height.

In another general aspect, a method for implanting a medical device in a patient may comprise: inserting a barrel of the device between adjacent spinous processes, the medical device comprising a first plate disposed on one end of the barrel; rotating a central screw disposed in the barrel to cause the barrel to expand from a collapsed form having a first height to an expanded form having a second height; and inserting a second plate onto the central screw such that the first plate and the second plate engage the adjacent spinous process wherein at least one of the first plate or the second plate comprises a pivoting spike assembly that is allowed to freely articulate until engagement with the adjacent spinous process compresses the pivoting spike assembly locking the pivoting spike assembly in place.

In another general aspect, a method of assembling a medical device may comprise providing a medical device comprising a first plate extending from at least one side of a central barrel; inserting a spike assembly into an opening in the first plate such that a hole in the spike assembly is aligned with a hole in the first plate; inserting a fastener through the hole in the spike assembly and the hole in the first plate such that a lobe of the fastener engages the spike assembly; rotating the fastener while disposed in the hole of the spike assembly and the hole in the first plate such that the fastener causes a leaf spring feature of the spike assembly to expand; and further inserting the fastener through the hole in the spike assembly and the hole in the first plate to push the lobe below the leaf spring feature and into a groove in the spike assembly.

The details of one or more implementations are set forth in the accompanying drawings and the description below. Other features will be apparent from the description and drawings, and from the claims.

BRIEF DESCRIPTION OF THE DRAWINGS

FIG. 6 is a top view of the medical device of FIG. 5.
FIG. 7 is a front view of the medical device of FIG. 5.
FIG. 8 is a side view of the medical device of FIG. 5.
FIG. 18 is a top view of the medical device of FIG. 17.
FIG. 19 is a front view of the medical device of FIG. 17.
FIG. 20 is a side view of the medical device of FIG. 17.

FIG. 30 is an exploded top view of a barrel of a medical device according to an example implementation.

FIG. 36 is a top view of the medical device of FIG. 35.

FIG. 37 is a front view of the medical device of FIG. 35.

FIG. 38 is a side view of the medical device of FIG. 35.

FIG. 53 is a rear view of the medical device of FIG. 50.

FIG. 54 is a top view of the medical device of FIG. 50.

FIGS. 59-62 illustrate assembly of an expandable central barrel of a medical device according to one example implementation.

FIGS. 71-73 illustrate assembly of a locking plate for a medical device according to one example implementation.

FIGS. 82-85 illustrate assembly of the barrel for the medical device of FIG. 76 in accordance with one example implementation.

DETAILED DESCRIPTION

Figure 1:
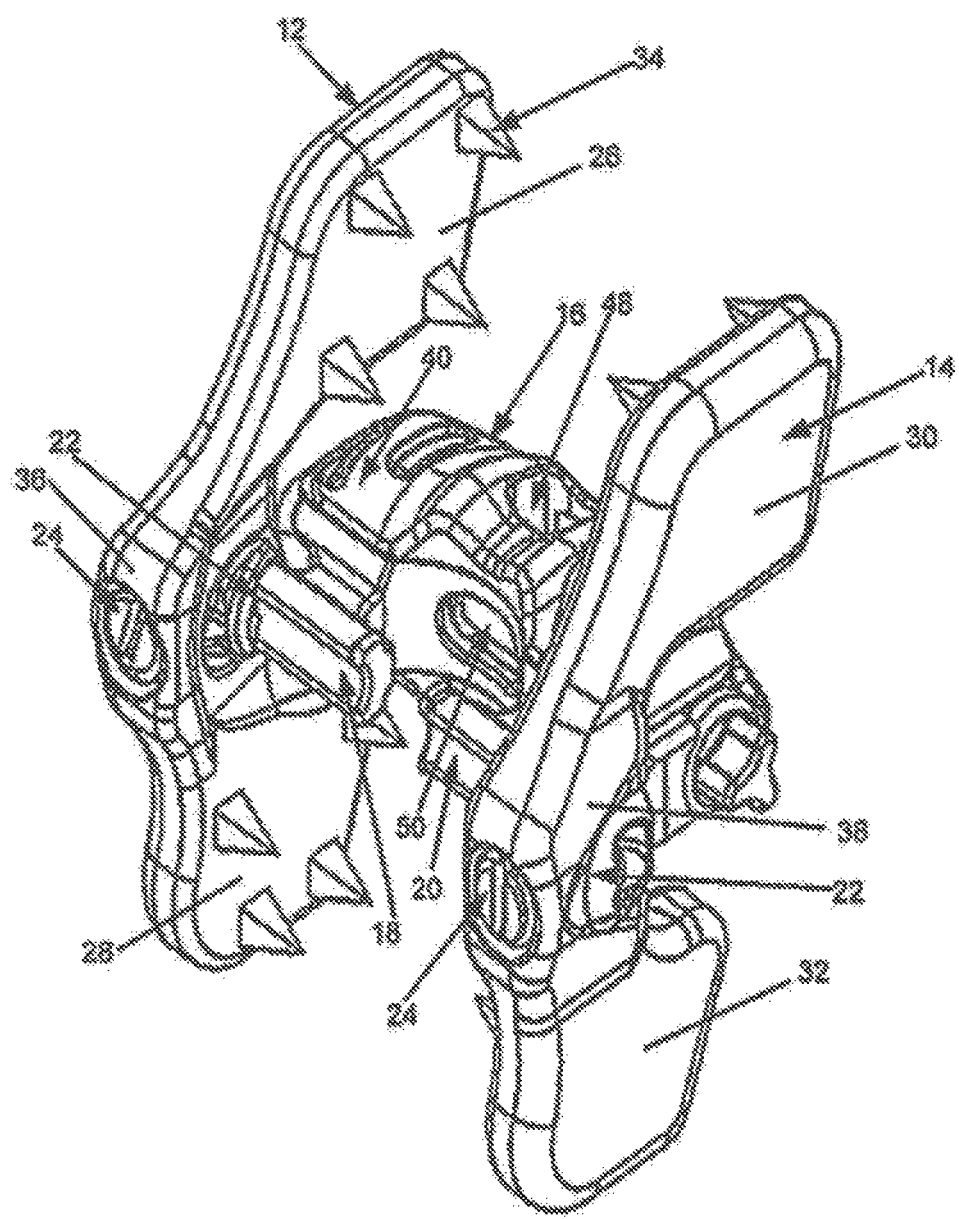
FIG. 1 is a perspective view of a medical device according to an example implementation.

Detailed implementations of the present invention are disclosed herein; however, it is to be understood that the disclosed implementations are merely examples of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The devices and methods described herein are generally directed to medical devices that can be used to support, stabilize and/or replace anatomical structures within a body of a patient. In some implementations, the devices and methods described herein are configured to provide support to a spine or back of a patient, including providing support between two vertebrae in the spine or back of the patient. In other implementations, other portions of the body of the patient can be supported by the devices described herein.

The medical devices described herein may be implanted within a body of a patient to assist in maintaining normal physiologic motion in the spine of the patient.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, human male, or any other mammal.

This document describes implementations of an implantable medical device that may be used as a posterior, non-pedicle supplemental fixation device for use in the non-cervical spine. The medical device may be used as an interspinous fusion device. The medical device may be implanted with or without the removal of the supraspinous ligament. In one or more implementations, the supraspinous ligament may be preserved. The medical device may be attached firmly to the spinous processes above and below an interspinous space. The medical device may immobilize a lumbar motion segment posteriorly with no other devices implanted. The medical device may withstand compressive, torsional and shear loads seen in the lumbar spine. The medical device may be used to achieve supplemental fusion and to treat conditions of the spine such as, for example, degenerative disc disease, spondylolisthesis, trauma (i.e., fracture or dislocation), tumor and/or other conditions.

This document describes implementations of an implantable medical device, where the medical device may include an expandable central barrel with polyetheretheketone (PEEK) bone contacting endplates, with two spiked plates attached to the central barrel. For example, the two spiked plate may be held together on posterior rails. By way of further example, one of the spiked plates may be on one end of the expandable central barrel (e.g., integrally formed with the central barrel) with another one of the spiked plates being attached after the barrel is inserted into the interspinous space to clamp the device in place. The plates may include projections (e.g., spikes) that bite into the spinous process to clamp the device in place. Each of the plates may angulate to conform to the patient anatomy. The plates may be locked with a set screw and may have a lordotic profile to match the lumbar anatomy. The expandable barrel may provide interspinous distraction, off-loading the spikes on the plate and reducing the chances of breaking the spinous process. The barrel may be sized to fit into the interspinous space without resistance, and then expanded. The barrel may include a graft window (e.g., anteriorly and posteriorly) which may be packed with graft material after expansion. In some embodiments, the barrel includes a graft window anteriorly and posteriorly and can be packed with the graft material using the posterior window. The PEEK endplates may include anatomically-shaped grooves for optimal bone contact and fit.

Figure 2:
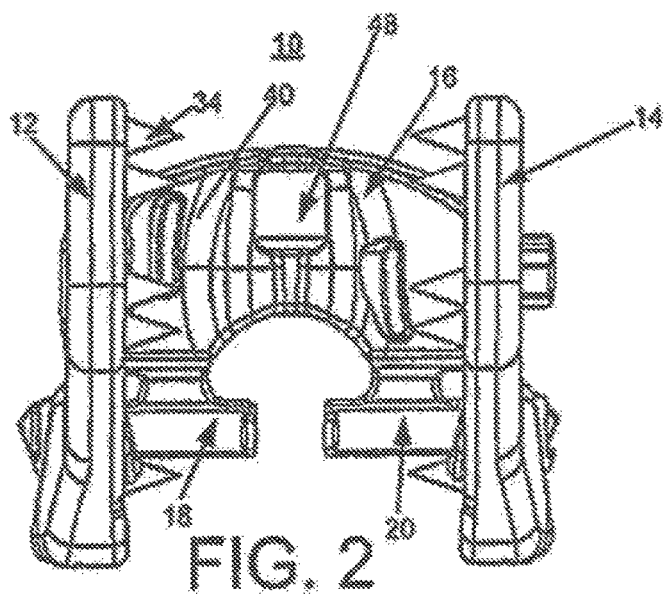
FIG. 2 is a top view of the medical device of FIG. 1.
Figure 3:
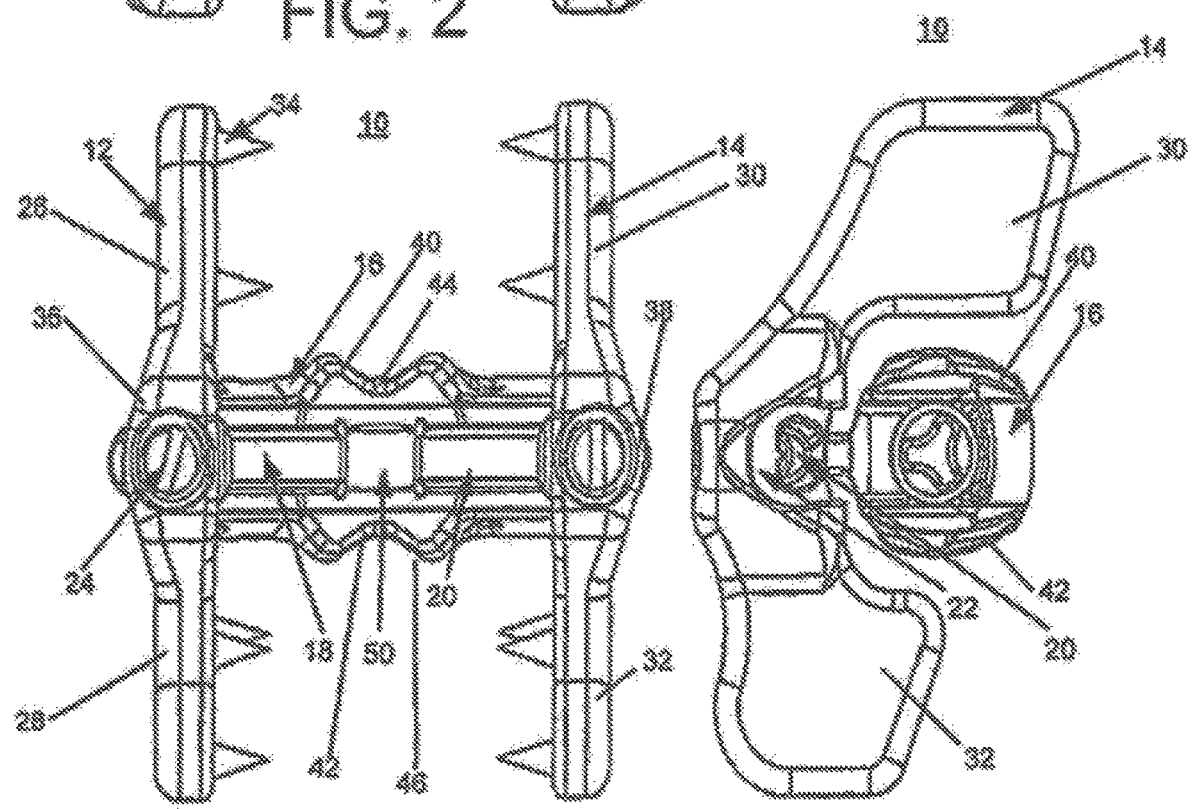
FIG. 3 is a front view of the medical device of FIG. 1.
Figure 4:
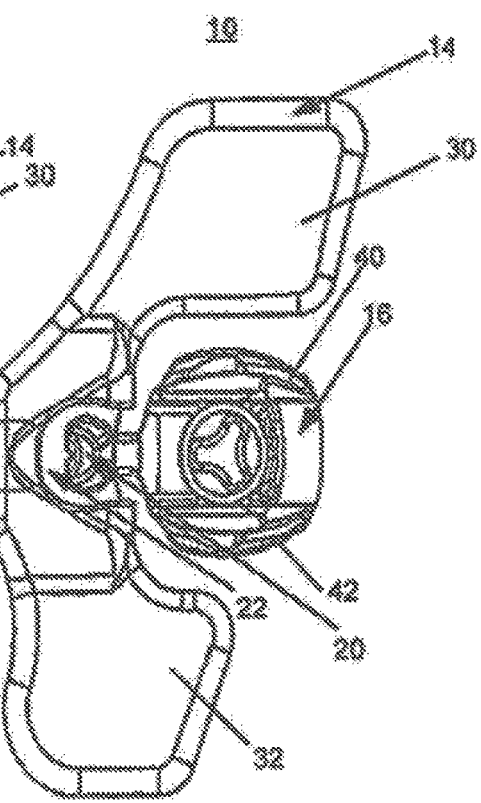
FIG. 4 is a side view of the medical device of FIG. 1.
Figure 5:
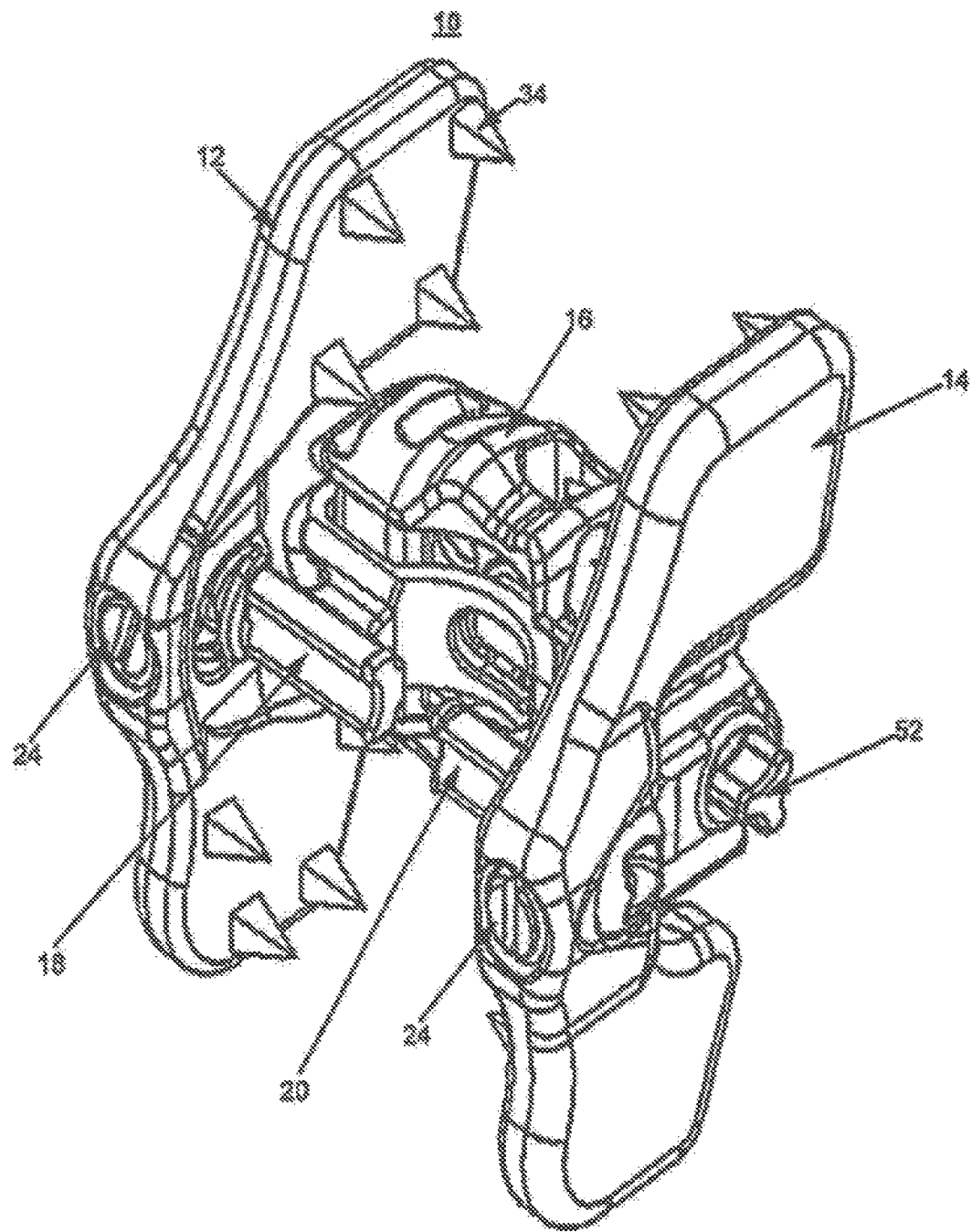
FIG. 5 is a perspective view of a medical device according to an example implementation.
Figure 9:
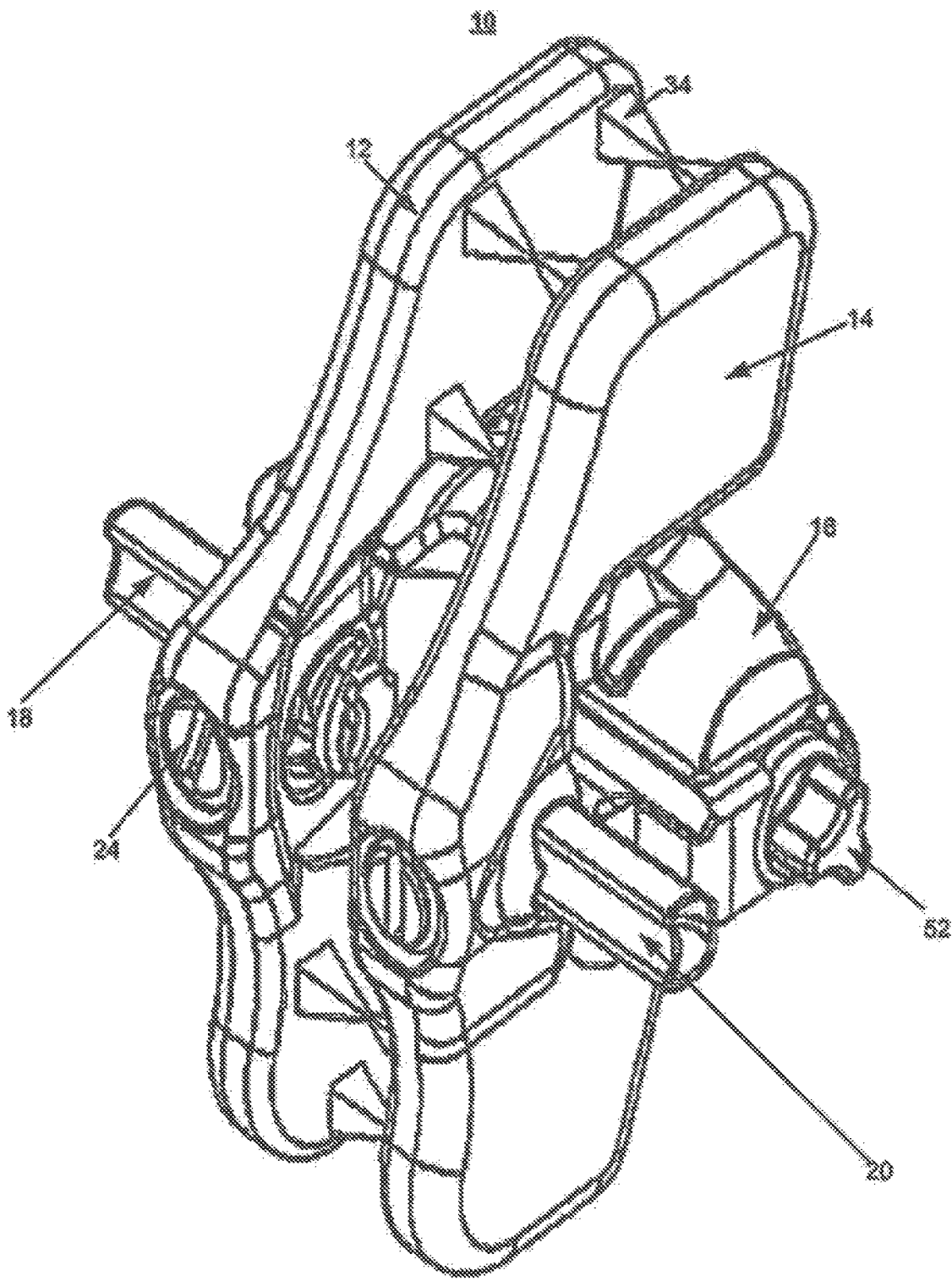
FIG. 9 is a perspective view of a medical device according to an example implementation.
Figure 10:
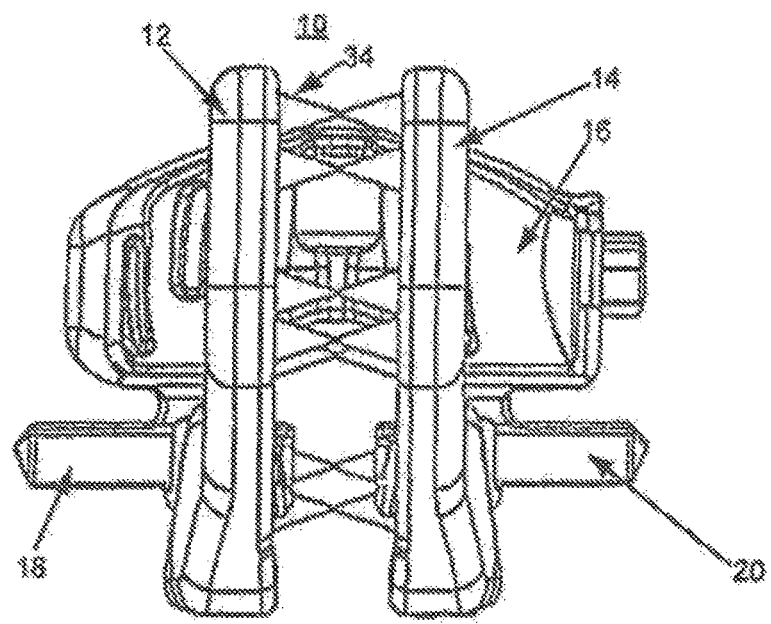
FIG. 10 is a top view of the medical device of FIG. 9.
Figure 11:
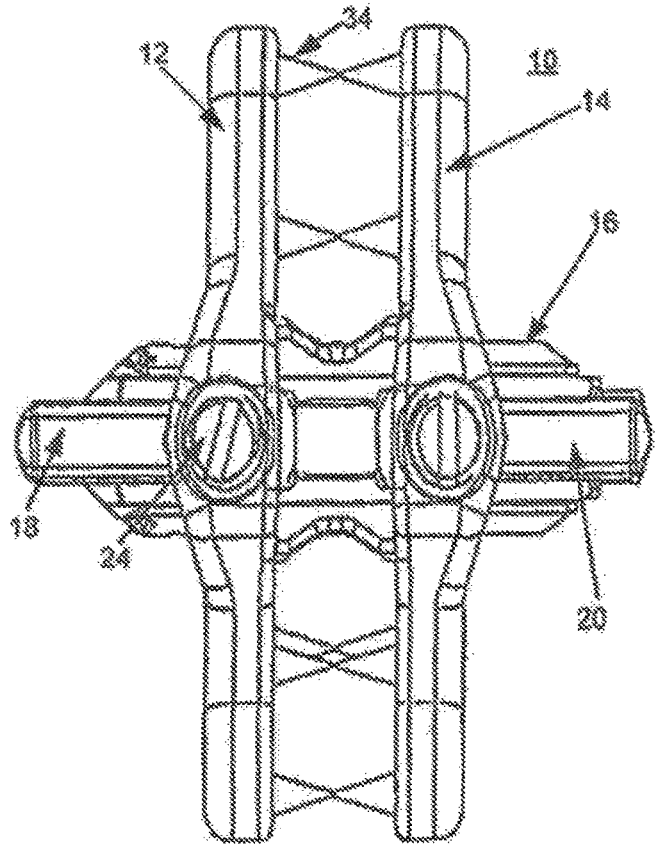
FIG. 11 is a front view of the medical device of FIG. 9.
Figure 12:
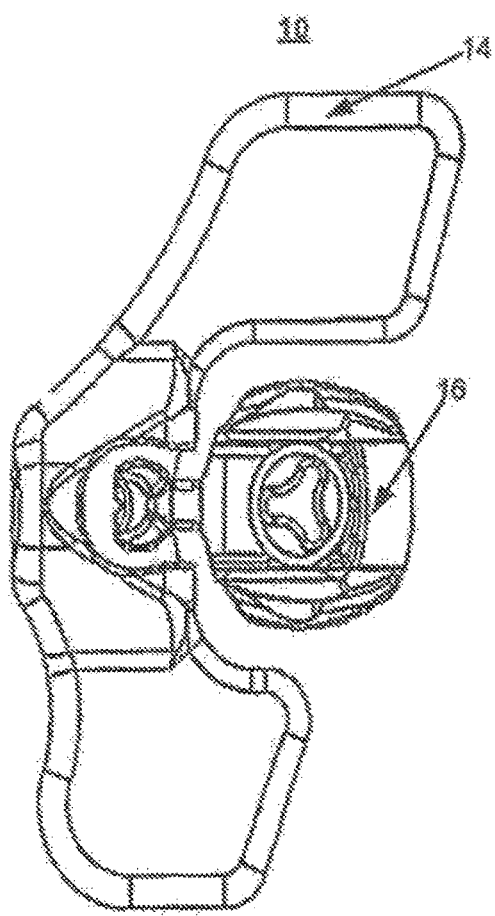
FIG. 12 is a side view of the medical device of FIG. 9.
Figure 13:
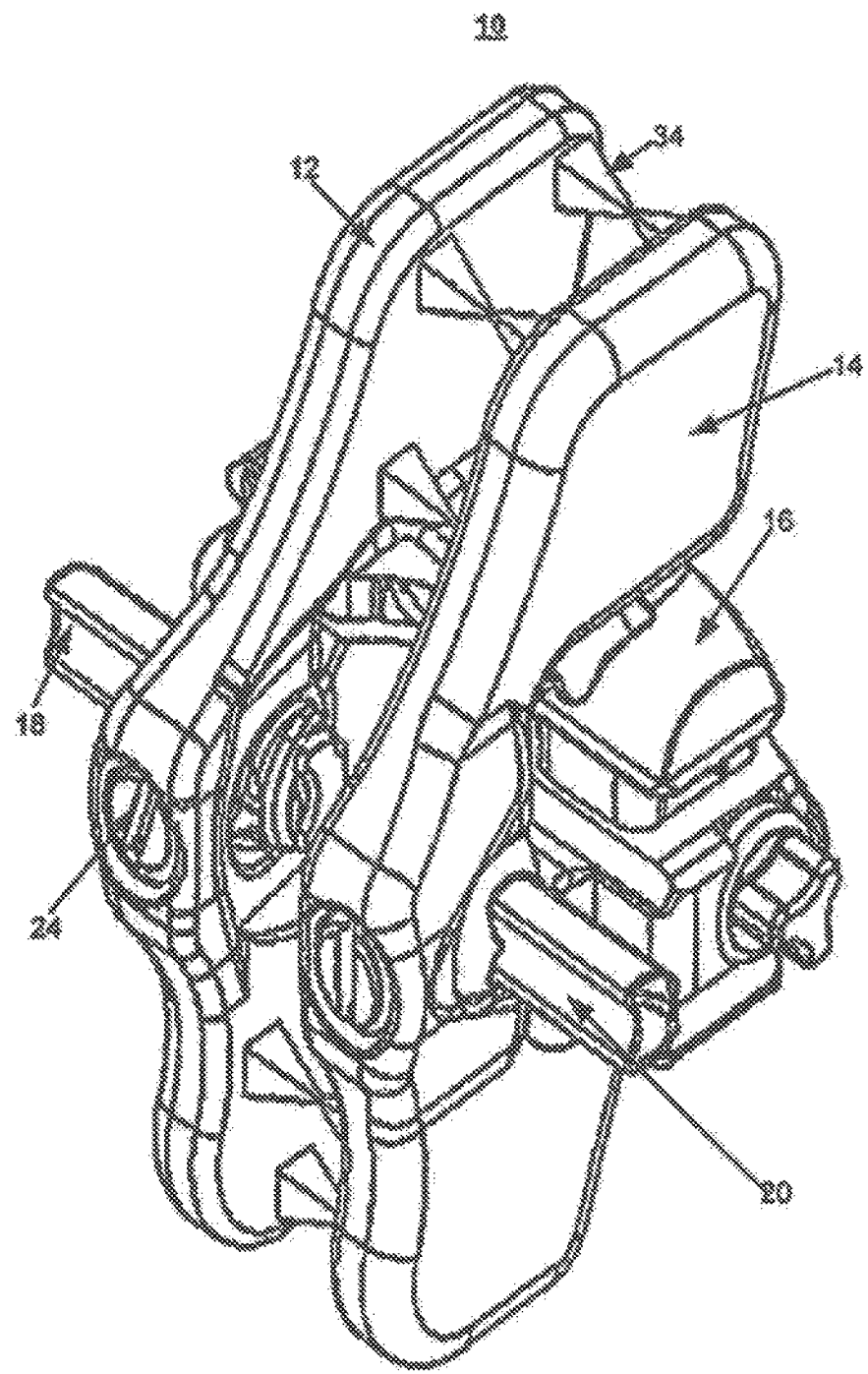
FIG. 13 is a perspective view of a medical device according to an example implementation.
Figure 14:
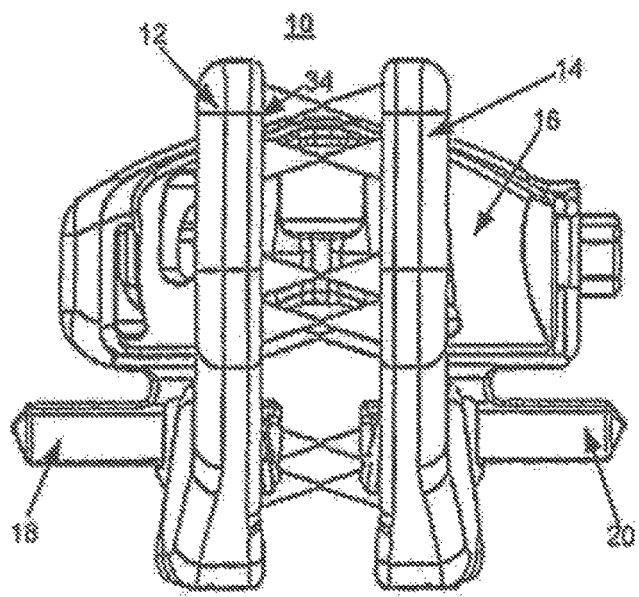
FIG. 14 is a top view of the medical device of FIG. 13.
Figure 15:
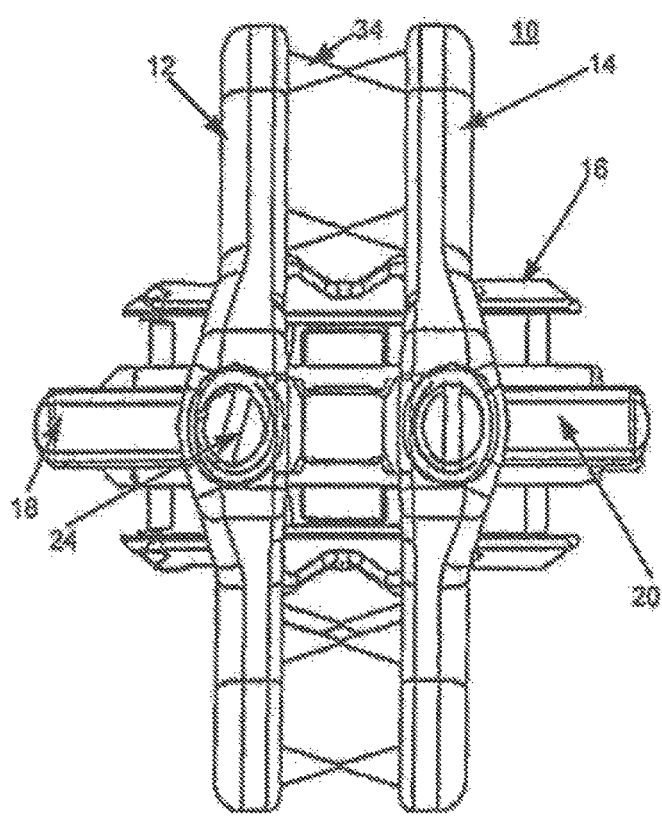
FIG. 15 is a front view of the medical device of FIG. 13.
Figure 16:
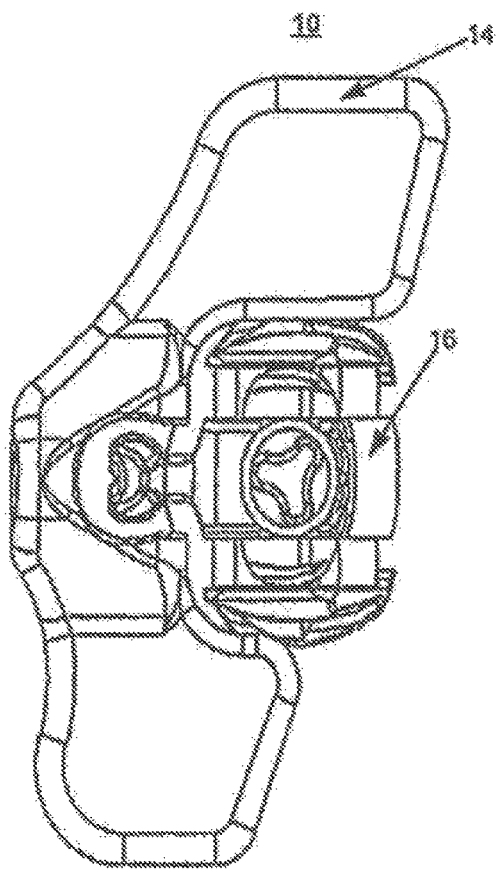
FIG. 16 is a side view of the medical device of FIG. 13.
Figure 17:
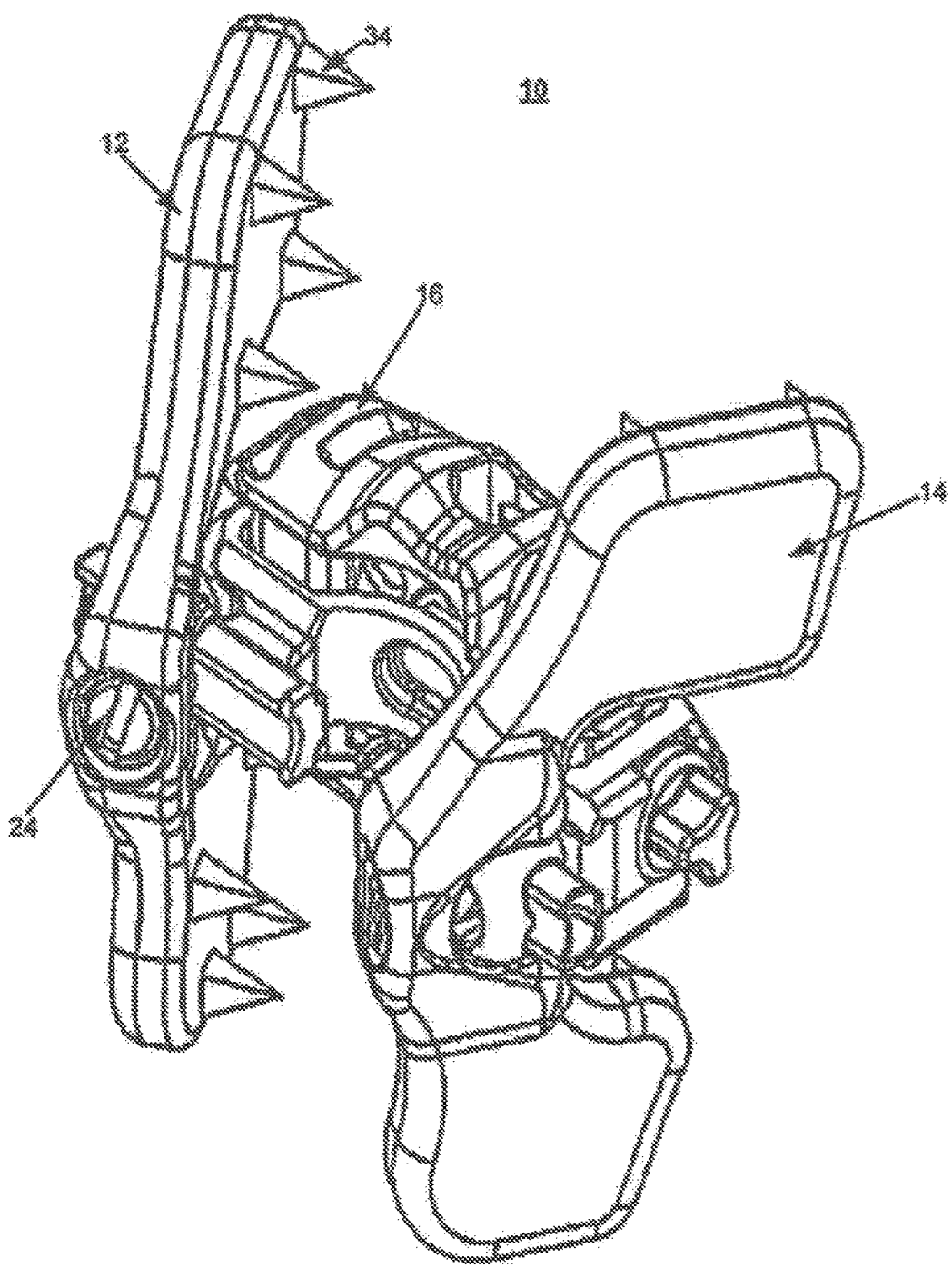
FIG. 17 is a perspective view of a medical device according to an example implementation.
Figure 21:
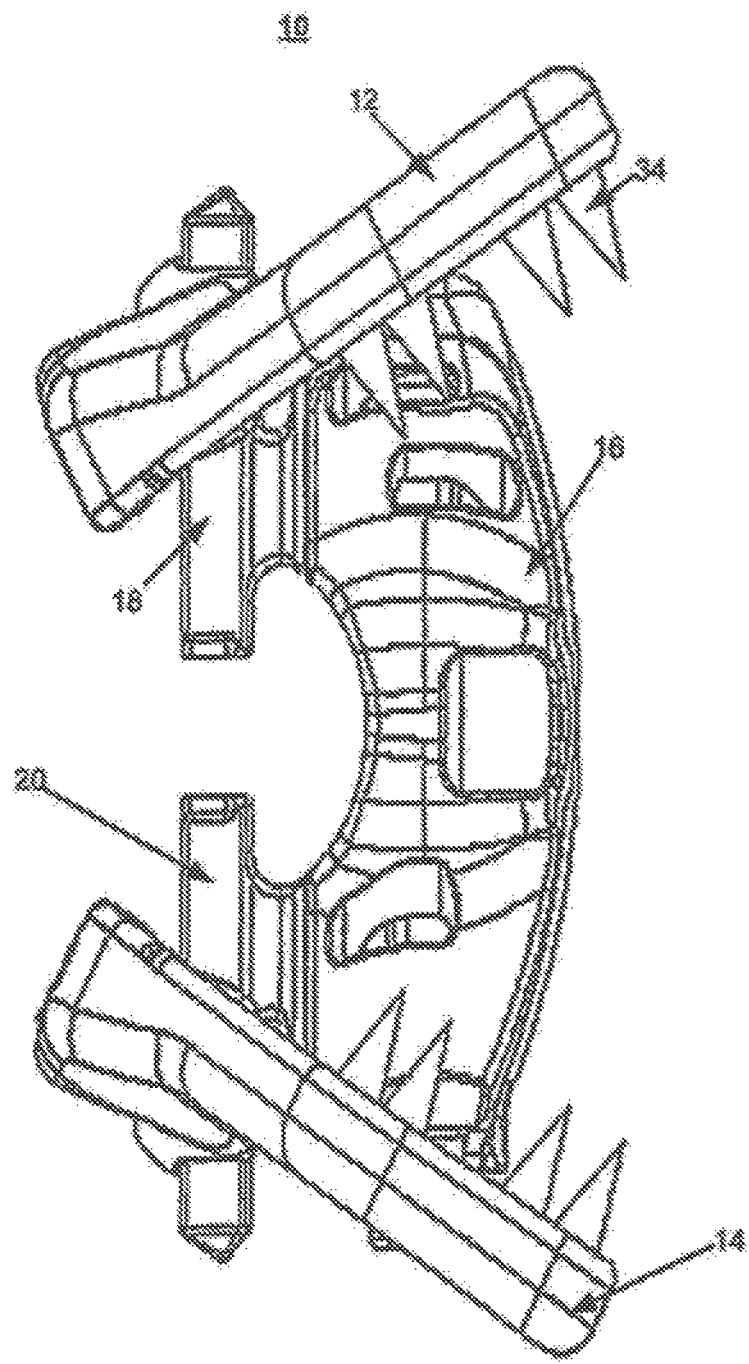
FIG. 21 is a top view of a medical device according to an example implementation.

FIGS. 1-4 illustrate a medical device 10 according to one example implementation. The medical device 10 may be implanted in a patient and referred to as a spinous process fusion device. FIG. 1 is a perspective view of the medical device 10 with a barrel illustrated in a collapsed or contracted position and the plates in a separated position relative to one another. FIGS. 2-4 illustrate a top view, front view and side view, respectively, of the medical device 10 of FIG. 1, which illustrates the barrel in the collapsed or contracted position.

The medical device 10 includes a first plate 12, a second plate 14 and an expandable central barrel (also referred to as a barrel) 16. The barrel 16 is illustrated in a collapsed state.

The barrel 16 includes a first portion 18 (e.g., a first rail 18) and a second portion 20 (e.g., a second rail 20). The first rail 18 and the second rail 20 also may be referred to as the rails 18 and 20. The first rail 18 and the second rail 20 may be integrally formed with the barrel 16. The first rail 18 and the second rail 20 also may be referred to as posterior rails. The first plate 12 and the second plate 14 (also referred to as the plates 12 and 14) may be secured to the barrel 16 by coupling the first plate 12 to the first rail 18 and the second plate 14 to the second rail 20. The first plate 12 and the second plate 14 each may include a bushing 22 (e.g., a spherical bushing) assembled into the plates 12 and 14, where the plates 12 and 14 slide on the respective rails 18 and 20 through the bushing 22 and are secured using a set screw 24. As discussed in more detail below, each plate 12 and 14 may move laterally along its respective rail 18 and 20 to engage spinous processes of adjacent vertebra above and below the interspinous space. FIGS. 1-4 illustrate the plates 12 and 14 in a separated position with respect to one another. Also, as discussed in more detail below, each plate 12 and 14 may angulate through a range of degrees with respect to the rails 18 and 20 to better conform to patient anatomy when implanted in a patient.

In other example implementations (not shown), the first portion 18 and the second portion 20 may be grooves on the barrel 16. In this example, the first plate 12 and the second plate 14 each may include a projection (e.g., a rail) that is movably inserted into the corresponding groove on the barrel 16. This example implementation may function in the same way as described above and below, other than the structure of the rails may be implemented on the plates 12 and 14, which are then received in the first portion 18 and the second portion 20 of the barrel 16, where the first portion 18 and the second portion 20 are grooves on the barrel 16.

The first plate 12 may include an upper portion 26 and a lower portion 28. The second plate 14 may include an upper portion 30 and a lower portion 32. The plates 12 and 14 may include multiple projections 34 (e.g., spikes) on both the upper portions 26 and 30 and the lower portions 28 and 32. While the term spikes may be used for the projections 34 other types of projections may be used that may have a more tapered point or rounded point or other type of ending to the projection. The spikes 34 may be used to attach firmly and bite into the spinous processes above and below an interspinous space. The spikes 34 may be integrally formed with the plates 12 and 14 or the spikes 34 may be separate components that are secured to the plates 12 and 14. The spikes 34 may be pyramid shaped with a base portion secured or integrally formed on the plates 12 and 14. The sides of the spikes 34 may extend from the base to form a point in the shape of a pyramid. In other example implementations, the spikes 34 may be formed into other shapes that rise to a point to enable the spike to engage the spinous process. As discussed above, the end of the spikes 34 may include tips other than a point such as, for example, rounded tip, a square tip or other-shaped tip.

The plates 12 and 14 and the spikes 34 may be made of titanium. In other implementations, the plates 12 and 14 and the spikes 34 may be made of other biocompatible materials.

The example illustration of the medical device 10 includes four (4) spikes 34 on each portion 26, 28, 30 and 32 of the plates 12 and 14. In other example implementations, fewer or more spikes 34 may be included. In one example implementation, the spikes 34 on opposing portions (i.e., upper portions 26 and 30 and lower portions 28 and 32) may be aligned across from one another. In other example implementations, the spikes 34 on opposing portions may be offset from one another.

The first plate 12 and the second plate 14 may be shaped in a lordotic profile to match the lumbar anatomy. With respect to the first plate 12, the upper portion 26 is connected to the lower portion 28 by a central portion 36. The upper portion 26, the lower portion 28 and the central portion 36 may be integrally formed as a single plate component. The central portion 36 includes an open side (e.g., a C-shaped opening) to receive the bushing 22 and an opening (e.g., a hole) to receive the set screw 24, as illustrated in more detail in FIGS. 24-27. In other example implementations, the first plate 12 and the second plate 14 may be other shapes suitable for a particular application.

Similarly to the first plate 12, the second plate 14 includes a central portion 38 that connects the upper portion 30 to the lower portion 32. The upper portion 30, the lower portion 32 and the central portion 38 may be integrally formed as a single plate component. The central portion 38 include an open side (e.g., a C-shaped opening) to receive the bushing 22 and an opening (e.g., a hole) to receive the set screw 24, as illustrated in more detail in FIGS. 24-27. The set screw 24 is used to lock the plates 12 and 14 in an angular position at any position within their range of angular motion.

The central barrel 16 is an expandable barrel that may be in a collapsed position for insertion into a patient in the interspinous space without resistance and then expanded up to the barrel's maximum height. In one example implementation, the maximum expanded height of the barrel may be about 4 mm greater than the collapsed height.

The central barrel 16 includes a first endplate 40 and a second endplate 42 (also referred to as endplates 40 and 42), as best viewed in FIG. 3. Each of the endplates 40 and 42 includes a respective groove 44 and 46. The grooves 44 and 46 may be anatomically-shaped grooves optimal bone contact and fit in the patient. The endplates 40 and 42 may be PEEK bone contacting endplates. The barrel 16 may be bullet-shaped on both ends in the lateral and posterior directions to facilitate insertion into a patient. The expandable barrel 16 may provide interspinous distraction and may offload the forces of the spikes 34 on the plates 12 and 14 to reduce the chances of breaking a spinous process. The barrel 16 may be inserted, laterally or posteriorly, in a smaller height and then expanded to provide distraction, eliminating forces on the spinous process and potential frustration for a surgeon performing the implantation.

The barrel 16 includes a first window 48 (e.g., also referred to as an opening or an anterior window) and a second window 50 (e.g., also referred to as an opening or a posterior window). The first window 48 and the second window 50 may be used as graft windows for the packing of bone graft material following the insertion and placement of the medical device 10 in a patient. In one implementation, after the barrel 16 has been expanded, the barrel 16 may be packed with bone graft using the second window 50. In this manner, graft containment areas accessed by the windows 48 and 50 may provide for a larger grafting area and may be packed after expansion of the barrel 16.

Referring to FIGS. 5-8, an example implementation of the medical device 10 of FIGS. 1-4 is illustrated with the barrel 16 shown in an expanded state and the plates 12 and 14 shown in a separated position with respect to one another. That is, the plates 12 and 14 are each positioned towards an outer end of the rails 18 and 20. The barrel 16 expands and contracts by expanding and contracting the endplates 40 and 42 in a direction towards the upper 26 and 30 and lower portions 28 and 32 of the sides 12 and 14, respectively. The mechanism to expand and contract the barrel 16 is illustrated in more detail in FIGS. 28-30 below.

In general, a central screw 52 is rotated to actuate two independent internal actuators. The actuators include split ramps that raise and lower the endplates 40 and 42 when the central screw 52 is rotated. FIGS. 7 and 8 provide views that illustrate the barrel 16 in a fully expanded state. As discussed above, the barrel 16 may be expanded after insertion into the interspinous space. After expansion, the barrel 16 may be packed with bone graft material using the window 50. Prior to expansion, some bone graft material may be packed into the barrel 16 using the window 48.

Referring to FIGS. 9-12, an example implementation of the medical device 10 of FIGS. 1-4 is illustrated with the barrel 16 shown in a collapsed state and the plates 12 and 14 shown in a closed position. That is, the plates 12 and 14 have been traversed along the rails 18 and 20 towards one another. The plates 12 and 14 may slide along the rails 18 and 20 and may be secured in position at any point along the rails 18 and 20 using the set screw 24. When the plates 12 and 14 are slid together along the rails 18 and 20, the spikes 34 on the plates 12 and 14 may engage and clamp (or bite into) the spinous process. In this manner, the spikes 34 on the upper portions 26 and 30 may clamp together and into one spinous process and the spikes 34 on the lower portions 28 and 32 may clamp together and into an adjacent spinout process.

As illustrated in FIGS. 9-12, the spikes 34 on one plate are aligned to mate at a same point with the spikes 34 on an opposing plate. In other example implementations, the spikes 34 on one plate may be offset in relation to the spikes 34 on an opposing plate.

Referring to FIGS. 13-16, an example implementation of the medical device 10 of FIGS. 1-4 is illustrated with the barrel 16 shown in an expanded state and the plates 12 and 14 shown in a closed position. In this manner, this illustrates the medical device 10 in a state after insertion into the patient such that the plates 12 and 14 have been traversed along the rails 18 and 20 to clamp on the spinous process of adjacent vertebrae and the barrel 16 has been expanded using the central screw 52.

Referring to FIGS. 17-23, an example implementation of the medical device 10 of FIGS. 1-4 is illustrated with the barrel 16 shown in an expanded state and the plates 12 and 14 shown in an open or separated position and in an angulated configuration. As discussed above, the plates 12 and 14 may rotate angularly with respect to the rails 18 and 20. The plates 12 and 14 may pivot around the bushing 22 and may be locked in place using the set screw 24. In one example implementation, the plates 12 and 14 may have a range of motion of about 25 degrees offset with respect to the rails 18 and 20. The angulation of the plates 12 and 14 enables each plate to conform independently to the anatomy of the particular patient. Each plate 12 and 14 may be pivoted and locked at any position in their range of motion independent of the other plate.

Figure 22:
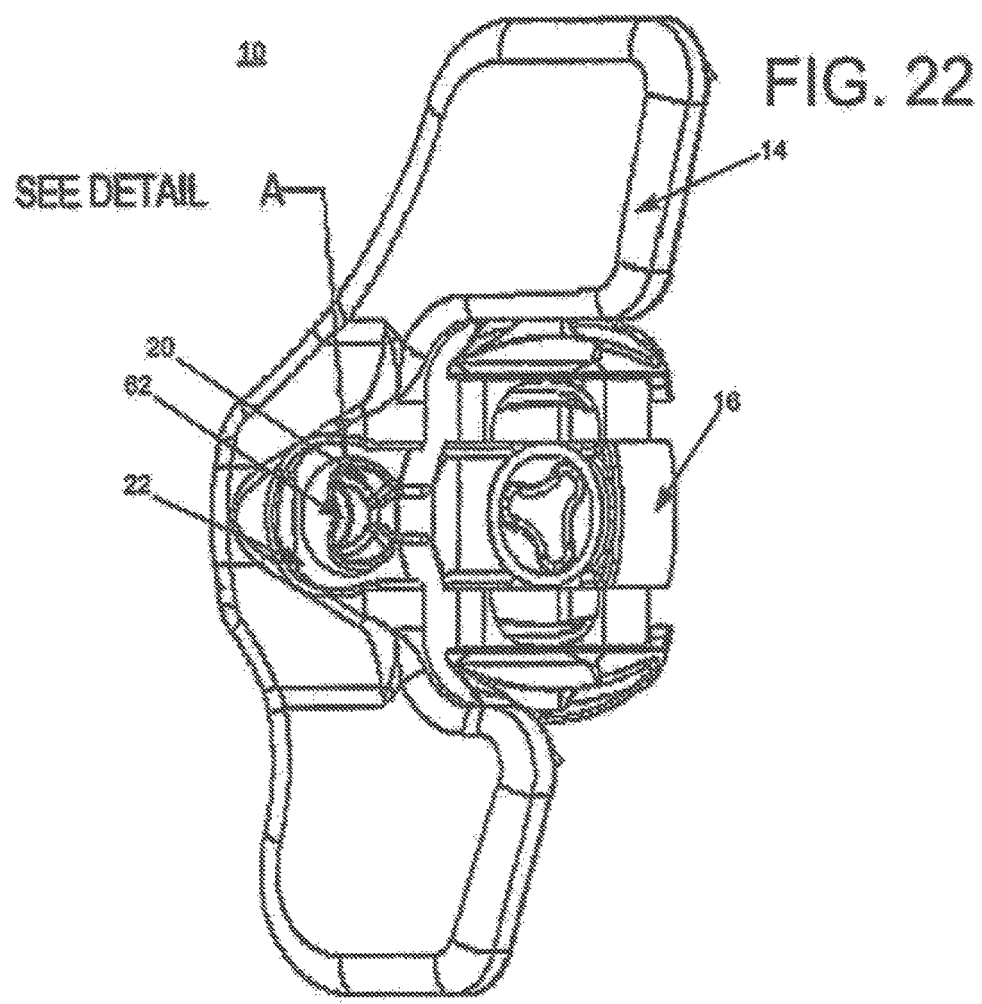
FIG. 22 is a side view of the medical device of FIG. 21.
Figure 23:
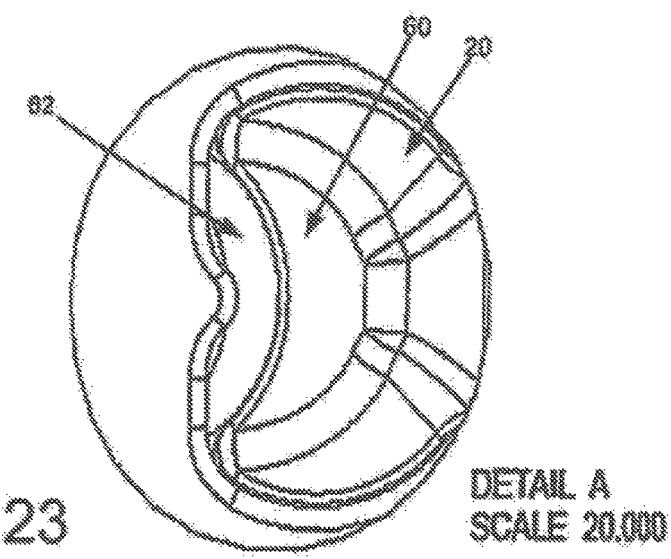
FIG. 23 is a detailed view of the inset A of FIG. 22.
Figure 24:
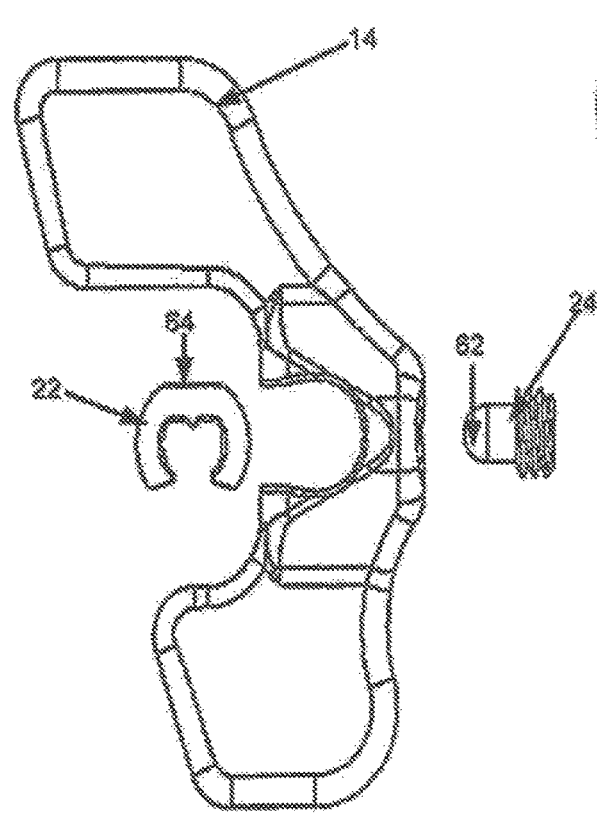
FIGS. 24-27 are side views of a plate of a medical device according to an example implementation.
Figure 25:
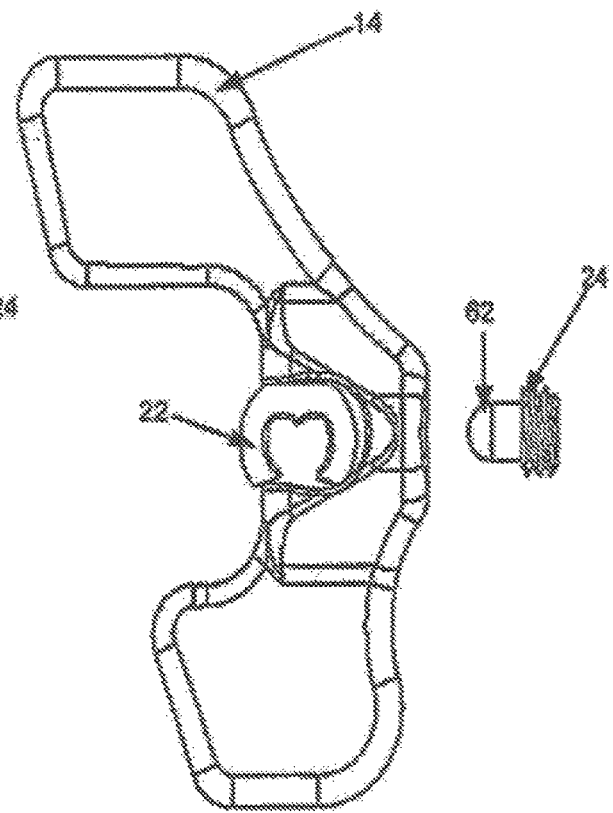

In FIGS. 22 and 23, a side view (FIG. 22) and a detailed view of inset A (FIG. 23) illustrate that the plates 12 and 14 are locked using the set screw 24. The rails 18 and 20 may be C-shaped or curved and include a groove area 60. The set screw 24 may include a curved, cup-shaped design on the tip 62. The curved tip 62 penetrates through the opening in the rail 14 and through the bushing 22 to engage the groove area 62 of the rail 20 to secure and lock the plate 14 in place. The curved tip 62 maximizes the surface contact with the groove area 62 of the rail 20 when the plate 14 pivots through its range of motion. FIGS. 24-27 below also illustrate the curved (or cup-shaped or bulleted) tip 62 of the set screw 24.

Referring to FIGS. 24-27, the assembly of the plates 12 and 14 is illustrated. In these example figures, plate 14 is referenced for illustrative purposes. The plate 14 may be assembled by placing the bushing 22 into the plate initially offset by 90 degrees from its final position. As described above, the bushing 22 may be a spherical bushing that is shaped to be positioned on and traverse the rail 20 on the barrel 16. The bushing 22 may include a slot 64 or opening in the back of the bushing to receive the set screw 24.

Figures 26, 27:
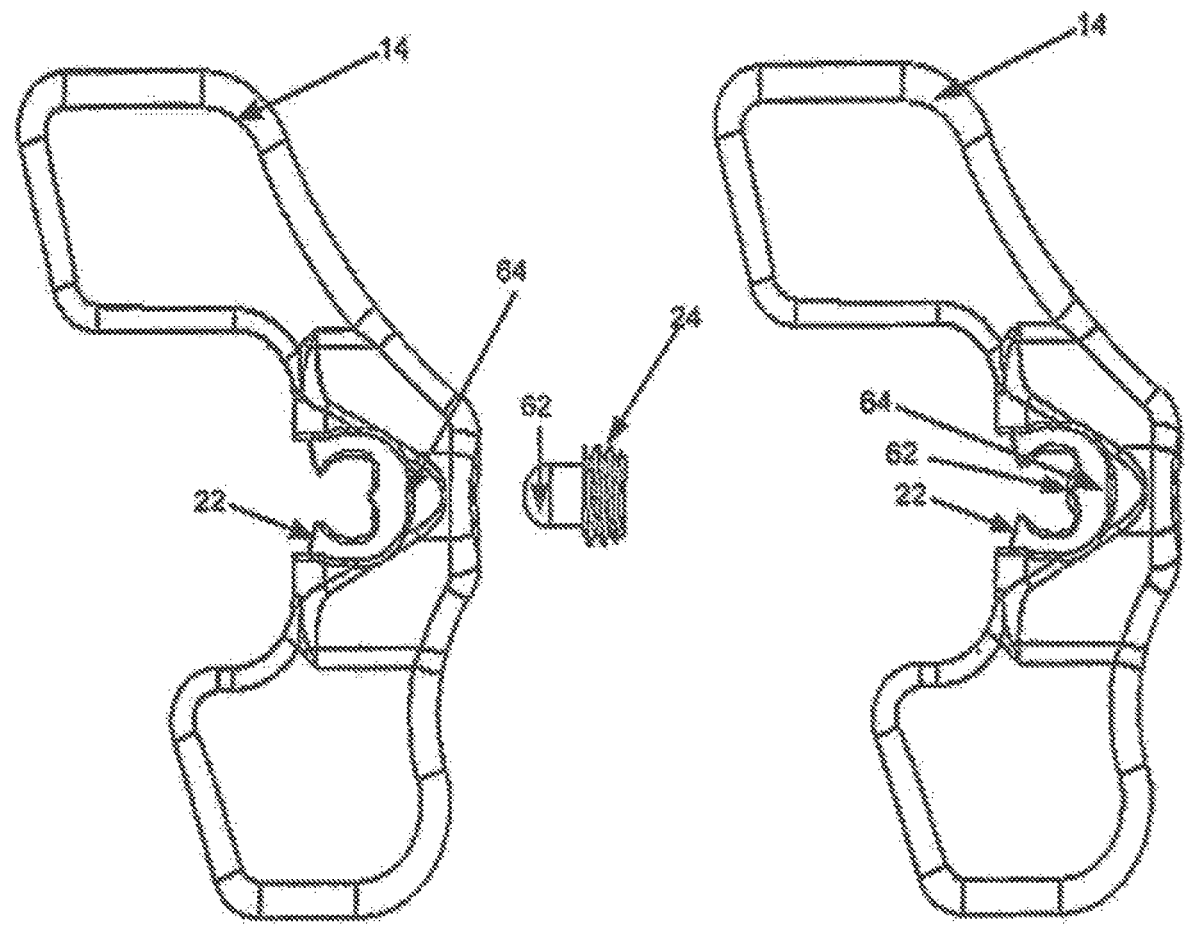

Once the bushing 22 has been inserted into the plate 14 (FIG. 25), the bushing 22 is rotated 90 degrees into its final position in the plate 14 (FIG. 26). Then, the set screw 24 having the curved tip 62 may be inserted through the opening in the back of the plate 14 through the slot 64 in the bushing 22. The set screw 24 serves to prevent the bushing 22 from rotating back out of the plate 14.

Figure 28:
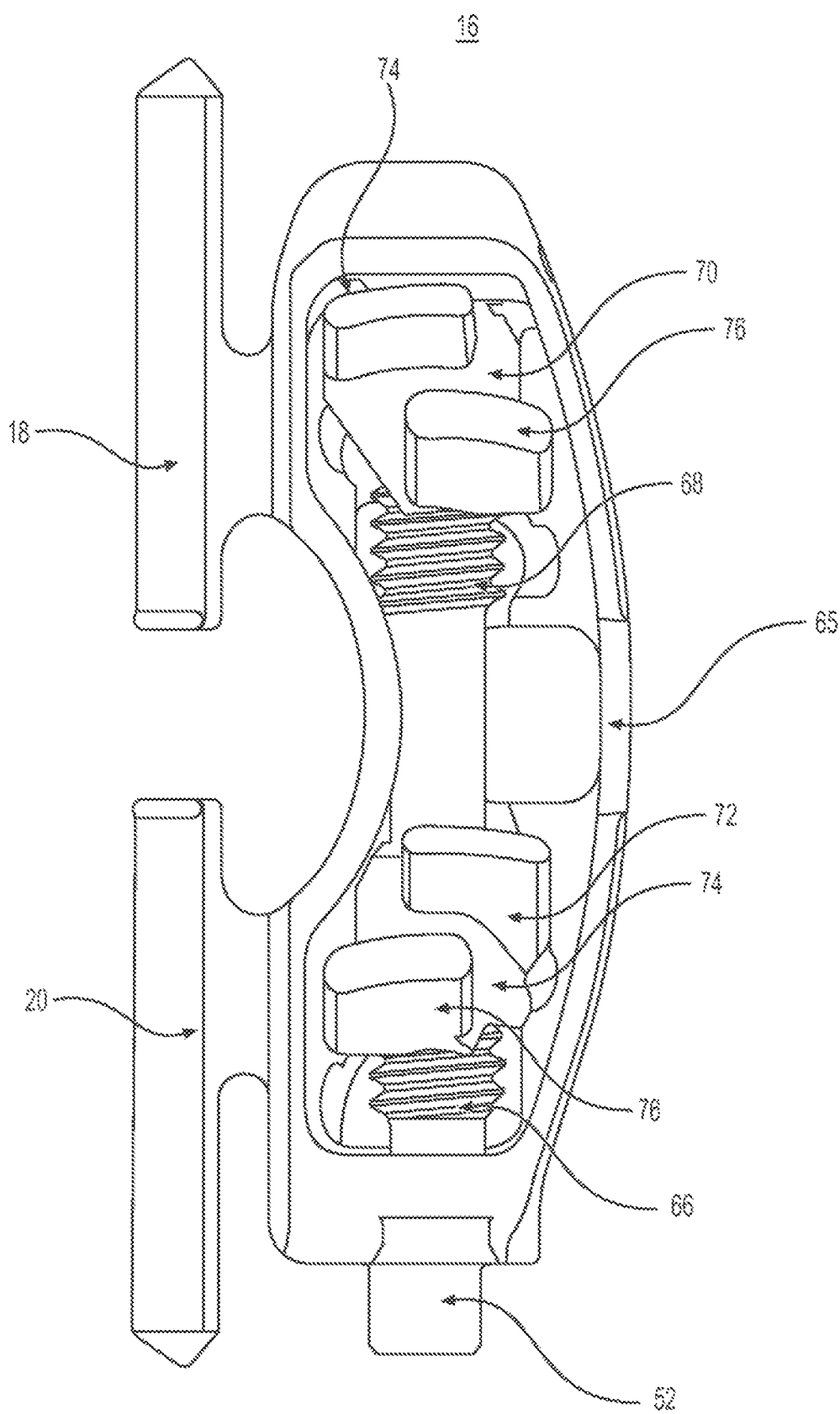
FIG. 28 is top view of a barrel of a medical device according to an example implementation.
Figure 29:
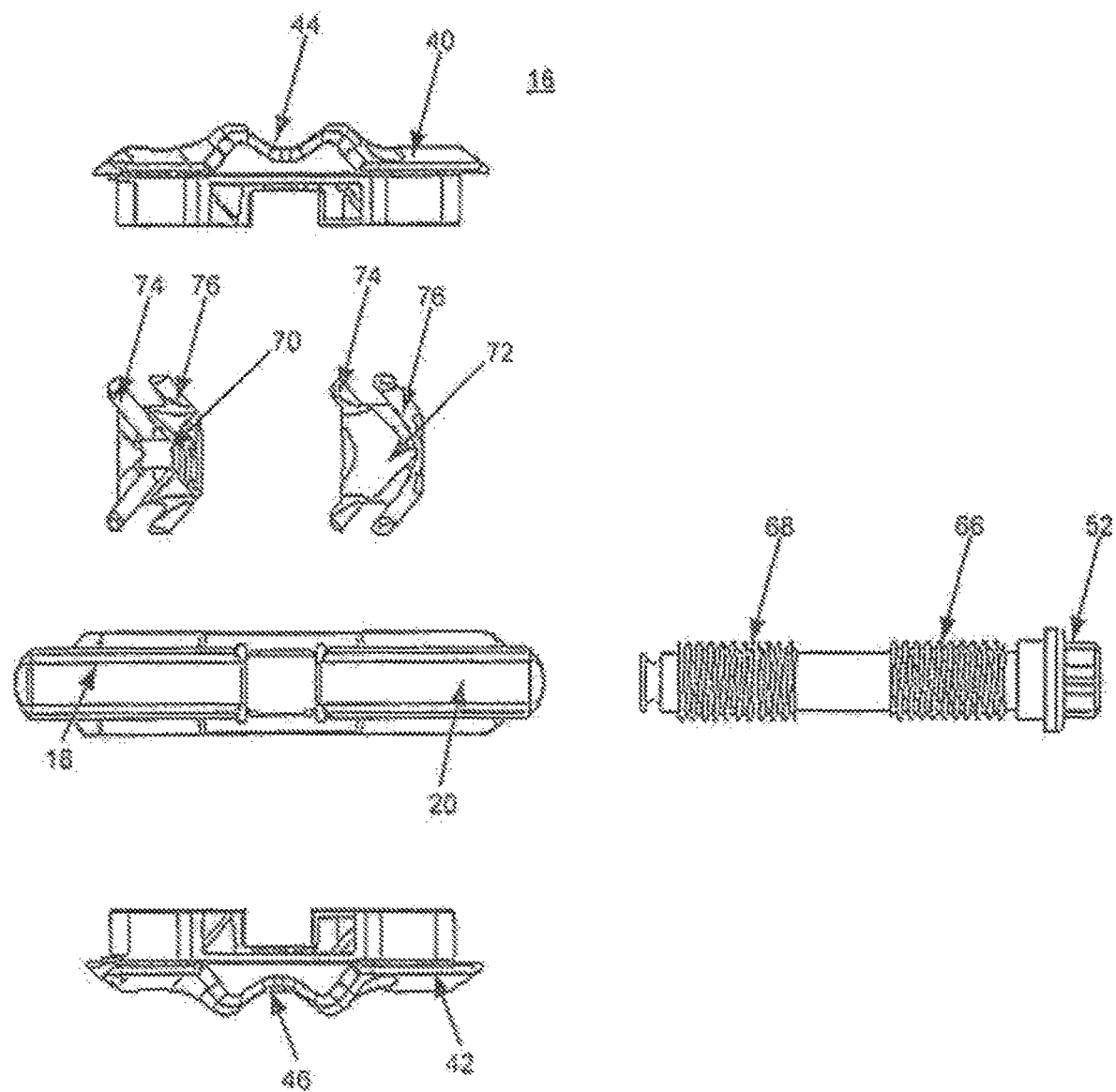
FIG. 29 is an exploded front view of a barrel of a medical device according to an example implementation.
Figure 31:
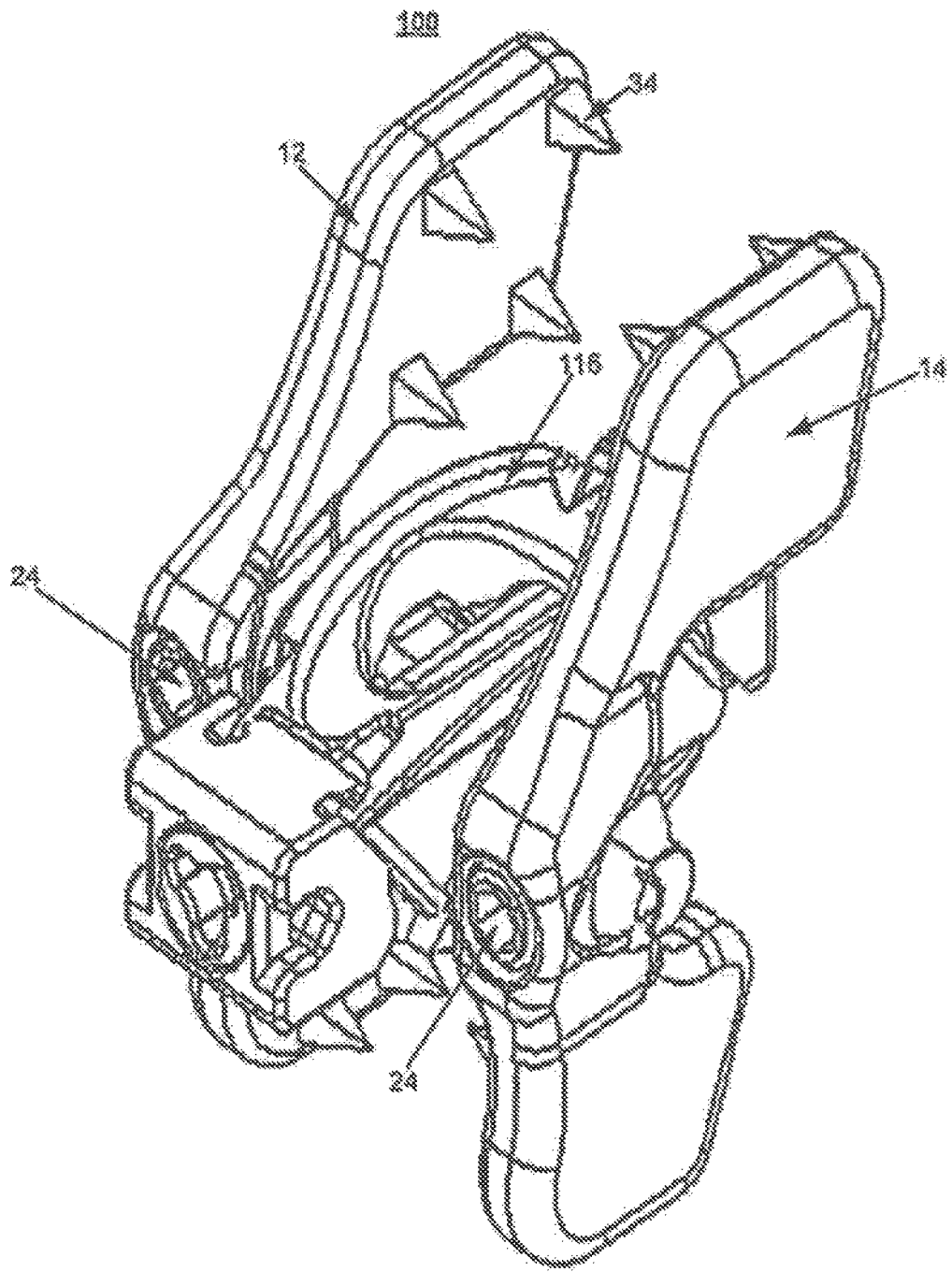
FIG. 31 is a perspective view of a medical device according to an example implementation.
Figure 32:
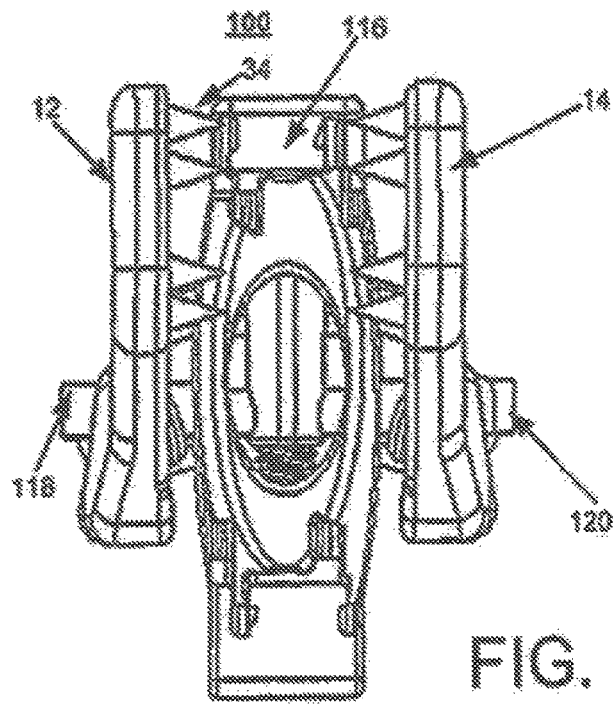
FIG. 32 is a top view of the medical device of FIG. 31.
Figure 33:
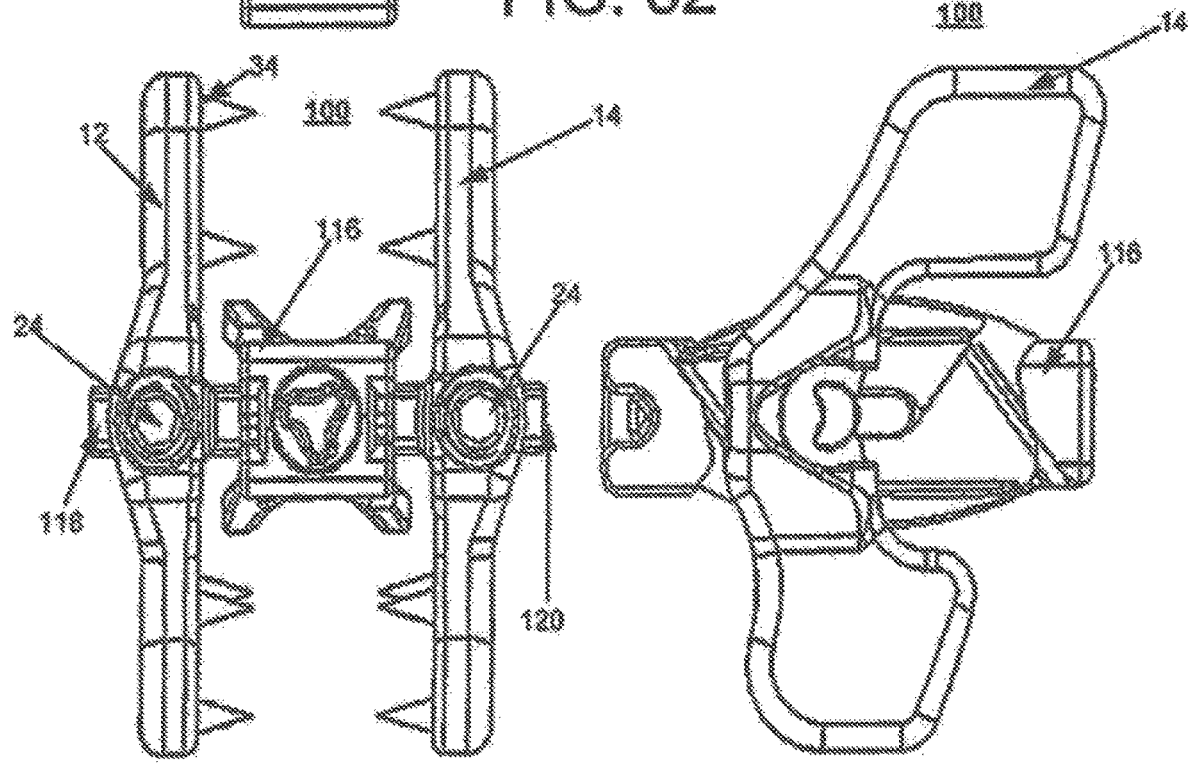
FIG. 33 is a front view of the medical device of FIG. 31.
Figure 34:
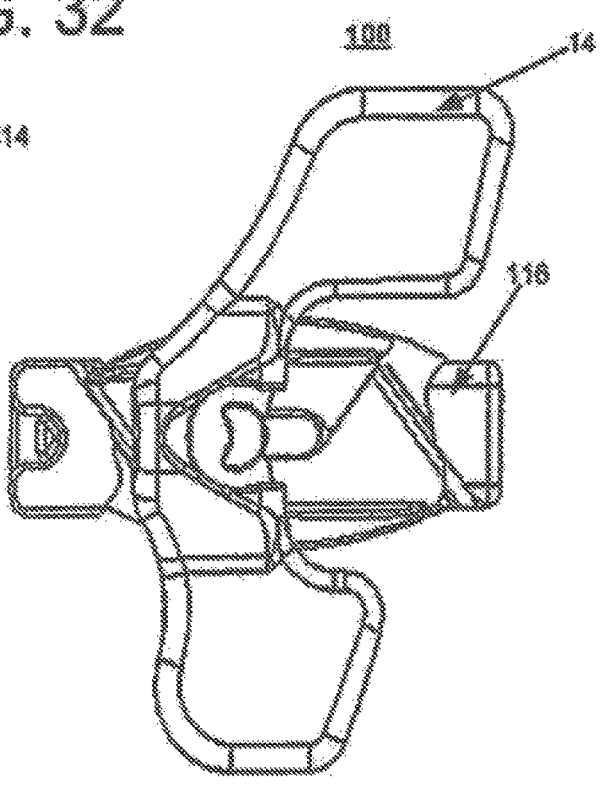
FIG. 34 is a side view of the medical device of FIG. 31.
Figure 35:
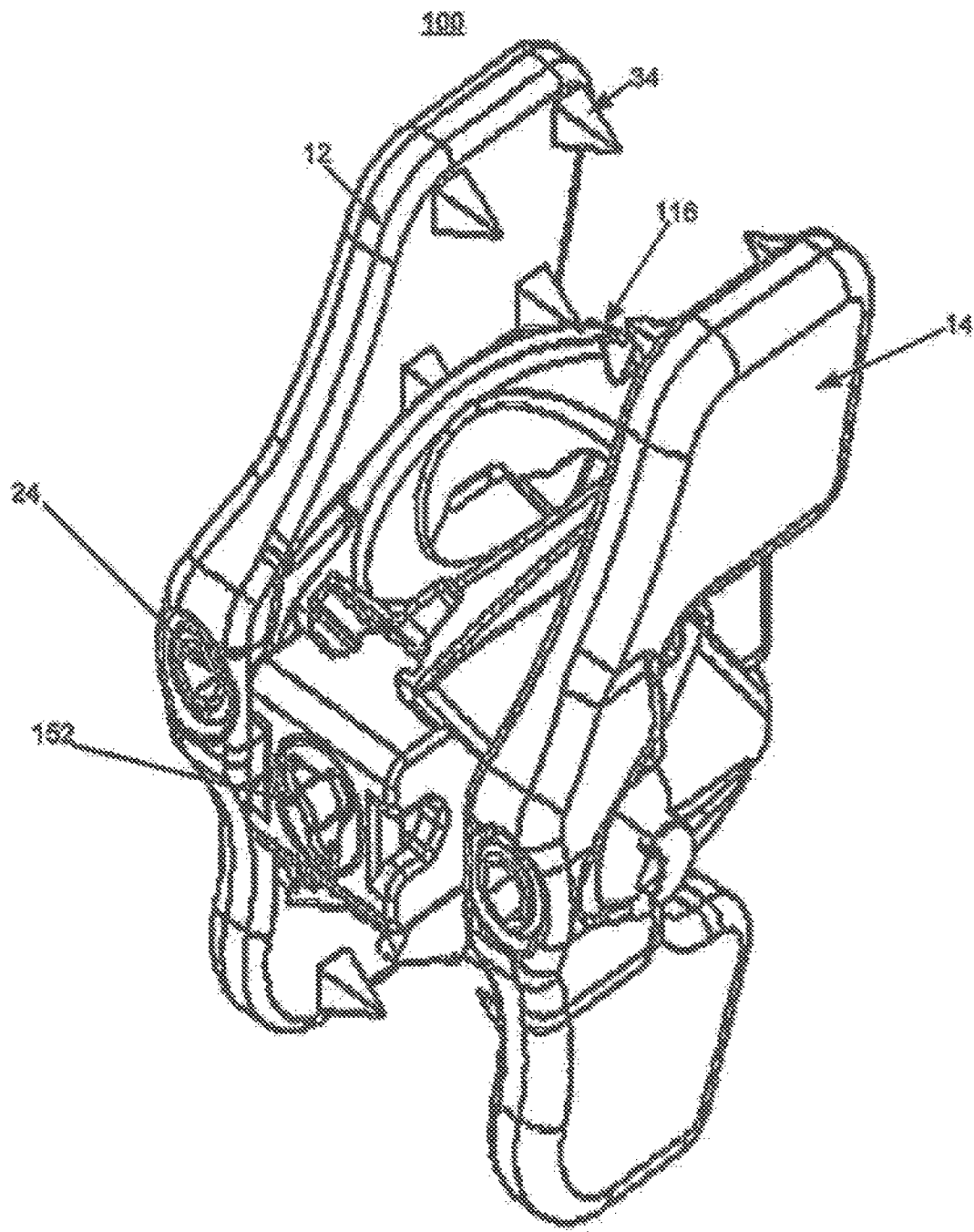
FIG. 35 is a perspective view of a medical device according to an example implementation.
Figure 39:
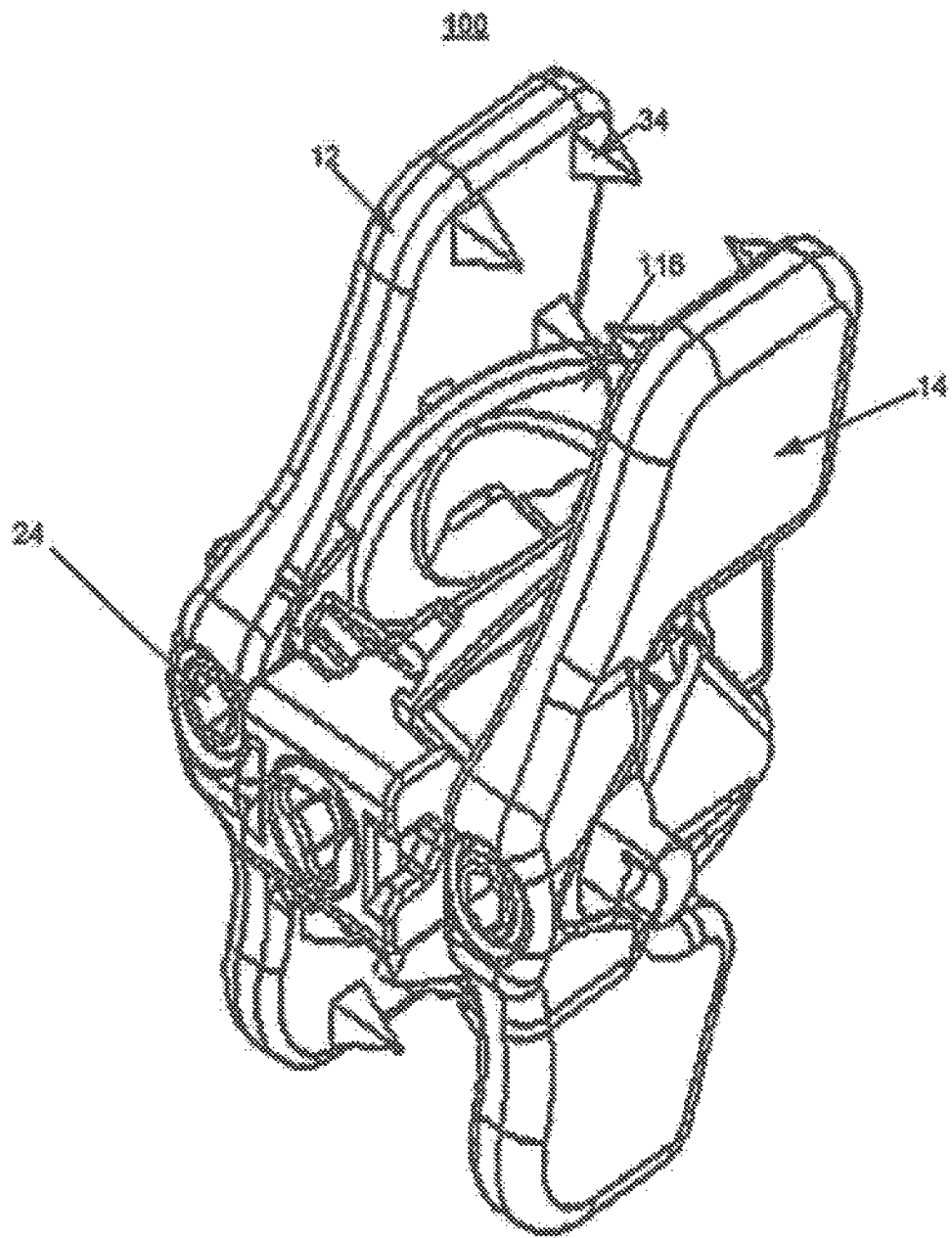
FIG. 39 is a perspective view of a medical device according to an example implementation.
Figure 40:
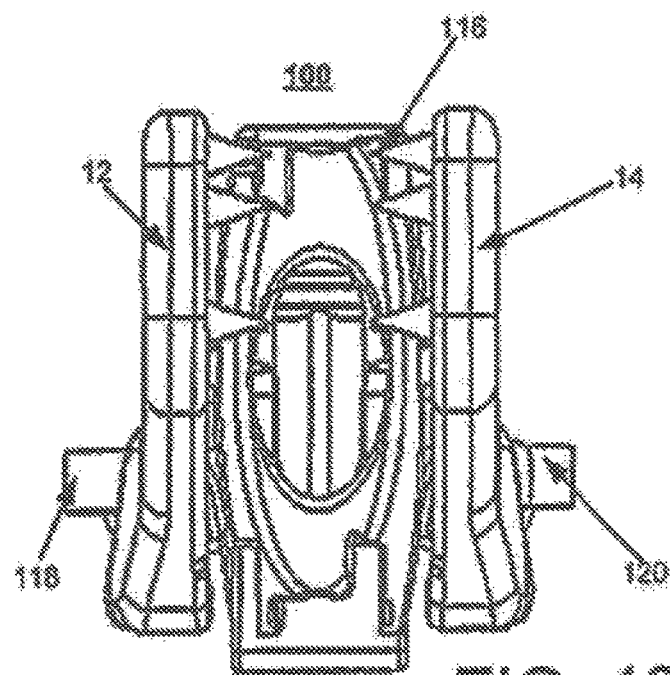
FIG. 40 is a top view of the medical device of FIG. 39.
Figure 41:
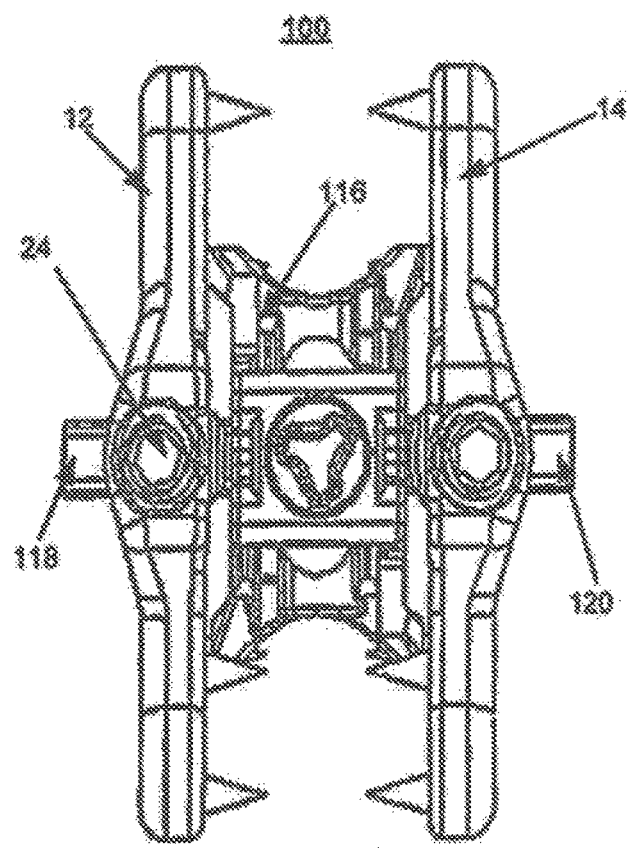
FIG. 41 is a front view of the medical device of FIG. 39.
Figure 42:
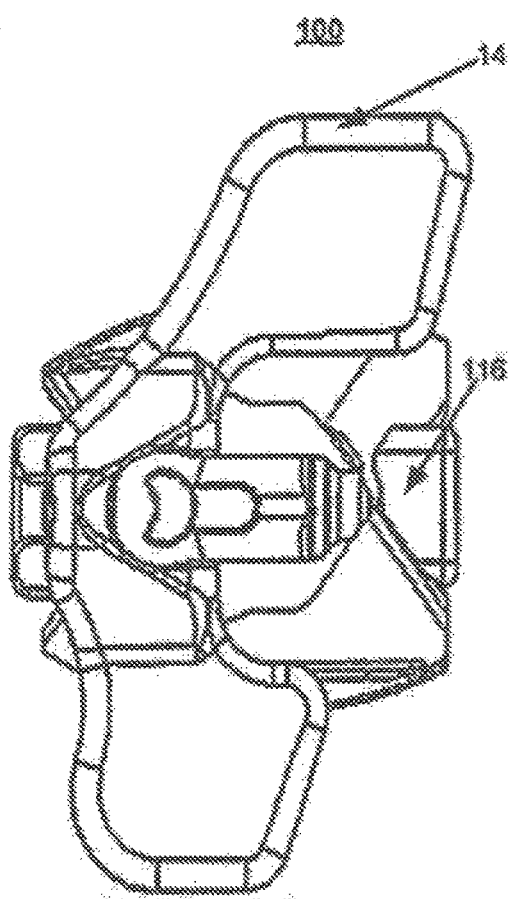
FIG. 42 is a side view of the medical device of FIG. 39.
Figure 43:
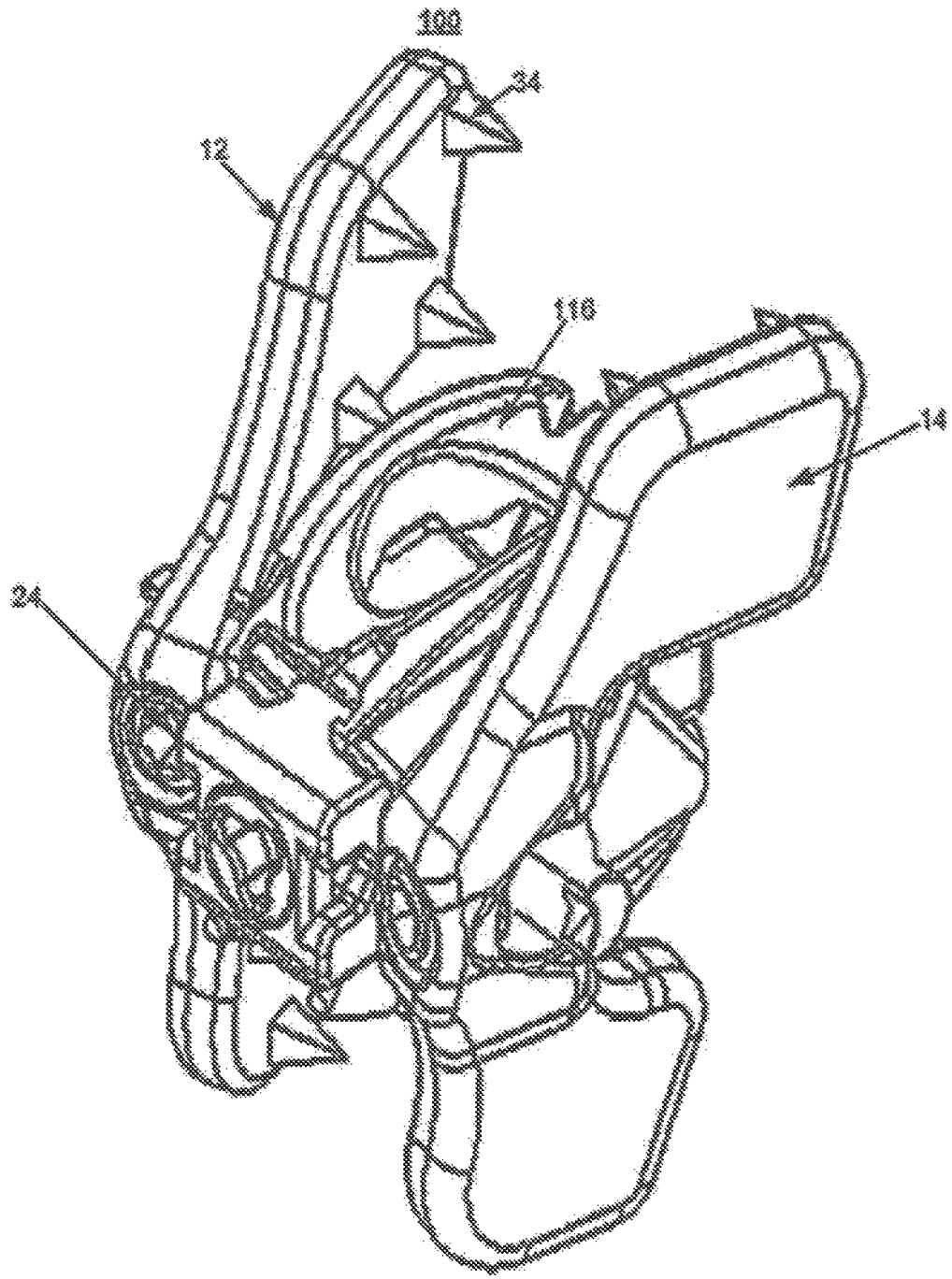
FIG. 43 is a perspective view of a medical device according to an example implementation.
Figure 44:
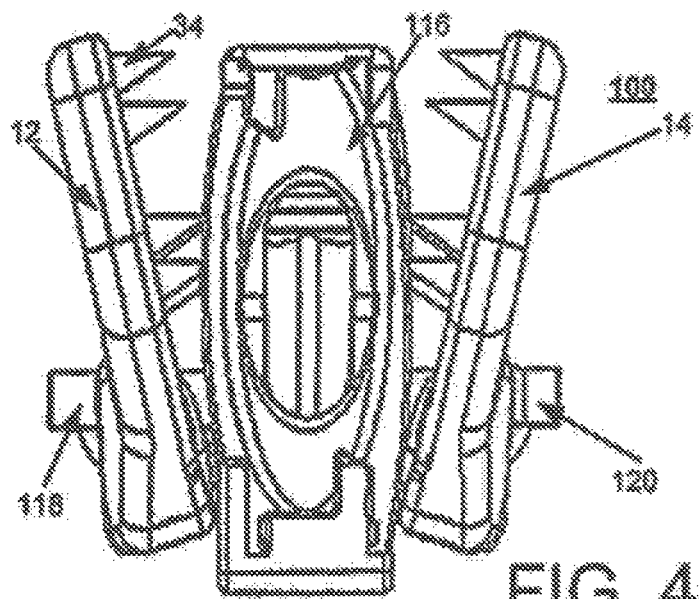
FIG. 44 is a top view of the medical device of FIG. 43.
Figure 45:
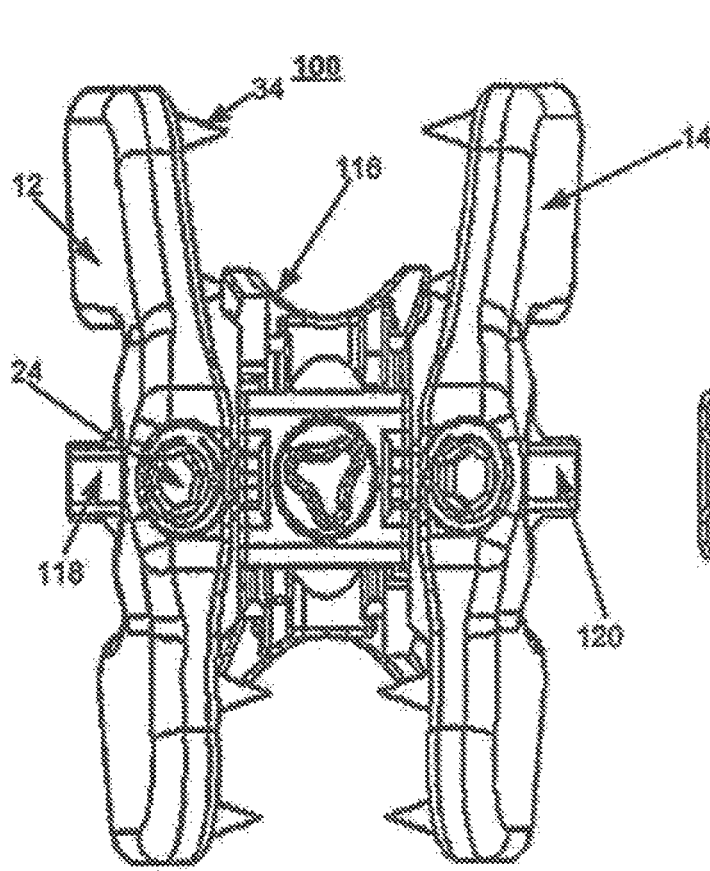
FIG. 45 is a front view of the medical device of FIG. 43.
Figure 46:
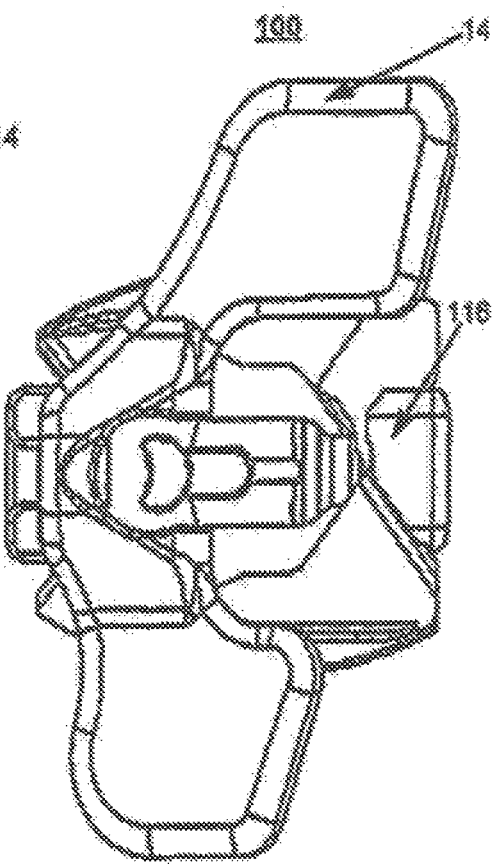
FIG. 46 is a side view of the medical device of FIG. 43.

Referring to FIGS. 28-30, the barrel 16 and assembly of the barrel 16 is illustrated in detail. As discussed above, the barrel 16 includes a first endplate 40 and a second endplate 42. The endplates 40 and 42 may be PEEK endplates. The barrel 16 includes a central screw 52 having a first thread portion 66 and a second thread portion 68. The barrel 16 includes a frame 65, a first actuator 70 and a second actuator 72 (also referred to as the actuators 70 and 72) and two assembly pins (not shown). In one example implementation, the frame 65, the actuators 70 and 72 and the central screw 52 may be made of titanium. In other example implementations, the components may be made of other biocompatible materials.

Each of the actuators 70 and 72 may include split ramps 74 and 76 to accommodate the curved shape of the barrel 16. The barrel 16 is curved shaped and may be bulleted (or egg-shaped) on each end to allow for easier insertion into the interspinous space. The curved shape of the barrel 16 may provide maximum graft packing volume.

The actuators 70 and 72 may be loosely assembled into the frame 65 of the barrel 16 and the 74 and 76 placed over the actuators 70 and 72. The central screw 52 may be inserted into the actuators 70 and 72 and timed so that the actuators have specific spacing per rotation of the screw 52. Once the screw 52 is fully inserted, two pins (not shown) are pressed into the frame 65 posteriorly to capture the screw 52 to prevent its disassembly.

The rotation of the screw 52 causes the actuators 70 and 72 to rotate and the ramps 74 and 76 on the actuators 70 and 72 to push against the endplates 40 and 42, causing the endplates 40 and 42 to expand from a collapsed position. A counter rotation of the screw 52 causes the actuators 70 and 72 to rotate and the ramps 74 and 76 on the actuators 70 and 72 to recede from pushing against the endplates 40 and 42, causing the endplates 40 and 42 to collapses from an expanded state.

FIGS. 31-34 illustrate a medical device 100 according to an example implementation. Similarly to the medical device 10, the medical device 100 may be implanted in a patient and referred to as a spinous process fusion device. Like reference numbers between the FIGS. 1-30 and FIGS. 31-34, and other figures below describing medical device 100, refer to the same or similar components and features between the two medical devices. The medical device 100 may have the same features and functionality as the medical device 10.

The medical device 100 includes a first plate 12 and a second plate 14. The medical device 100 includes a barrel 116. In the example of FIGS. 31-34, the barrel 116 includes rails 118 and 120 that each extend from a different side of the barrel 116 instead of extending from a same side like the rails 18 and 20 from the barrel 16 in medical device 10. The barrel 116 is essentially rotated 90 degrees compared to the barrel 16. In other aspects, the barrel 116 is an expandable barrel and has the same functionality as the barrel 16. The barrel 116 may be inserted laterally into a patient in the interspinous space. The barrel 116 may be inserted at a smaller height (or in a collapsed state) and then expanded to provide distraction and to eliminate the forces on the spinous process and frustration for the surgeon.

In FIGS. 31-34, the medical device 100 illustrates the plates 12 and 14 in an open state and the barrel 116 in a collapsed state. In this manner, the medical device 100 may inserted into a patient and then the barrel 116 expanded.

Referring to FIGS. 35-38, the medical device 100 is illustrated with the barrel 116 in an expanded state. In one example implementation, the expanded barrel height for the barrel 116 may be about 7 mm greater than the collapsed height. The sides 12 and 14 are illustrated in an open state. The barrel 116 may be expanded from a collapsed state to an expanded state using the central screw 152. Similarly, the barrel 116 may be collapsed from an expanded state to a collapsed state using the central screw 152.

Referring to FIGS. 39-42, the medical device 100 is illustrated with the barrel 116 in an expanded state and the plates 12 and 14 in a closed position. As discussed above with respect to the medical device 10, the plates 12 and 14 on the medical device 100 also may traverse the rails 118 and 120 of the barrel between an open position and a closed position. In the closed position, the plates 12 and 14 are designed to clamp and bite into the spinous process, as discussed above in detail.

Referring to FIGS. 43-46, the medical device 100 is illustrated with the barrel 116 in an expanded state and the plates 12 and 14 in a closed and angulated position. As discussed above with respect to FIGS. 17-20, the plates 12 and 14 may angulate about 25 degrees with respect to the rails 118 and 120 to better conform to patient anatomy. The plates 12 and 14 may be locked in position using the set screw 24.

Figure 47:
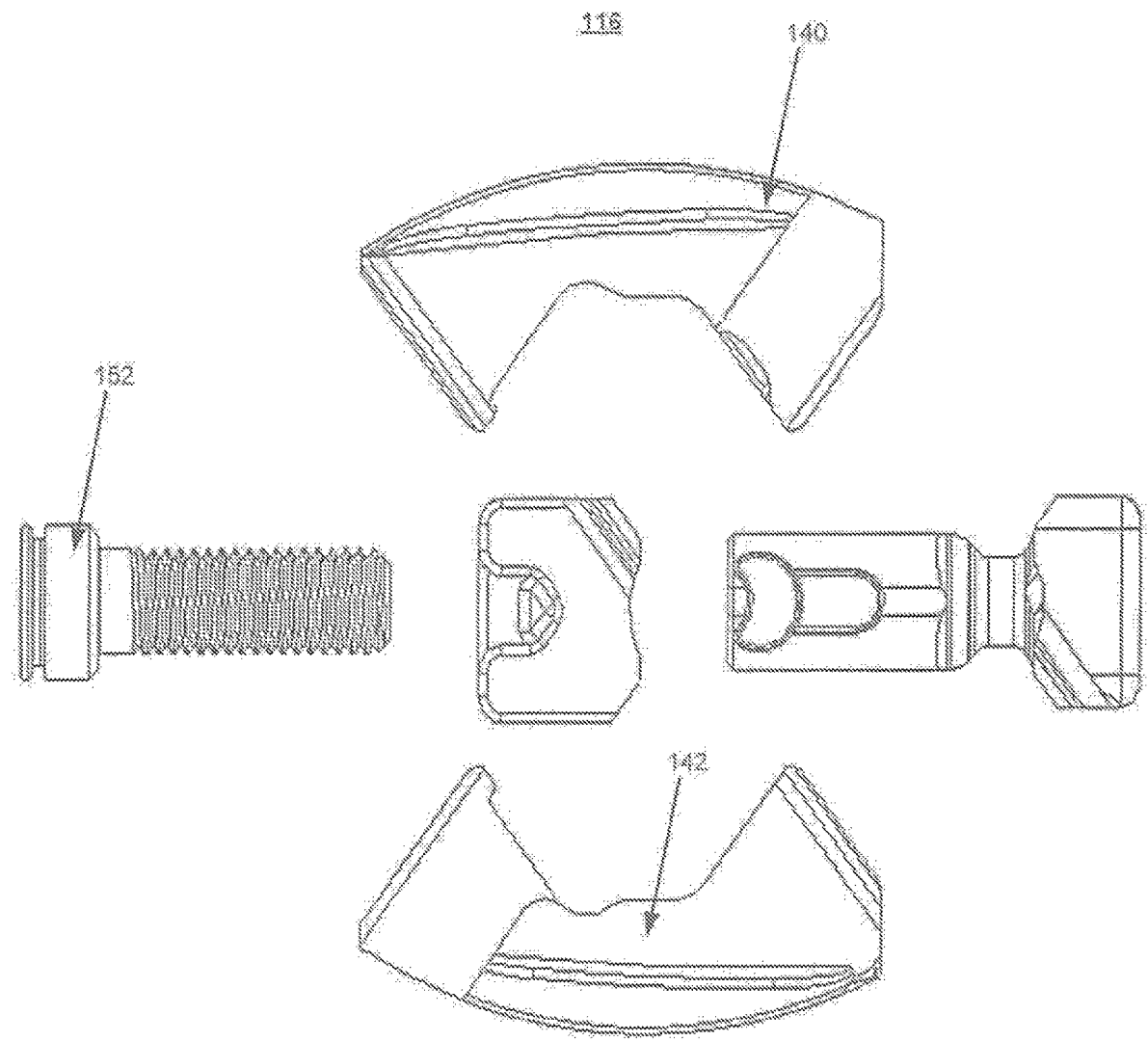
FIG. 47 is an exploded top view of a barrel of a medical device according to an example implementation.

Referring to FIG. 47, the barrel 116 is assembled in a manner similar to the barrel 16, as discussed above with respect to FIGS. 28-30. The barrel 116 includes a first endplate 140 and a second endplate 142, two independent actuators with ramps and a central screw 152. The endplates 140 and 142 are loosely assembled into the actuator ramps and the central screw 152 is inserted into the actuator ramps, which anchor the assembly together.

Figure 48:
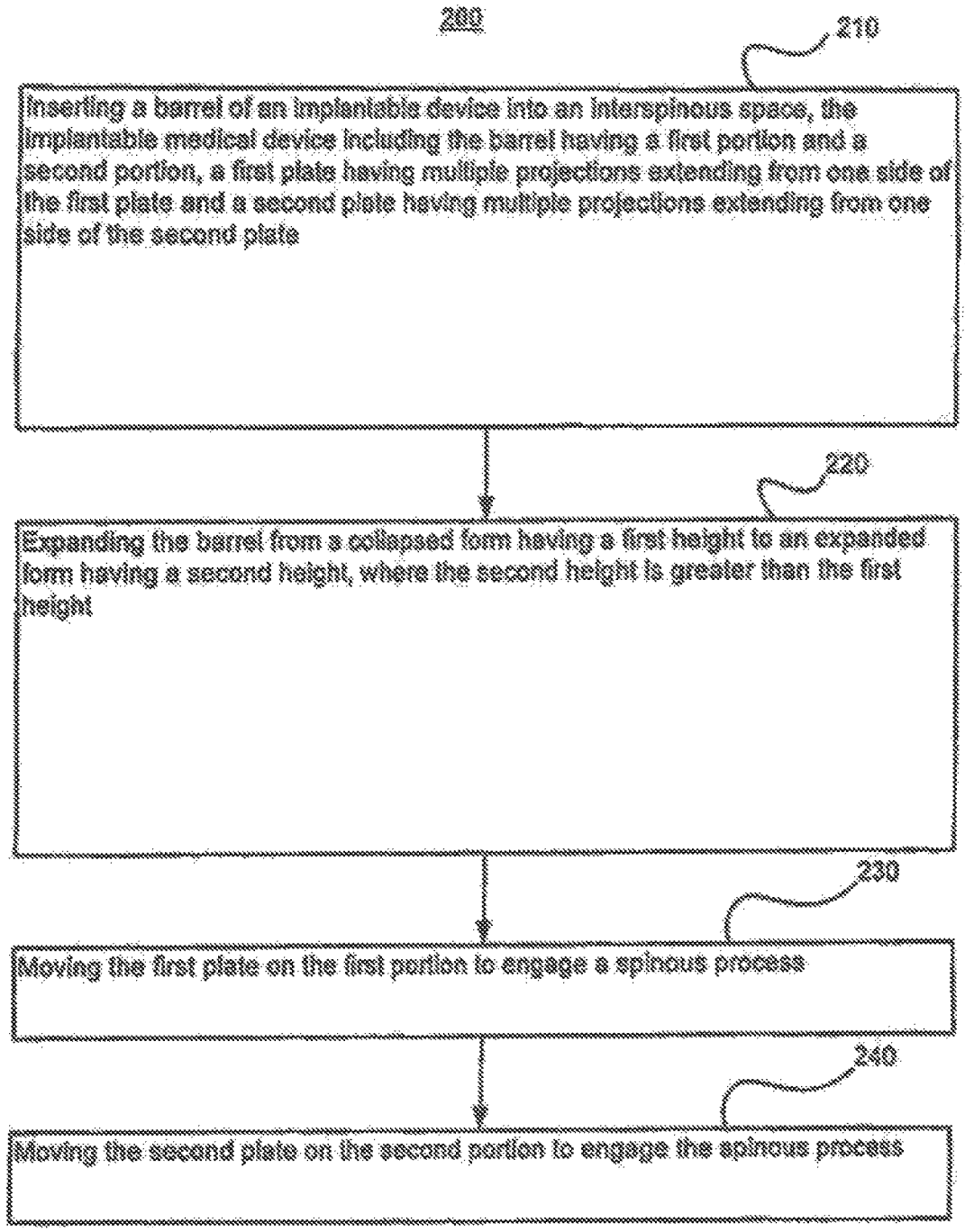
FIG. 48 is a flow chart illustrating an exemplary method including the medical device of FIG. 1.

Referring to FIG. 48, an example flowchart illustrates an example process 200 for using the medical devices 10 and 100. For example, process 200 includes inserting a barrel 16 or 116 of the medical device 10 or 100, respectively, into an interspinous space (210). As discussed above, the medical device includes the barrel 16 or 116 having a first portion (e.g., rail 18 or 118) and a second portion (e.g., rail 20 or 120), a first plate 12 having multiple projections 34 extending from one side of the first plate 12 and a second plate 14 having multiple projections 34 extending from one side of the second plate (210).

The process 200 includes expanding the barrel 16 or 116 from a collapsed form having a first height to an expanded form having a second height, where the second height is greater than the first height (220). As discussed above, the central screw 52 or 152 may be rotated to expand the barrel 16 or 116 from a collapsed form to an expanded form in the interspinous space.

The process includes moving the first plate 12 on the first portion (e.g., rail 18 or 118) to engage a spinous process (230) and moving the second plate 14 on the second portion (e.g., rail 20 or 120) to engage the spinous process (240). For example, the projections 34 on each of the plates 12 and 14 may engage the spinous process of adjacent vertebrae as the plates 12 and 14 are slid along the respective rails.

Optionally, the process 200 may include positioning the first plate 12 to a desired angle with respect to the first portion and positioning the second plate 14 to a desired angle with respect to the second portion. Once the plates 12 and 14 have been positioned to their desired angles, the plates 12 and 14 may be locked into position using the set screws 24.

Figure 49:
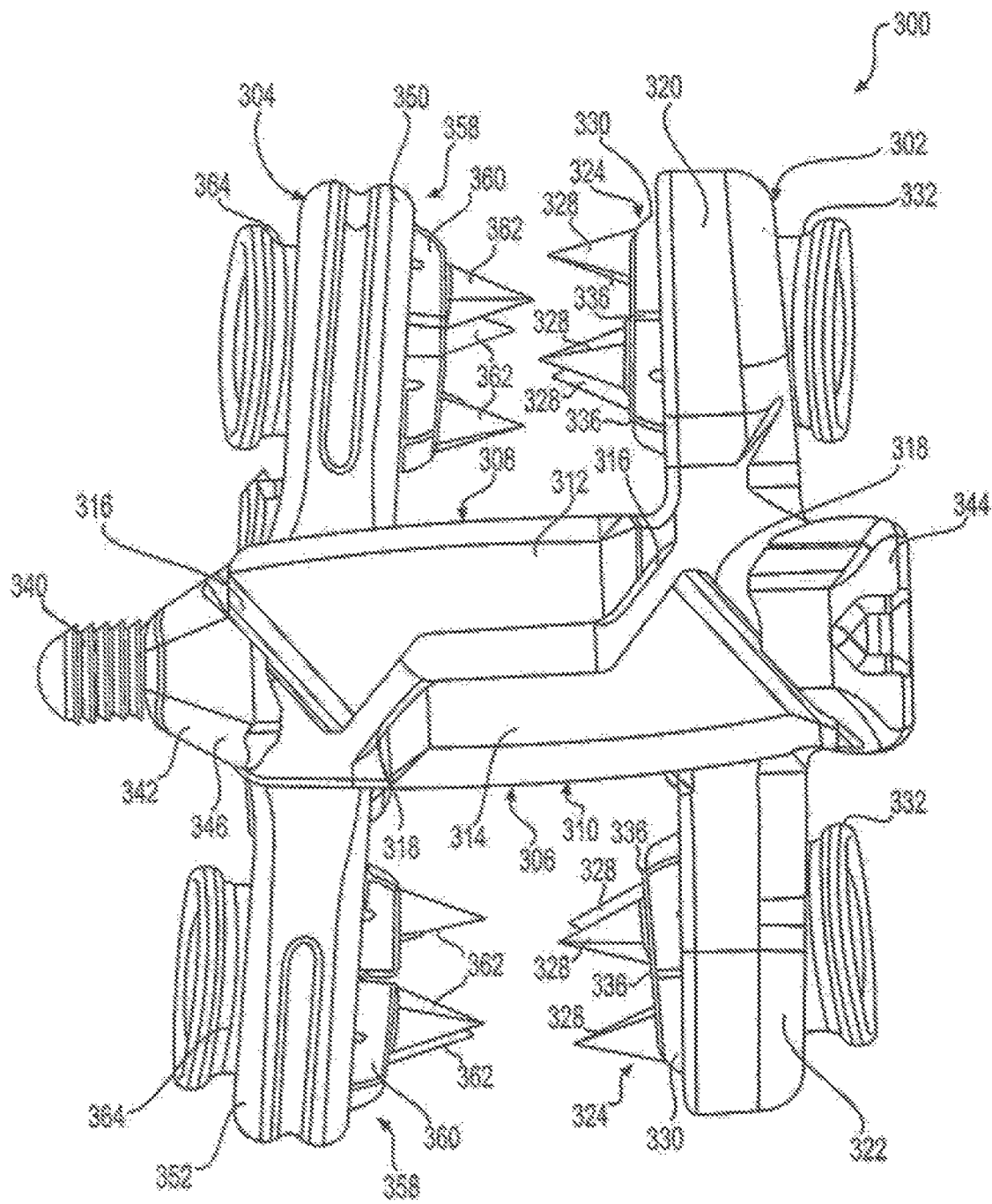
FIG. 49 is a perspective view of a medical device according to one implementation.
Figure 50:
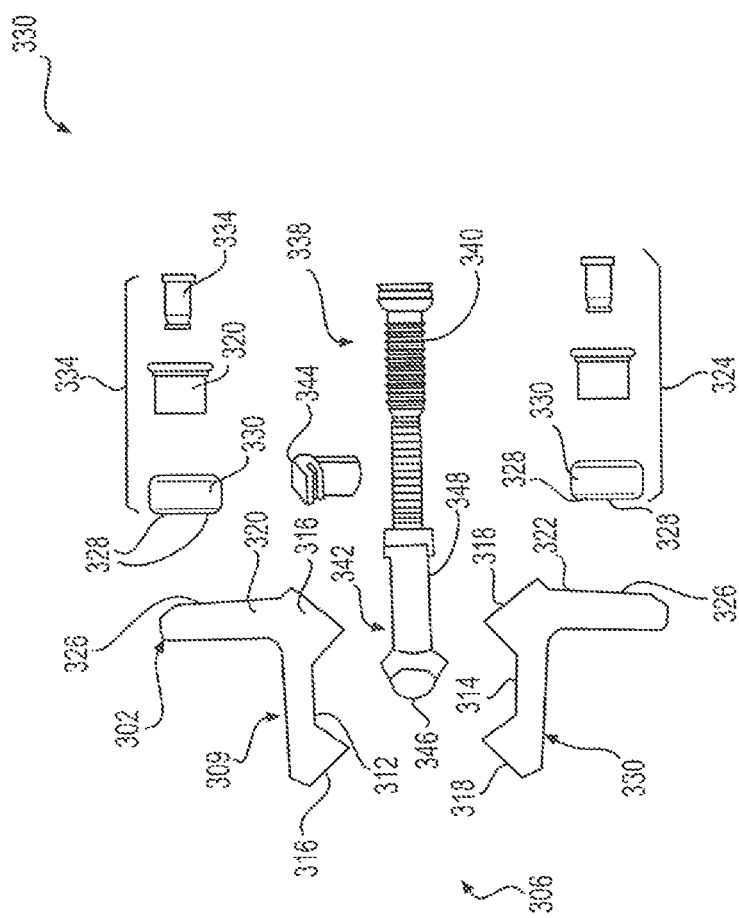
FIG. 50 is an exploded view of the medical device of FIG. 49 with the locking plate removed according to one implementation.

FIG. 49 illustrates a medical device 300 according to one example implementation. FIG. 49 is a perspective view of the medical device 300. The medical device 300 may be implanted into a patient and referred to as a spinous process fusion device. In the illustrated embodiment, the medical device 300 includes a first plate 302, a second plate 304 (e.g., locking plate 304), and an expandable central barrel (also referred to as a barrel) 306.

With additional reference to FIGS. 50-54, the medical device 300 of FIG. 49 will be described in more detail. FIGS. 50-54 illustrate an exploded view, side view, front view, rear view, and top view, respectively, of the medical device 300, which illustrate the barrel 306 in the collapsed or contracted position with the locking plate 304 removed. The barrel 306 may be inserted into the interspinous space without the locking plate 304 and then expanded. The locking plate 304 may then be attached to the barrel 306 after insertion to the lock the medical device 300 in place in engagement with the spinous process.

Figure 51:
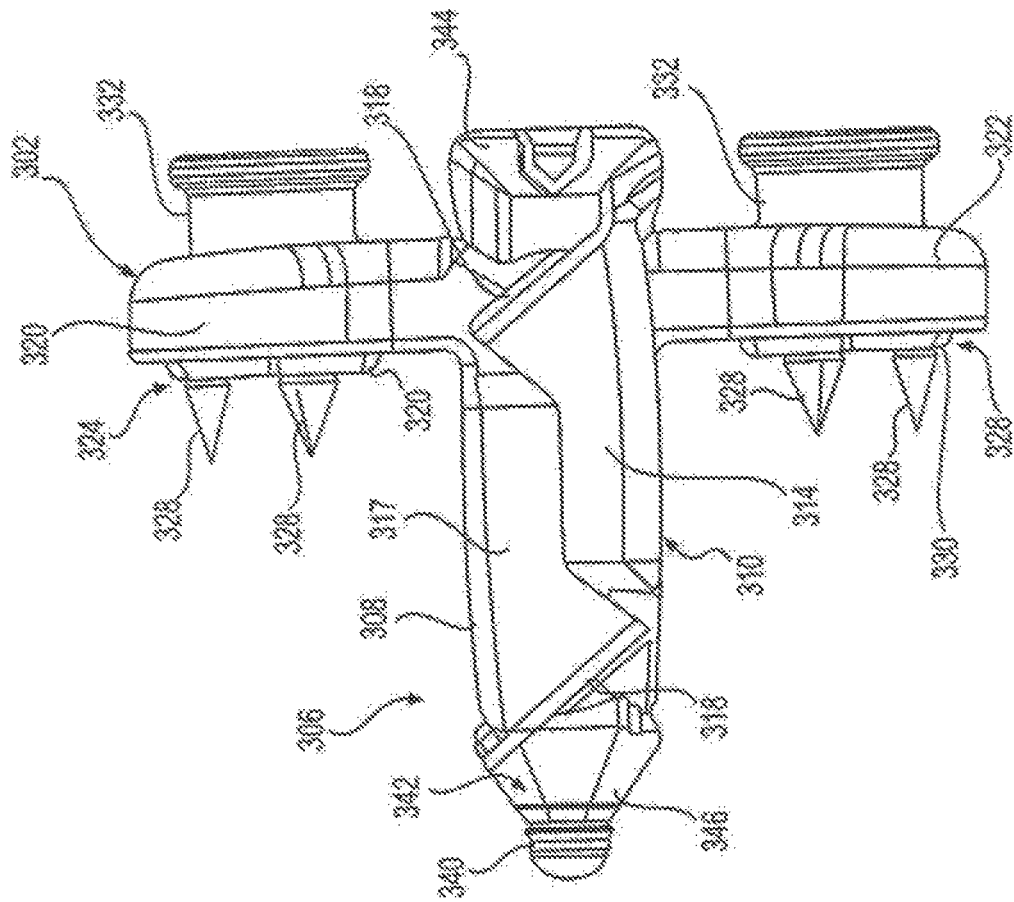
FIG. 51 is a side view of the medical device of FIG. 50.
Figure 52:
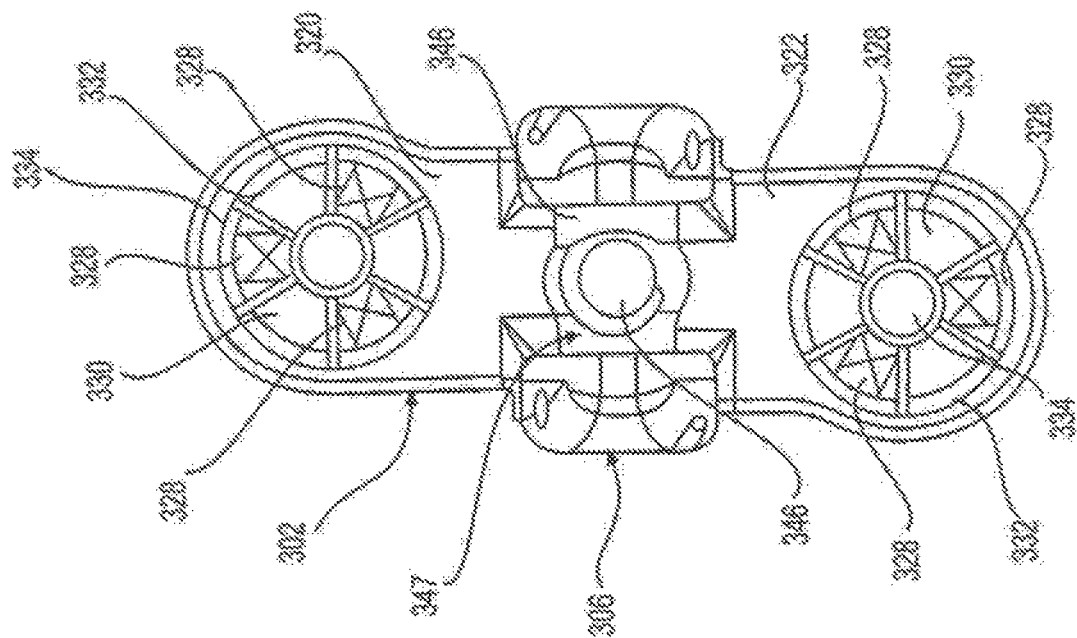
FIG. 52 is a front view of the medical device of FIG. 50.
Figure 55:
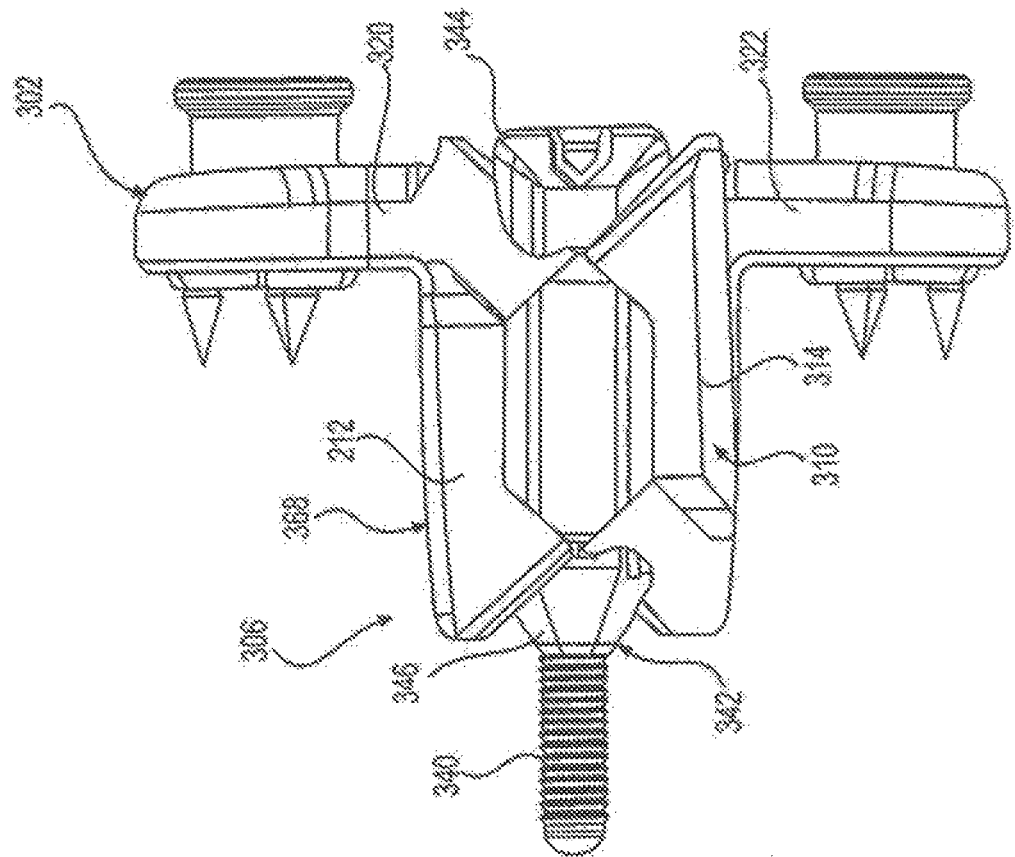
FIG. 55 is a side view of the medical device of FIG. 49 with the locking plate removed according to one example implementation.

Win the illustrated embodiment, the barrel 306 includes a first portion 308 (e.g., upper portion 308) and a second portion 310 (e.g., lower portion 310). The first portion 308 may include a pair of ramped upper sidewalls 312. The ramped upper sidewalls 312 may include ramped portions 316 on either end of the ramped sidewalls 314. The second portion 312 may also include a pair of ramped lower sidewalls 314. The ramped lower sidewalls 314 may include ramped portions 318 on either end. As best seen in FIG. 51, the ramped lower sidewalls 314 and the ramped upper sidewalls 312 may overlap when the medical device 10 is collapsed. The ramped upper sidewalls 312 and the ramped lower sidewalls 314 may define a central chamber in the barrel 306. The central chamber 315 may be used for the packing of bone graft material following the insertion and placement of the medical device 10 in a patient. In one implementation, after the barrel 306 has been expanded, the barrel 306 may be packed with bone graft using the central chamber 315. In this manner, the central chamber 315 may provide for a larger grafting area and may be packed after expansion of the barrel 306.

The central barrel 306 is an expandable barrel that may be in a collapsed position for insertion into a patient in the interspinous space without resistance and then expanded up to the barrel's maximum height. In one example implementation, the maximum expanded height of the barrel may be about 4 mm greater than the collapsed height or, alternatively, about 6 mm greater than the collapsed height. The central barrel 306 may provide interspinous distraction and may offload the forces of the spikes 328, 362 on the plates 302 and 304 to reduce the chances of breaking a spinous process. The barrel 306 may be inserted, laterally or posteriorly, in a smaller height and then expanded to provide distraction, eliminating forces on the spinous process and potential frustration for a surgeon performing the implantation.

The first plate 302 may include an upper portion 320 and a lower portion 322. The upper portion 320 of the first plate 302 may extend generally vertically from the first portion 308 of the barrel 306. The upper portion 320 may be integrally formed with the first portion 308. The lower portion 322 of the first plate 302 may extend from the second portion 310 of the barrel 306 in a direction generally opposite to the upper portion 320. The lower portion 322 may be integrally formed with the second portion 310. The first plate 302 may be shaped in a lordotic profile to match the lumbar anatomy.

The first plate 302 may include a spike assembly 324 on both the upper portion 320 and the lower portion 322. The spike assemblies 324 may each be received within an opening 326 in both the upper portion 320 and the lower portion 322. Each spike assembly 324 may include multiple projections (e.g., spikes 328) that extend from a spike sphere 330. The spike spheres 330 may each be a complete sphere, hemisphere, or a spheric section. Each spike assembly 324 may further comprise a wedge 332 and a post 334. The wedge 332 may be secured onto the post 334 with the spike sphere 330 fit onto the wedge 332 over the post 334. A pin (not shown) may be used in the opening 326 to prevent rotation of the spike sphere 330 in the opening 326 while allowing articulation of the spike sphere 330 with respect to the first plate 302. Slots 336 may be disposed in the spike sphere 330, as best seen on FIG. 49.

While the term "spikes" may be used for the projections other types of projections may be used that may have a more tapered point or rounded point or other type of ending to the projection. The spikes 328 may be used to attach firmly and bite into the spinous processes above and below an interspinous space. While spike assemblies 324 are shown, other embodiments may include spikes 328 that are integrally formed with the first plate 302. The spikes 328 may be pyramid shaped with a base portion secured or integrally formed on the spike sphere 330. The sides of the spikes 328 may extend from the base to form a point in the shape of a pyramid. In other example implementations, the spikes 328 may be formed into other shapes that rise to a point to enable the spike to engage the spinous process. As discussed above, the end of the spikes 328 may include tips other than a point such as, for example, rounded tip, a square tip or other-shaped tip. The example illustration of the medical device 10 includes three (3) spikes 328 on each spike assembly 324 of the first plate 302. In other example implementations, fewer or more spikes 328 may be included. The first plate 302 and the spikes 328 may be made of titanium. In other implementations, the first plate 302 and the spikes 328 may be made of other biocompatible materials.

The medical device 10 may further include an actuator assembly 338 (best seen on FIG. 50) for raising and lowering the first and second portions 308 and 310 of the barrel 306 and, thus, the upper and lower portions 320, 322 of the first plate 302. The actuator assembly 338 may be disposed between the first and second portions 308 and 310 of the barrel 306. As illustrated, the actuator assembly 338 may comprise a central screw 340, a front ramped actuator 342 and a rear ramped actuator 344. The front ramped actuator 342 may be bullet shaped on its front end to facilitate insertion into a patient. The front ramped actuator 342 may have a ramped expansion portion 346 and an extension portion 348. The ramped expansion portion 346 may be located at a front end of the barrel 306 with the extension portion 348 extending from the ramped expansion portion 346 towards a rear end of the barrel 306. The central screw 340 may extend through the barrel 306 and engage the extension portion 348. The first and second portions 308 and 310 of the barrel 306 may slidingly engage the ramped expansion portion 346. For example, the ramped expansion portion 346 may engage ramped surface 316 of the first and second portions 308 and 310 at a front end of the barrel 306. The ramped expansion portion 346 may have dovetail connections with the first and second portions 308 and 310, respectively. The rear ramped actuator 344 may be disposed at a rear end of the barrel 306. The first and second portions 308 and 310 of the barrel 306 may slidingly engage the rear ramped actuator 344. For example, the rear ramped actuator 344 may also engage ramped surfaces 316 of the first and second portions 308 and 310 of the barrel. The rear ramped actuator 344 may have dovetail connections with the first and second portions 308 and 310, respectively. The central screw 340 may extend through the rear ramped actuator 344 to engage the extension portion 348.

Figure 56:
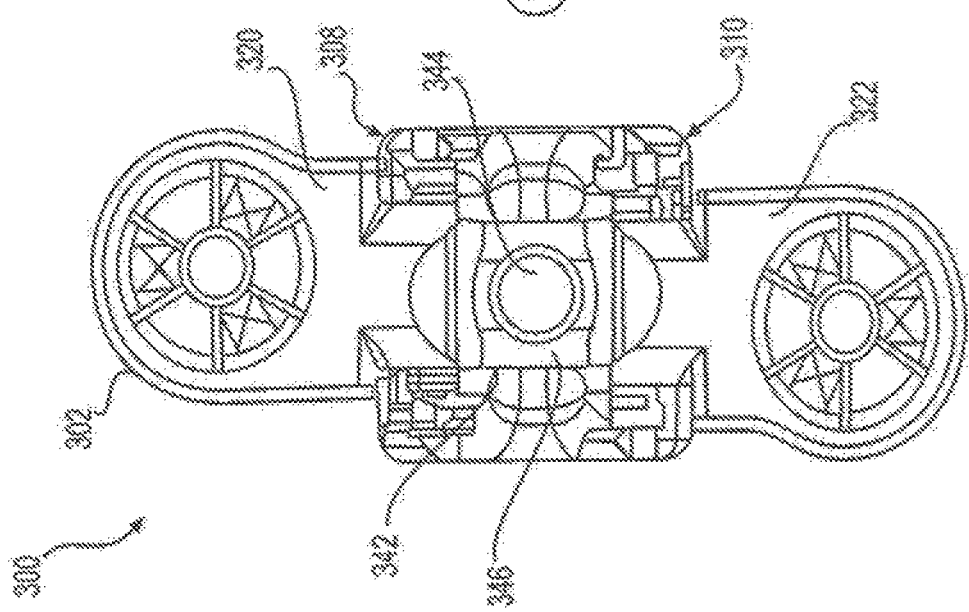
FIG. 56 is a front view of the medical device of FIG. 55.
Figure 57:
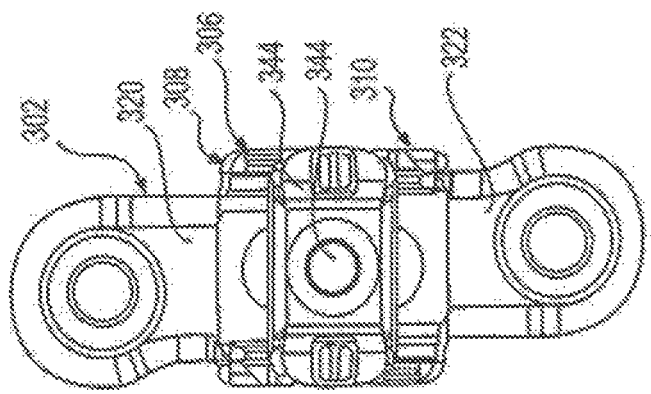
FIG. 57 is a rear view of the medical device of FIG. 55.
Figure 58:
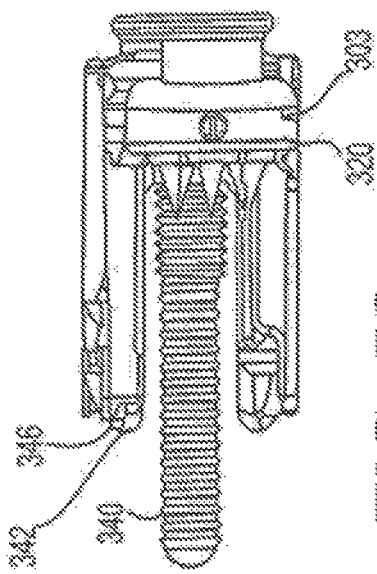
FIG. 58 is a top view of the medical device of FIG. 55.

Referring to FIGS. 56-58, an example implementation of the medical device of FIGS. 49-55 is illustrated with the barrel 306 shown in an expanded state. The barrel 306 expands by forcing the first and second portions 308 and 310 vertically outward in a direction away from one another. In this manner, the upper and lower portions 320 and 322 of the first plate 302 are also expanded vertically outward. The barrel 306 contracts by forcing the first and second portions 308 and 310 to contract in a direction toward one another, thus also moving the upper and lower portions 320 and 322 of the first plate 302 together. In some embodiments, the actuator assembly 338 may be used to raise and lower the first and second portions 308 and 310. By way of example, the central screw 340 may be turned to contract the actuator assembly 338. The rear ramped actuator 342 may be held in place while the central screw 340 is turned causing the front ramped actuator 340 to be drawn toward the rear ramped actuator 342. The rear ramped actuator 342 and the front ramped actuator 340 may engage the ramped upper sidewalls 312 and the ramped lower sidewalls 314 in the first and second portions 308 and 310 forcing the first and second portions 308 and 310 to expand from a collapsed position. A counter rotation of the central screw 340 may cause the front ramped actuator 340 and the rear ramped actuator 342 to separate causing the first and second portions 308 and 310 to collapse from the expanded state.

Figure 60:
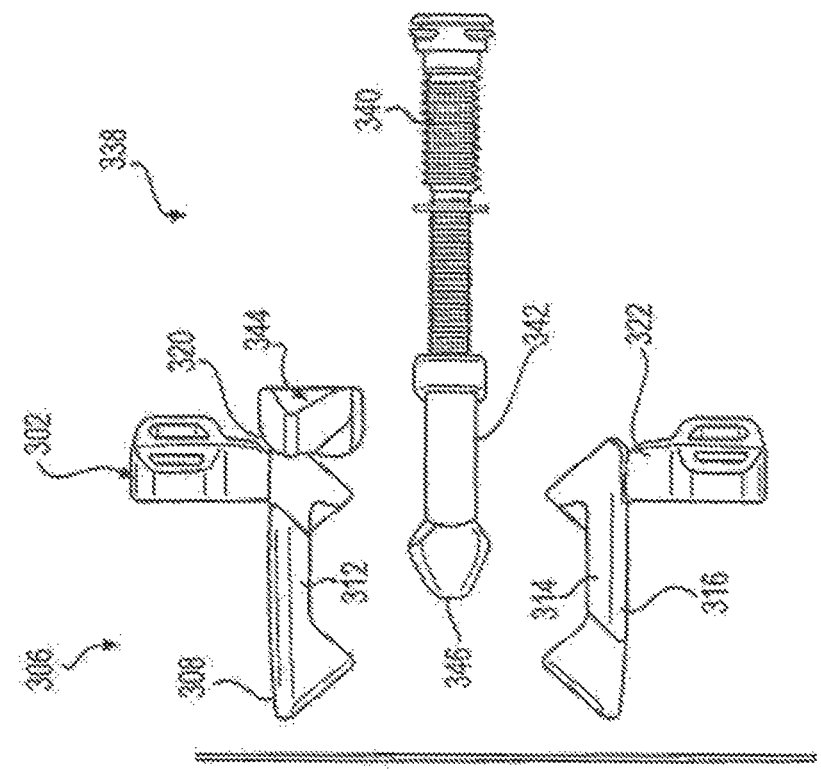
Figure 59:
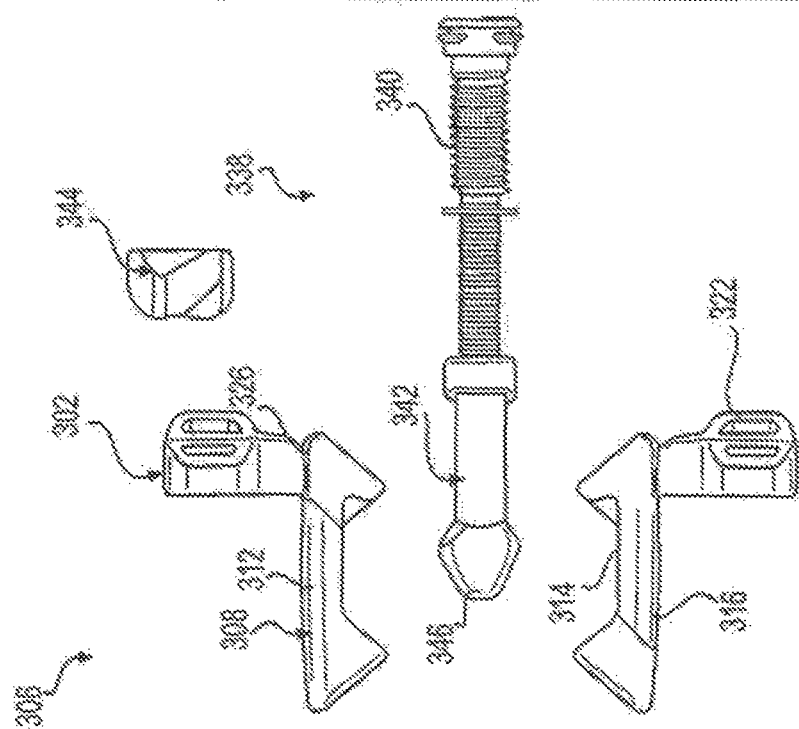

Referring to FIGS. 59-62, assembly of the barrel 306 of the medical device 300 shown on FIGS. 49-58 will now be described according to an example implementation. As illustrated by FIG. 59, the barrel 306 may comprise a first portion 308 and a second portion 310. The first plate 302 may be defined by upper portion 320 and lower portion 322. Upper portion 320 may extend from first portion 308 of the barrel 306, and lower portion 322 may extend in an opposite direction from second portion 310 of the barrel 306. As further illustrated by FIG. 59, the actuator assembly 338 may comprise a central screw 340, a front ramped actuator 342, and a rear ramped actuator 344. In FIG. 60, the rear ramped actuator 344 may be slid onto the first portion 308 of the barrel 306. As illustrated, the rear ramped actuator 344 may be engage (e.g., through a dovetail connection) a rear end of the upper ramped sidewalls 312 of the first portion 308. In FIG. 61, the front ramped actuator 342 may then the slide onto the second portion 310 of the barrel 306. As illustrated, the ramped expansion portion 346 may engage (e.g., through a dovetail connection) a front end of the lower ramped sidewalls 314 of the second portion 310. In FIG. 62, the first portion 308 and second portion 310 of the barrel 306 have been placed together in a contracted position with a front end of the upper ramped sidewalls 312 engaging the ramped expansion portion 346 and a rear end of the lower ramped sidewalls 314 engaging the rear ramped actuator 344.

Figure 65:
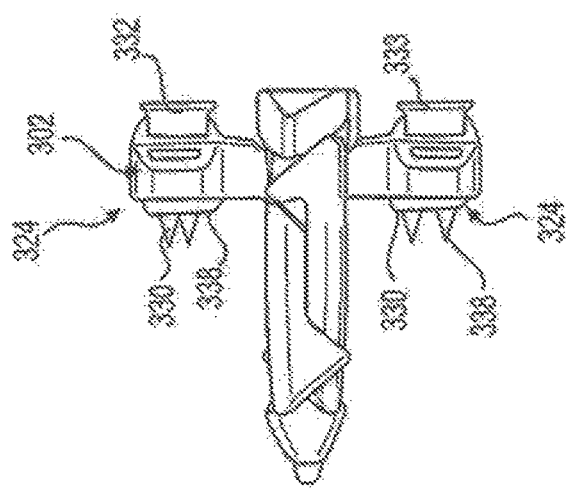
FIGS. 63-65 illustrate assembly of the spikes for the medical device of FIGS. 59-62.
Figure 64:
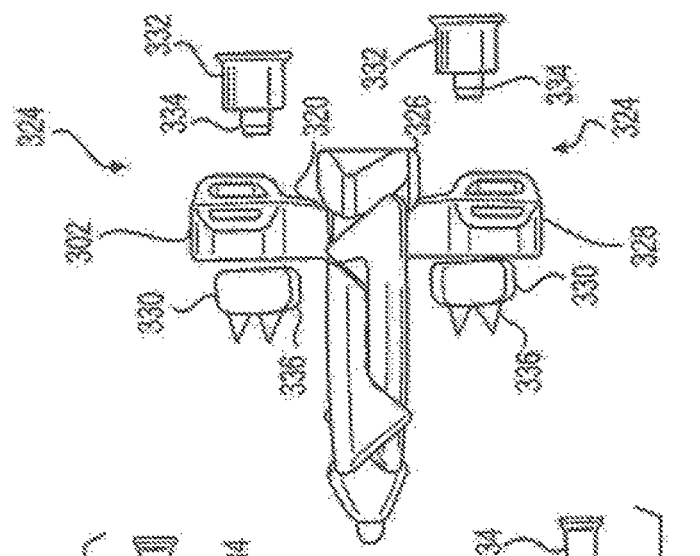
Figure 63:
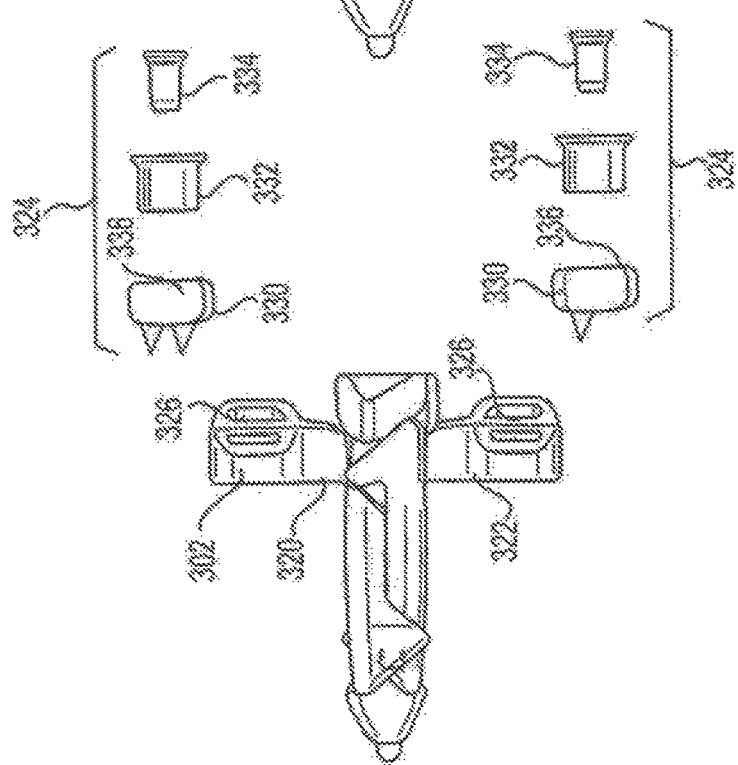

Referring to FIGS. 63-65, assembly of the spike assemblies 324 of the medical device 300 shown on FIGS. 49-58 will now be described according to an example implementation. As illustrated by FIG. 63, the spike assemblies 324 each comprise a spike sphere 330, a wedge 332, and a post 334. In FIG. 64, the post 334 may be inserted into the wedge 332 coupling the post 334 and the wedge 332. The wedge 332 may be secured onto one end of the post 334. Each assembly of the post 334 and wedge 332 may then be placed into the opening 326 in the upper and lower portions 320 and 322 of the first plate 302. The spike sphere 330 may then be placed onto the other end of the post 334, which may be then pressed back into the open 326, as seen in FIG. 65. In one embodiment, a snap connection may secure the spike sphere 330 the post 334. A pin (not shown) may be used in the opening 326 to prevent rotation of the spike sphere 330 assembly 324 in the opening 326 while allowing articulation of the spike sphere 330 with respect to the first plate 302. In some embodiments, slots 336 in the spike sphere 330 allow the spike sphere 330 to expand and collapse. To lock the spike sphere 330 in a particular orientation, the wedge 332 may be compressed further into the opening 326 causing the spike sphere 330 to expand outward and lock.

Figure 67:
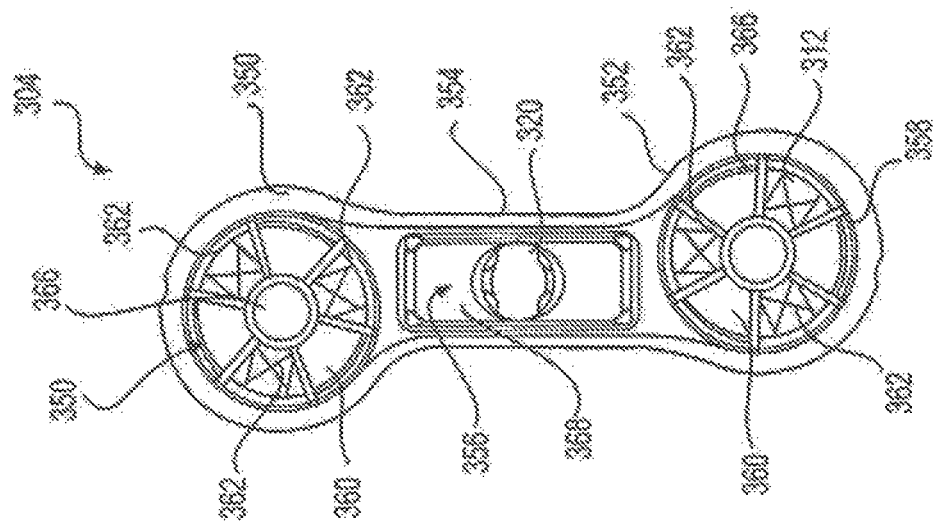
FIG. 67 is a front view of the locking plate of FIG. 66.
Figure 66:
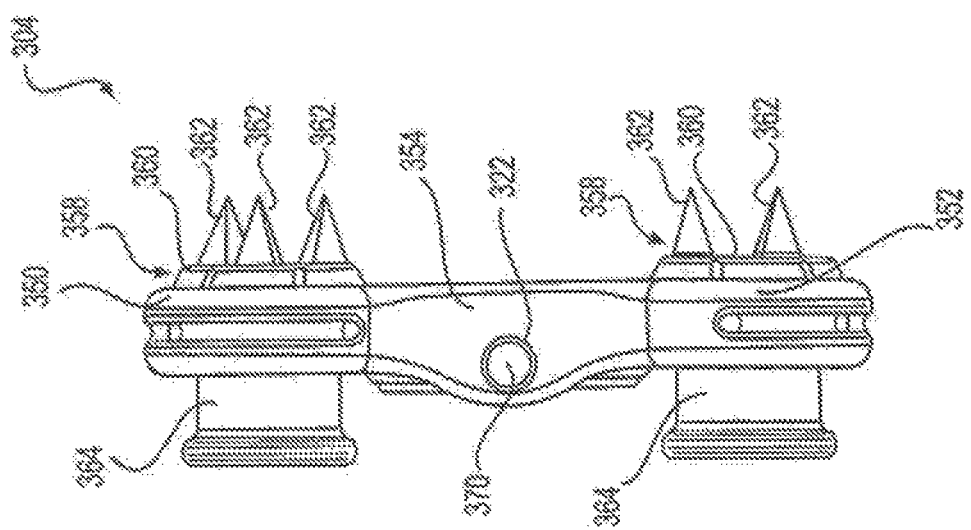
FIG. 66 is a side view of a locking plate for a medical device according to one example implementation.

Referring to FIGS. 49 and 66-67, the second or locking plate 304 will now be described in more detail with respect to one example implementation. FIG. 49 is a perspective view of the medical device 10 with the locking plate 304. FIGS. 66 and 67 are side and front views, respectively, of the locking plate 304. The locking plate 304 may be inserted onto the central screw 340 after the barrel 306 has been expanded to lock the barrel 306 in position.

As illustrated, the locking plate 304 may comprise an upper portion 350 and a lower portion 352. A central portion 354 may connection the upper portion 350 to the lower portion 352. The upper portion 350, lower portion 352, and central portion 354 may be integrally formed as a single plate component. The central portion 354 includes an opening (e.g., a central opening) to receive trunion assembly 356 (best seen on FIG. 67). The locking plate 304 may rotate about the trunion assembly 356 and can be locked at various angles at any position within its range of motion. In some embodiments, the trunion assembly 356 may be configured so that the locking plate 304 rotates about its center. The locking plate 304 may include a spike assembly 358 on both the upper portion 350 and the lower portion 352. The spike assemblies 358 may each be received within an opening in both the upper portion 350 and the lower portion 352 of the locking plate 304. Each spike assembly 358 may comprise a spike sphere 360 having multiple projections, such as spikes 362. Each spike assembly 358 may further comprise a wedge 364 and a post 366. The spike assemblies 358 and its various components may be similar in function and assembly to the spike assembly 324 of the first plate 302 discussed above with respect to FIGS. 49-58 and 63-65.

Figure 69:
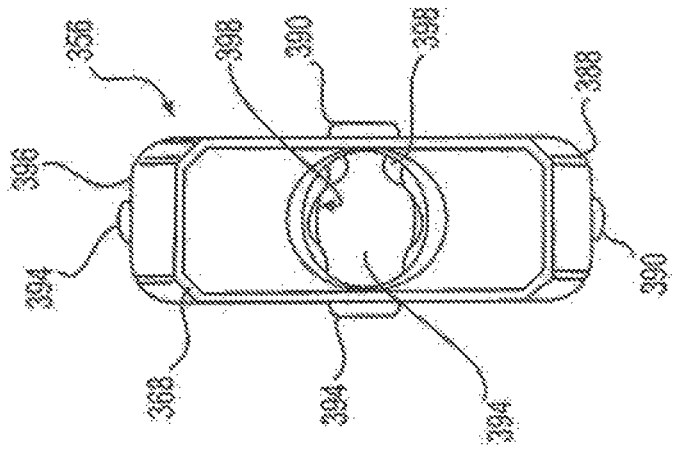
FIG. 69 is a front view of the trunion assembly of FIG. 68.
Figure 68:
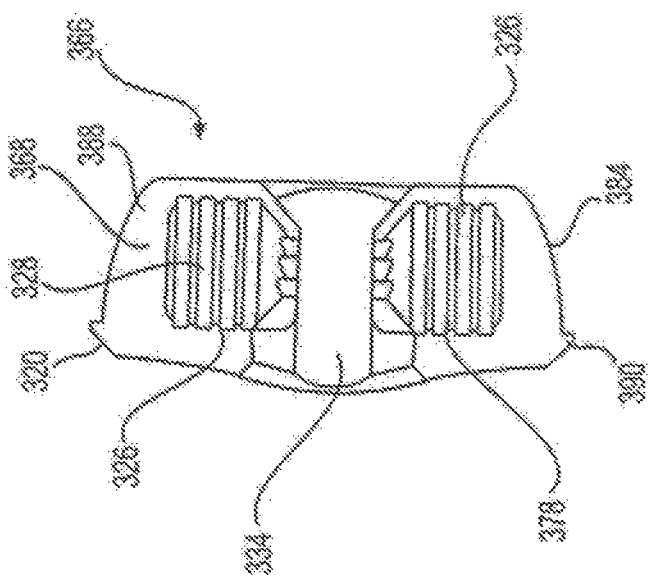
FIG. 68 is a cross-sectional view of a trunion assembly for a medical device according to one example implementation.
Figure 72:
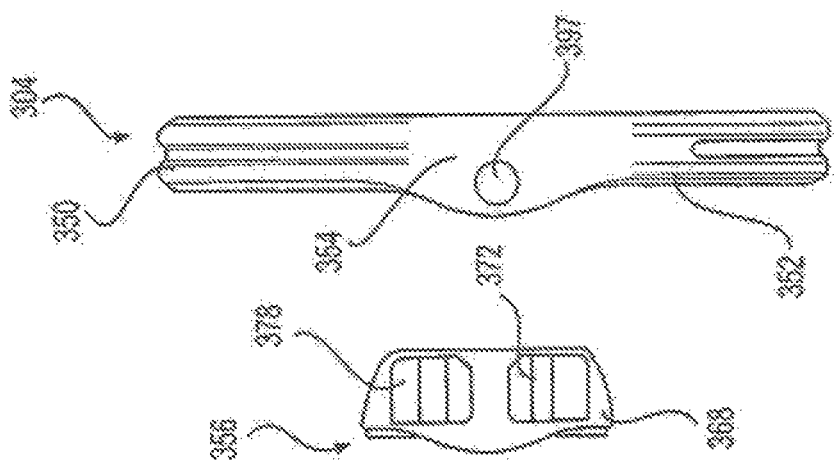

With additional reference to FIGS. 68 and 69, the trunion assembly 356 will described in more detail with respect to one example implementation. As illustrated, the trunion assembly 356 may comprise a housing 368. The housing 368 may have laterally extending projections 370 for rotatably coupling the trunion assembly 368 to the central portion 354 of the locking plate 304 while allowing the locking plate 304 to rotate with respect to the trunion assembly 368. As illustrated, there may be a pair of projections 370 that extend from opposite sides of the housing 368 and are each received in corresponding openings 372 in the central portion 354. The housing 368 may further have a through bore 374 for receiving the central screw 340. The housing 368 may further comprise a pair of chambers 376 on either side of the through bore 374. The housing 368 may further include a ratchet pawl 378 in each chamber 376. Embodiments of the ratchet pawls 378 may be spring loaded so that the ratchet pawls 378 may maintain contact with the central screw 340 while the locking plate 304 rotates about the trunion assembly 368. The ratchet pawls 378 may be assembled from the side of the housing 368. The ratchet pawls 378 may each have spring cuts to allow the ratchet pawls 378 to compress further into the chambers 376. The spring cuts may be the height of an electric discharge machining wire to create a small gap within each leaf of the ratchet pawls 378 being self-limiting as it collapses upon itself. Insertion of the central screw 340 into the through bore 374 (e.g., from right to left of FIG. 68) should cause the teeth (or threading) of the central screw 340 to engage the ratchet pawls 378 causing the ratchet pawls 378 to recess into the chambers 376. The angling of the teeth on the ratchet pawls 378 should resist backwards motion of the central screw 340 after insertion into the through bore 374. In this manner, the ratchet pawls 378 may be operable to secure the trunion assembly 368 and thus the locking plate 304 onto the central screw 340.

Figure 70:
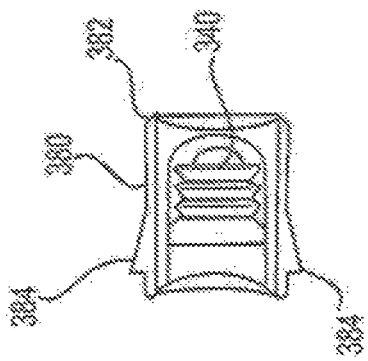
FIG. 70 is cross-sectional view of a tube that can be used to release the pawls of the trunion assembly of FIG. 68 according to one example implementation.

FIG. 70 illustrates a tube 380 that can be used to release the ratchet pawls 378 in accordance one example implantation. The tube 380 may be sized to fit over the central screw 340. The tube 380 may be advanced over the central screw 340 and into the back end of the through bore 374 until the leading end or nose 382 of the tube 380 engages the ratchet pawls 378. Pressure from the tube 380 combined with large chamfers on the ratchet pawls should cause the ratchet pawls 378 to compress. When fully inserted, the tube 380 includes one or more teeth 384 configured to snap into the ratchet pawls 378 allowing complete release of the central screw 340.

As illustrated by FIGS. 68 and 69, the housing 368 may have an upper surface 386 and a lower surface 388. In embodiments, the upper and lower surfaces 386 and 388 may each be curved. As illustrated, the upper and lower surfaces 386 and 388 may be sloped inward from the rear to the front of the housing 368. In some embodiments, the upper and lower surfaces 386 and 388 may each comprise a projection 390. The projection 390 may engage the locking plate 304 to limit its rotation about the trunion assembly 356.

Figure 71:
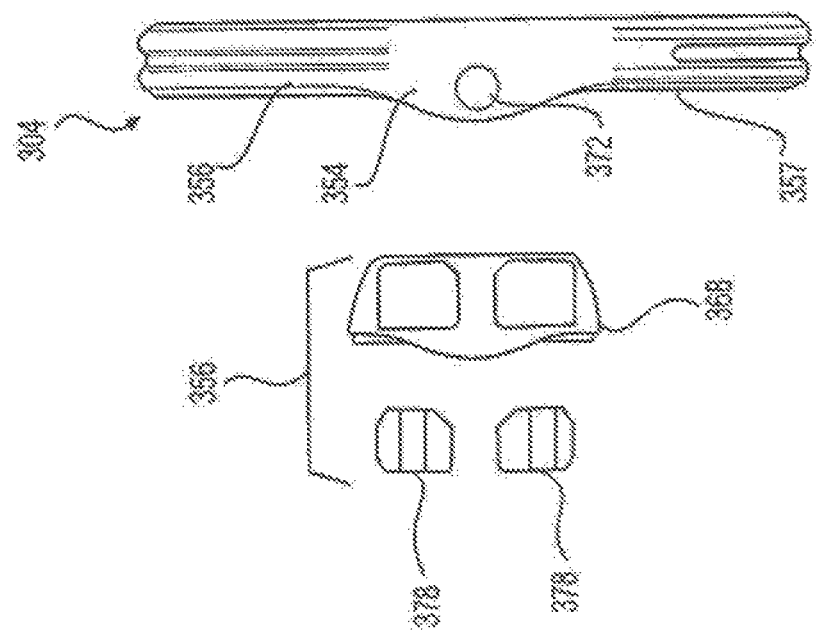

Referring to FIGS. 71-75, assembly of the locking plate 304 shown on FIGS. 66 and 67 will now be described according to an example implementation. As illustrated by FIG. 71, the locking plate 304 may comprise an upper portion 350, a lower portion 352, and a central portion 354 coupling the upper portion 350 and the lower portion 352. The trunion assembly 356 may comprise a housing 368 and a pair of ratchet pawls 378. The housing 368 may comprise a pair of windows 392 for receiving the ratchet pawls 378 into chambers 376 (FIG. 68). The ratchet pawls 378 may be inserted into the housing 368 from the side via windows 392, as shown on FIG. 72. The trunion assembly 356 comprising the housing 368 having the ratchet pawls 378 disposed therein may then be inserted into the opening in the central portion 354 of the locking plate 302, as best seen in FIG. 73. The trunion assembly may comprise projections 370 that are received in openings 372 in the central portion 354 to secure the trunion assembly 356 in the central portion 354. The projections 370 may be chamfered or otherwise angled on their leading edges to allow insertion into the openings 372. The plate assemblies 358 may then inserted into the upper portion 350 and lower portion 352 of the locking plate 304. In embodiments, the spike assemblies 358 may be assembled and inserted into the locking plate 304 in a manner similar to that discussed above with respect to FIGS. 63-65.

Figure 74:
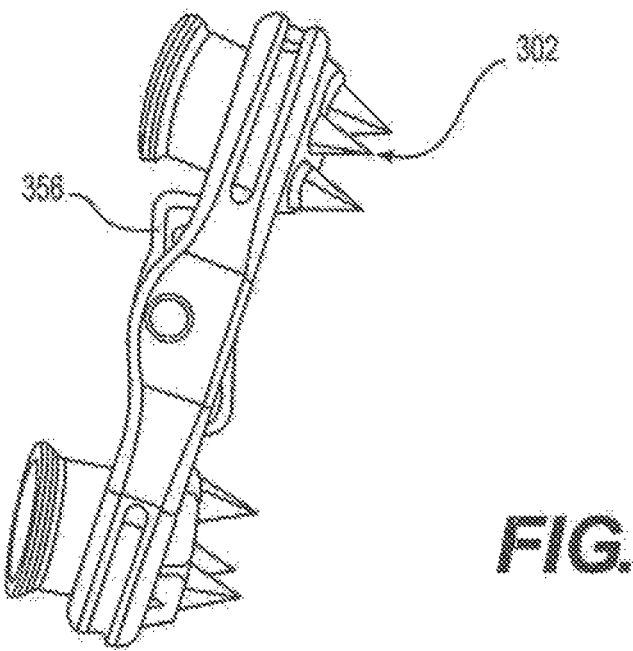
FIG. 74 is a side view showing rotation of a locking plate for a medical device according to one example implantation.
Figure 75:
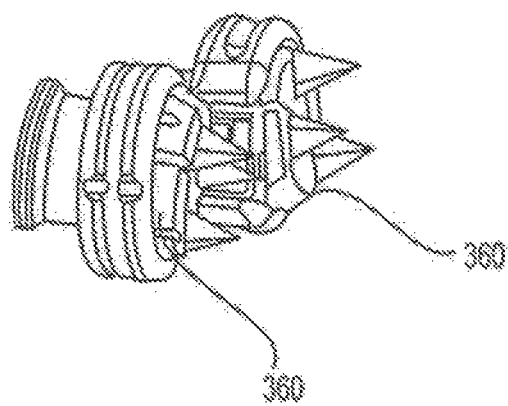
FIG. 75 is a perspective view showing angulation of the spike assembly of the locking plate of FIG. 74.

As previously mentioned, the locking plate 304 may be free to rotate about the trunion assembly 356 even where the trunion assembly 356 is in engagement with central screw 340. FIG. 74 is a side view of the locking plate 304 illustrating rotation of the locking plate 304 according to one example implementation. Additionally, the spike spheres 360 may also be free to articulate with respect to the locking plate 304. FIG. 74 illustrates articulation of the spike spheres 360 in accordance to one example implantation. Rotation of the locking plate 304 and/or articulation of the spike spheres 360 can provide an adaptable medical device 10 that can accommodate variances in spinous process geometry, for example, with the goal of anterior and secure placement.

An embodiment for using the medical device 300 will now be described in accordance with one example implementation. For example, a method may comprise inserting the barrel 306 of the medical device 300 into an interspinous space. The method may further comprise expanding the barrel 306 from a collapsed form having a first height to an expanded form having a second height, where the second height is greater than the first height. As discussed above, the central screw 340 may be rotated to expand the barrel 306 from a collapsed form to an expanded form in the interspinous space. The process may further include inserting the locking plate 304 onto the central screw 340 and moving the locking plate 304 towards the first plate such that the locking plate 304 and the first plate 302 engage a spinous process. The locking plate 304 may be free to rotate about its center (e.g., the trunion assembly 356) to accommodate spinous process geometry. In addition, the spike spheres 324 and 360 of the first plate 302 and the locking plate 304, respectively, may also be free to articulate for accommodation of spinous process geometry. The spike spheres 324 and 360 may be locked into place during compression into the spinous process.

Figure 77:
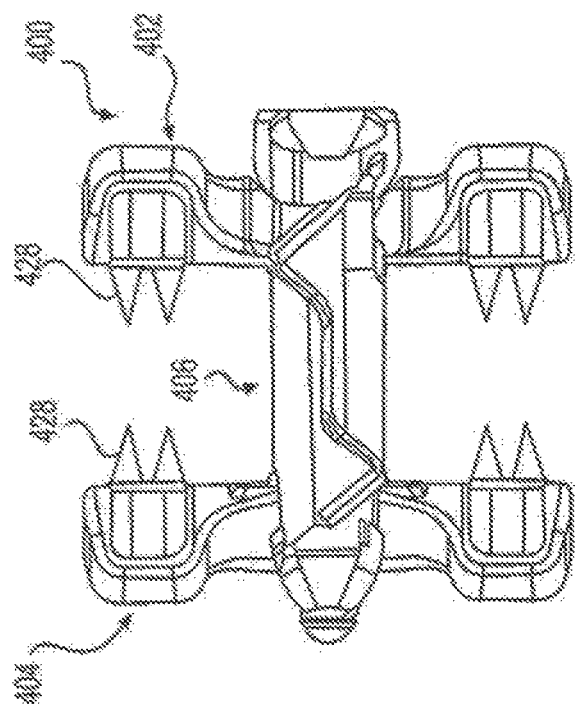
FIG. 77 is a side view of the medical device of FIG. 76.
Figure 76:
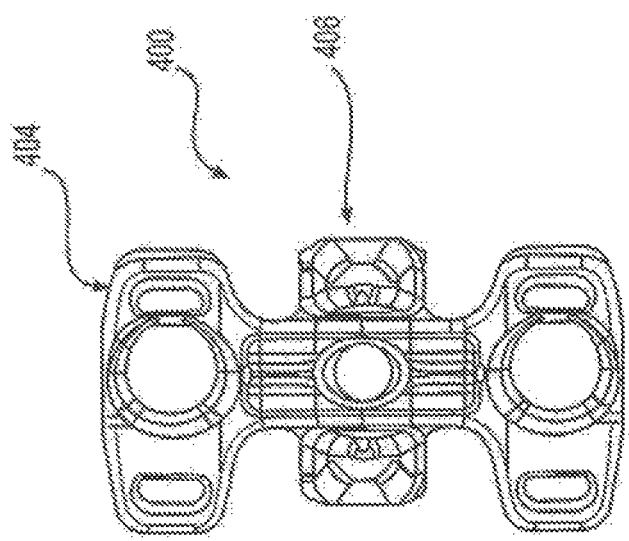
FIG. 76 is an end view of a medical device according to one example implementation.
Figure 78:
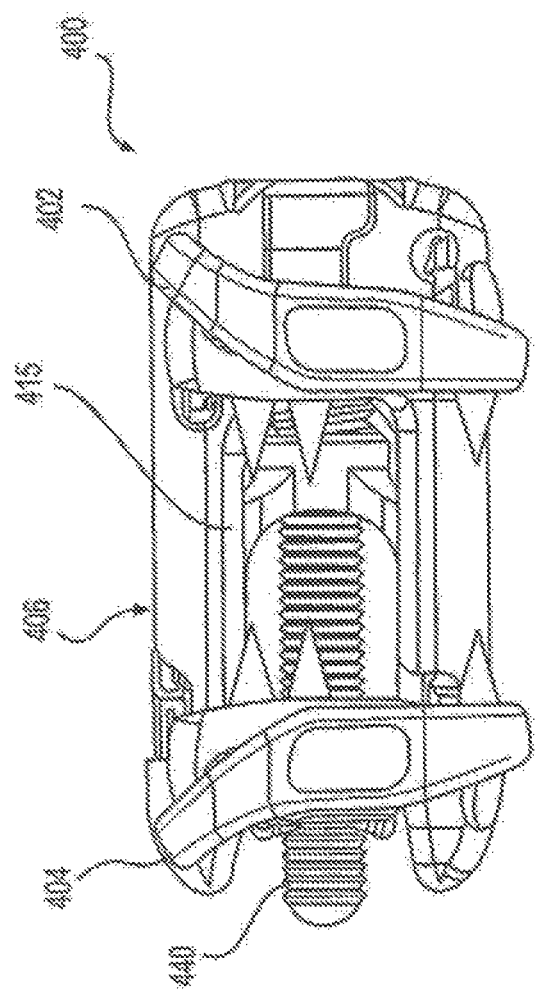
FIG. 78 is a top view of the medical device of FIG. 76.

FIGS. 76-78 illustrate a medical device 400 according to one example implementation. FIGS. 76-78 are an end view, side view, and top view, respectively, of the medical device 400. The medical device 400 may be implanted into a patient and referred to as a spinous process fusion device. In the illustrated embodiment, the medical device 400 includes a first plate 402, a second plate 404 (e.g., also referred to as locking plate 404), and an expandable central barrel (also referred to as a barrel) 406. The first plate 402 and the second plate 404 expand in overall height as the medical device 400 expands. The first plate 402 and the second plate 404 each include spikes 428, best seen on FIG. 77, which engage the spinous process.

Figure 79:
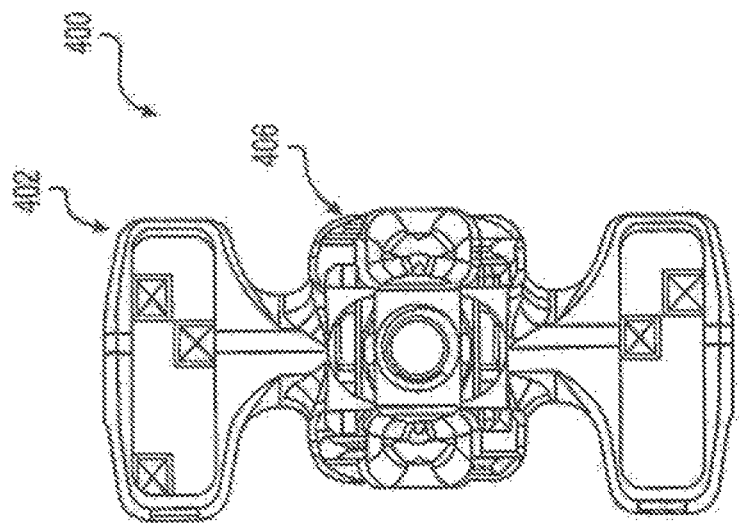
FIG. 79 is an end view of the medical device of FIG. 76 with a locking plate removed in accordance with one example implementation.
Figure 80:
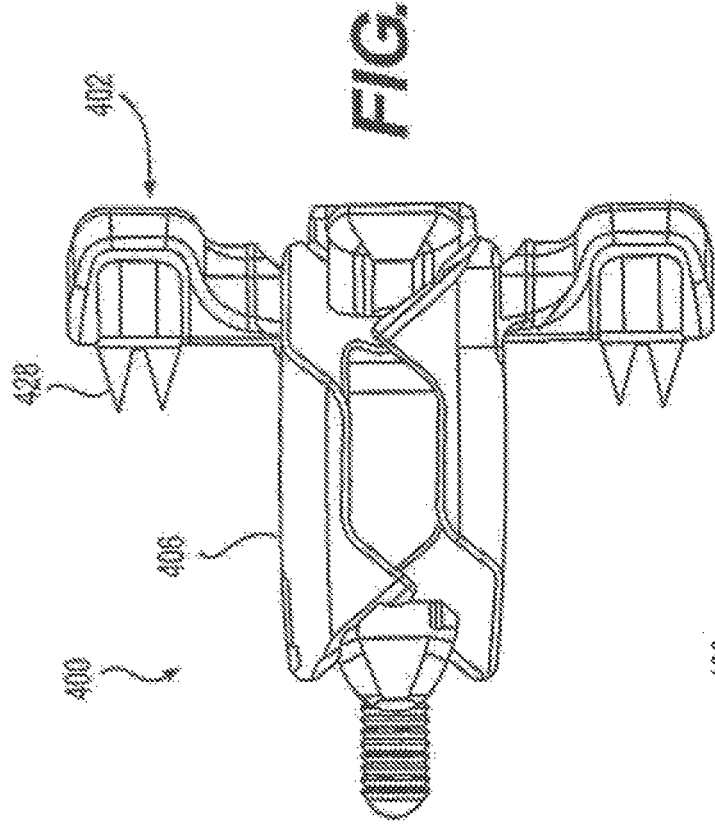
FIG. 80 is a side view of the medical view of FIG. 76 with a locking plate removed in accordance with one example implementation.
Figure 81:
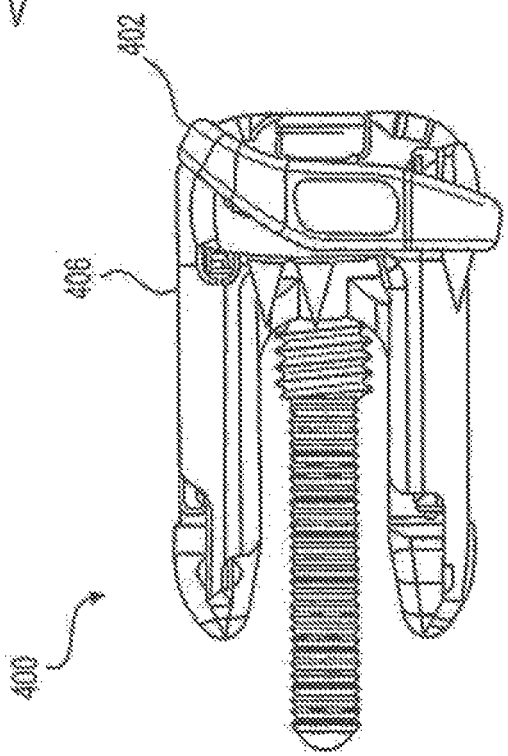
FIG. 81 is a top view of the medical view of FIG. 76 with a locking plate removed in accordance with one example implementation.

FIGS. 79-81 illustrate an end view, side view, and top view, respectively, of the medical device 400, which illustrate the barrel 406 in the expanded position with the locking plate 404 removed. The locking plate 404 may be attached after the barrel 406 with the first plate 402 is inserted to lock the device 400 in place. The barrel 406 may be inserted into the interspinous space without the locking plate 404 and then expanded. The locking plate 404 may then be attached to the barrel 406 after insertion to the lock the medical device 400 in place in engagement with the spinous process. As best seen on FIG. 78, the medical device 400 may include a central chamber 415 (or graft window) for the packing of bone graft material, which can be packed before or after insertion. The design of the medical device 400 may allow for placement with or without removal of the supraspinous ligament, depending on the surgeon's preference, for example.

Referring now to FIGS. 82-85, the barrel 406 will now be described in more detail in accordance with present embodiments. FIGS. 82-85 illustrate an example technique for assembly of the barrel 406. In the illustrated embodiment, the barrel 406 includes a first portion 408 (e.g., upper portion 408) and a second portion 410 (e.g., lower portion 410). The first portion 408 may include upper sidewalls 412. The ramped upper sidewalls 412 may include ramped portions 416 on either end of the ramped sidewalls 414. The second portion 412 may also include ramped lower sidewalls 414. The ramped lower sidewalls 414 may include ramped portions 418 on either end. As best seen in FIG. 85, the ramped lower sidewalls 414 and the ramped upper sidewalls 412 may overlap when the medical device 400 is collapsed.

The barrel 406 in the illustrated embodiments may be an expandable barrel that may be in a collapsed position for insertion into a patient in the interspinous space without resistance and then expanded up to the barrel's maximum height. In one example implementation, the maximum expanded height of the barrel may be about 4 mm greater than the collapsed height or, alternatively, about 6 mm greater than the collapsed height. The central barrel 406 may provide interspinous distraction and may offload the forces of the spikes 428 on the plates 402 and 404 to reduce the chances of breaking a spinous process. The barrel 406 may be inserted, laterally or posteriorly, in a smaller height and then expanded to provide distraction, eliminating forces on the spinous process and potential frustration for a surgeon performing the implantation.

With continued reference to FIGS. 82-85, the first plate 402 may include an upper portion 420 and a lower portion 422. The upper portion 420 of the first plate 402 may extend generally vertically from the first portion 408 of the barrel 406. As illustrated, the upper portion 420 may extend from one end of the barrel 406. The upper portion 420 may be integrally formed with the first portion 408. The lower portion 422 of the first plate 402 may extend from the second portion 410 of the barrel 406 in a direction generally opposite to the upper portion 420. As illustrated, the lower portion 420 may extend from the same end of the barrel 406 as the upper portion 420 but in the opposite direction. The lower portion 422 may be integrally formed with the second portion 410. The first plate 402 may be shaped in a lordotic profile to match the lumbar anatomy.

The medical device 400 may further include an actuator assembly 438 (best seen on FIGS. 82-85) for raising and lowering the first and second portions 408 and 410 of the barrel 406 and, thus, the upper and lower portions 420, 422 of the first plate 402. The actuator assembly 438 may be disposed between the first and second portions 408 and 410 of the barrel 406. As illustrated, the actuator assembly 438 may comprise a central screw 440, a front ramped actuator 446 and a rear ramped actuator 444. The front ramped actuator 446 may be bullet shaped on its front end to facilitate insertion into a patient. The front ramped actuator 446 may have a ramped expansion portion 442 and an extension portion 448. The ramped expansion portion 442 may be located at a front end of the barrel 406 with the extension portion 448 extending from the ramped expansion portion 442 towards a rear end of the barrel 406. The central screw 440 may extend through the barrel 406 and engage the extension portion 448. The first and second portions 408 and 410 of the barrel 406 may slidingly engage the ramped expansion portion 442. For example, the ramped expansion portion 442 may engage ramped surface 416 of the first and second portions 408 and 410 at a front end of the barrel 406. The ramped expansion portion 442 may have dovetail connections with the first and second portions 408 and 410, respectively. The rear ramped actuator 444 may be disposed at a rear end of the barrel 406. The first and second portions 408 and 410 of the barrel 406 may slidingly engage the rear ramped actuator 444. For example, the rear ramped actuator 444 may also engage ramped surfaces 416 of the first and second portions 408 and 410 of the barrel. The rear ramped actuator 444 may have dovetail connections with the first and second portions 408 and 410, respectively. The central screw 440 may extend through the rear ramped actuator 444 to engage the extension portion 448.

An example embodiment for expanding the barrel 406 will now be described. The barrel 406 may expand by forcing the first and second portions 408 and 410 vertically outward in a direction away from one another. In this manner, the upper and lower portions 420 and 422 of the first plate 402 may also be expanded vertically outward. The barrel 406 may contract by forcing the first and second portions 408 and 410 to contract in a direction toward one another, thus also moving the upper and lower portions 420 and 422 of the first plate 402 together. In some embodiments, the actuator assembly 438 may be used to raise and lower the first and second portions 408 and 410. By way of example, the central screw 440 may be turned to contract the actuator assembly 438. The rear ramped actuator 442 may be held in place while the central screw 440 is turned causing the front ramped actuator 440 to be drawn toward the rear ramped actuator 442. The rear ramped actuator 442 and the front ramped actuator 440 may engage the ramped upper sidewalls 412 and the ramped lower sidewalls 414 in the first and second portions 408 and 410 forcing the first and second portions 408 and 410 to expand from a collapsed position. A counter rotation of the central screw 440 may cause the front ramped actuator 440 and the rear ramped actuator 442 to separate causing the first and second portions 408 and 410 to collapse from the expanded state.

Assembly of the barrel 406 of the medical device 400 will now be described according to an example implementation with reference to FIGS. 82-85. As illustrated by FIG. 82, the barrel 406 may comprise a first portion 408 and a second portion 410. The first plate 402 may be defined by upper portion 420 and lower portion 422. Upper portion 420 may extend from first portion 408 of the barrel 406, and lower portion 422 may extend in an opposite direction from second portion 410 of the barrel 406. As further illustrated by FIG. 83, the actuator assembly 438 may comprise a central screw 440, a front ramped actuator 442, and a rear ramped actuator 444. In FIG. 83, the rear ramped actuator 444 may be slid onto the first portion 408 of the barrel 406. As illustrated, the rear ramped actuator 444 may be engage (e.g., through a dovetail connection) a rear end of the upper ramped sidewalls 412 of the first portion 408. In FIG. 84, the front ramped actuator 442 may then the slide onto the second portion 410 of the barrel 406. As illustrated, the ramped expansion portion 446 may engage (e.g., through a dovetail connection) a front end of the lower ramped sidewalls 414 of the second portion 410. In FIG. 85, the first portion 408 and second portion 410 of the barrel 406 have been placed together in a contracted position with a front end of the upper ramped sidewalls 412 engaging the ramped expansion portion 446 and a rear end of the lower ramped sidewalls 414 engaging the rear ramped actuator 444.

Figure 87:
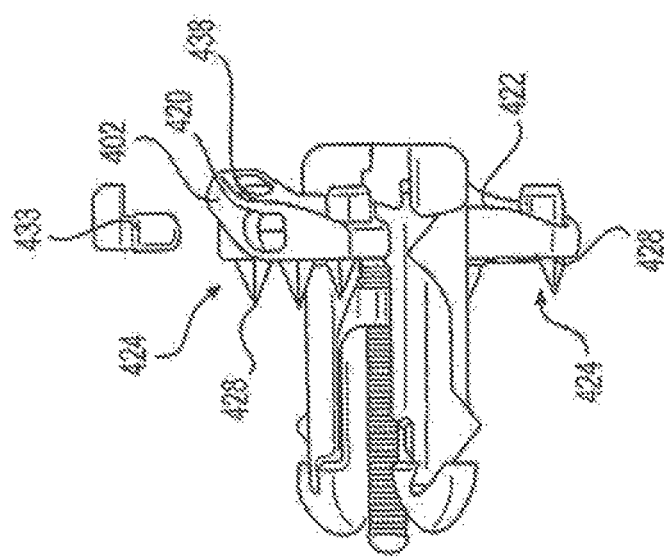
FIGS. 86-90 illustrate assembly of the spike assembly for the medical device of FIG. 76 in accordance with one example implementation.
Figure 89:
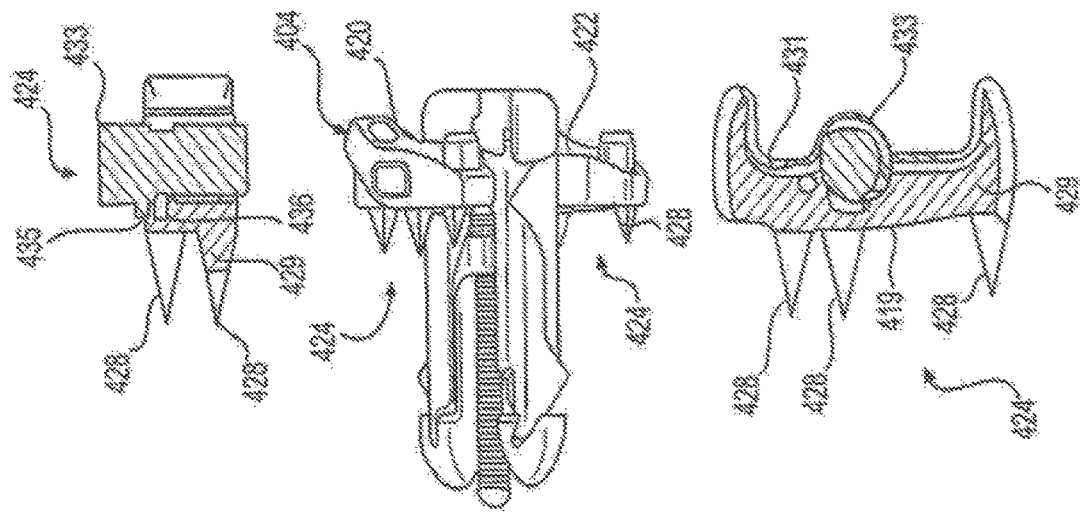
Figure 88:
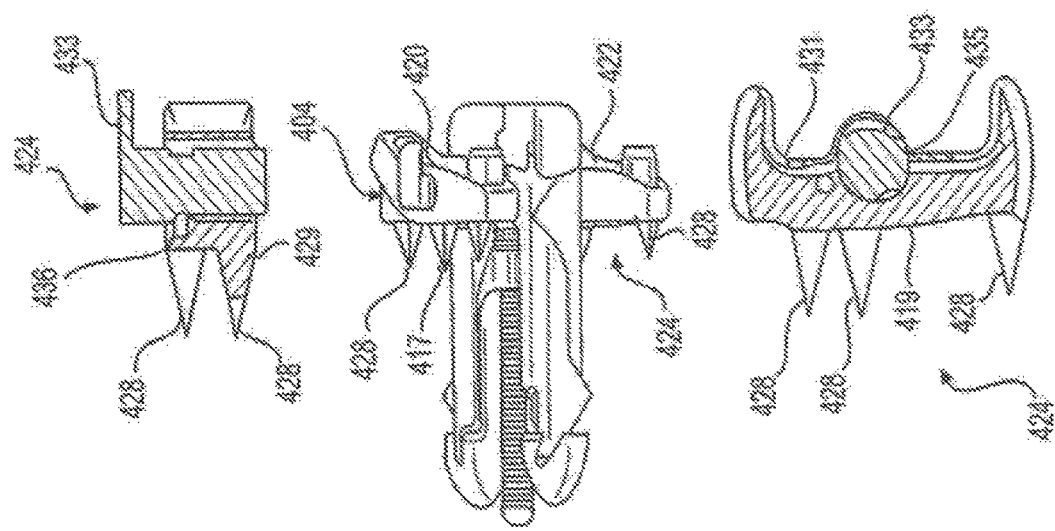
Figure 90:
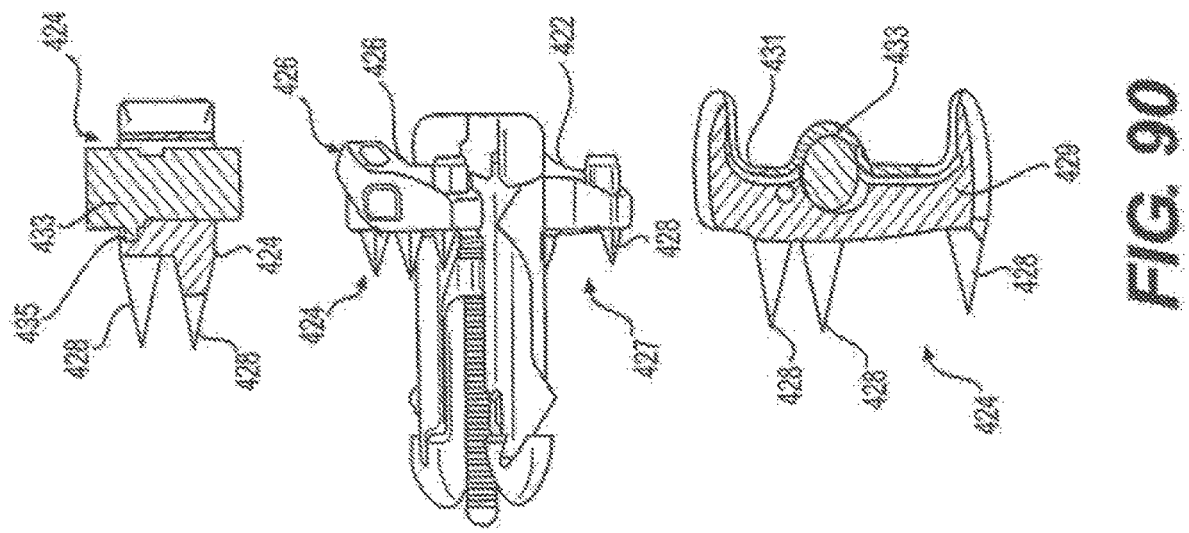

Referring to FIGS. 86-90, the pivoting spike assembly 424 of the medical device 400 will now be described according to an example implementation. FIGS. 86-90 illustrate assembly of the pivoting spike assembly 424 in the first plate 402. FIGS. 88-90 also show side, cross-sectional views and top views of the spike assembly 424. As illustrated, the first plate 402 may include a pivoting spike assembly 424 on both the upper portion 420 and the lower portion 422. The pivoting spike assemblies 424 may each be received within an opening 426 (best seen on FIG. 86) in both the upper portion 420 and the lower portion 422. Each pivoting spike assembly 424 may include multiple projections (e.g., spikes 428). Each spike assembly 424 may comprise a base 429 with a hole 432 (best seen on FIG. 86) for attachment to either the upper portion 420 or the lower portion 422 of the first plate 402. The spike assembly 424 may further comprise leaf spring feature 431.

Figure 86:
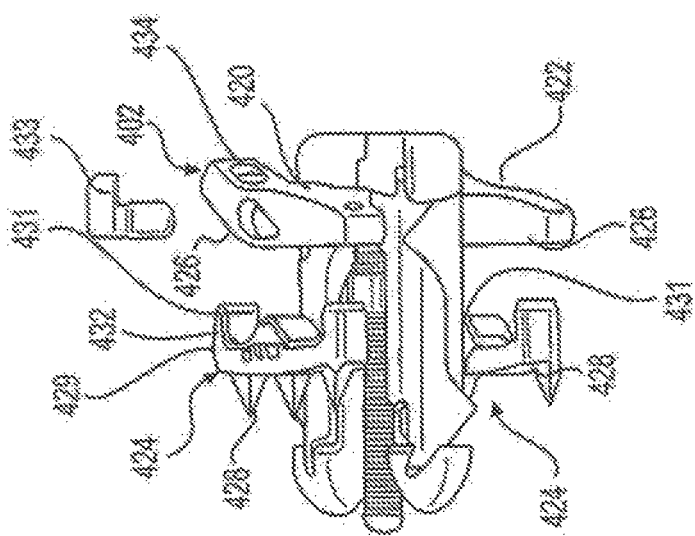

Assembly of the pivoting spike assembly 424 in the first plate 402 will now be described in accordance with an example embodiment. The following description describes insertion of the pivoting spike assembly 424 into the upper portion 420 of the first plate, but it should be understood that a pivoting spike assembly 424 may also be inserted into the lower portion 422 in a similar manner. As illustrated by FIGS. 86 and 87, a fastener 433 may be inserted into the hole 432 to hold the spike assembly 424 to the first plate 402. Once the pivoting spike assembly 424 is placed within the upper portion 420 and lower portion 422 of the first plate 402, the hole 432 of the assembly 424 may be aligned with a hole 434 of the first plate 402. As illustrated in FIG. 88 the fastener 433 may first be inserted in the hole 434 of the upper portion 420 and lower portion 422 of the first plate 402. The fastener 433 may be configured in a cam-type configuration that includes a lobe 435. Inserting the fastener 433 sideways allows the lobe 435 to pass through the hole 434 of the first plate 402. The lobe 435 may come to rest on the pivoting spike assembly 424. Rotating the fastener 433 ninety degrees, as seen in FIG. 89, may force the lobe 435 into the leaf spring feature 431 causing it to expand. While the leaf spring feature 431 is expanded the fastener 433 may be advanced further into the hole 432 in the assembly 424. Further advancement of the fastener 433, as seen in FIG. 90, may push the lobe 435 of the fastener 433 below the leaf spring feature 431 into a groove 436 found in the hole 432 of the pivoting spike assembly 424. Once the lobe 435 is in the groove 436 of the pivoting spike assembly 424, the leaf spring feature 431 may snap back into place against the fastener 433. This may secure the fastener 433 to the pivoting spike assembly 424 and prevent detachment of the assembly 424 from the upper portion 420 or lower portion 422 of the first plate 402. An audible sound of the leaf spring feature 431 snapping back into place may be used in some embodiments to alert the assembler that the medical device 400 has been properly put together.

Figure 91:
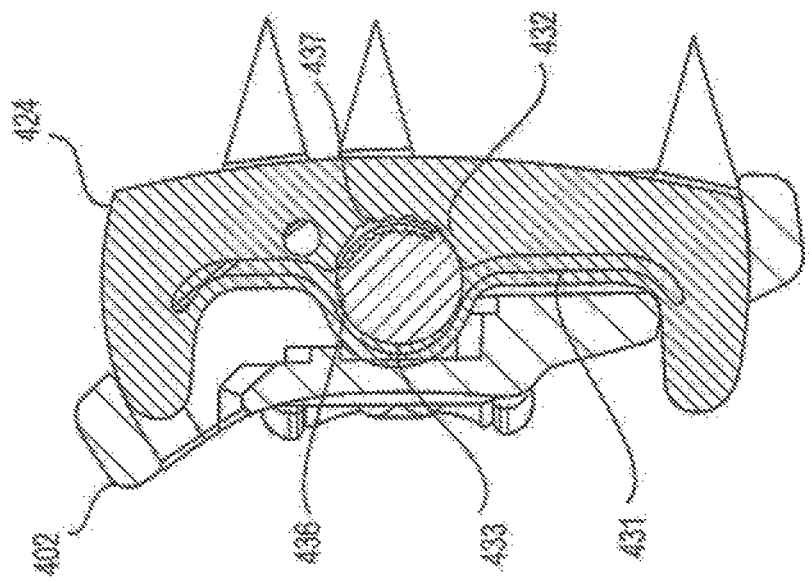
FIGS. 91 and 92 illustrate the spike assembly of the medical device of FIG. 76 in accordance with one example implementation.
Figure 92:
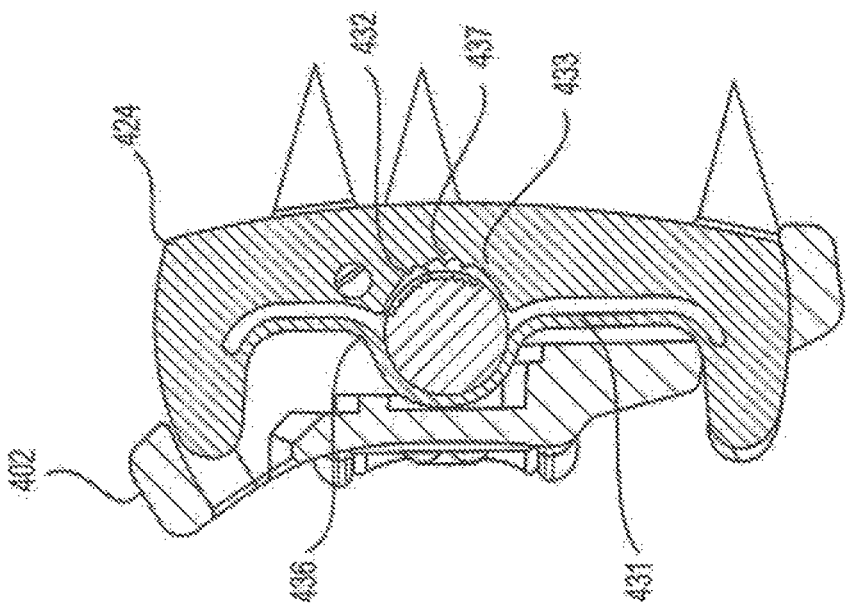

FIGS. 91 and 92 illustrate the pivoting spike assembly 424 secured in the first plate 402 in more detail in accordance with example embodiments. As illustrated in FIGS. 91 and 92, the pivoting spike assembly 424 may be free to move around the fastener 433. The fastener 433 and the inner hole 432 may have matching serrations 436 and 437 respectively. The leaf spring feature 431 may prevent serrations 436 and 437 from meshing, allowing the pivoting spike assembly 424 to be mobile. When compression force is applied to the spike assembly 424, the leaf spring feature 431 may collapse upon the fastener 433, allowing the serrations 436 and 437 to mesh and restrict movement as seen in FIG. 92. When the implant is loosened or removed, the leaf spring feature 431 pushes against fastener 433, effectively remobilizing the pivoting spike assembly 424 as seen in FIG. 91.

While the term "spikes" may be used for the projections in the pivoting spike assembly 424, other types of projections may be used that may have a more tapered point or rounded point or other type of ending to the projection. The spikes 428 may be used to attach firmly and bite into the spinous processes above and below an interspinous space. The spikes 428 may be pyramid shaped with a base portion secured or integrally formed on the pivoting spike assembly 424. The sides of the spikes 428 may extend from the base to form a point in the shape of a pyramid. In other example implementations, the spikes 428 may be formed into other shapes that rise to a point to enable the spike to engage the spinous process. As discussed above, the end of the spikes 428 may include tips other than a point such as, for example, rounded tip, a square tip or other-shaped tip. The example illustration of the medical device 400 includes three (3) spikes 428 on each pivoting spike assembly 424 of the first plate 402. In other example implementations, fewer or more spikes 428 may be included. The first plate 402 and the spikes 428 may be made of titanium. In other implementations, the first plate 402 and the spikes 428 may be made of other biocompatible materials.

Figure 94:
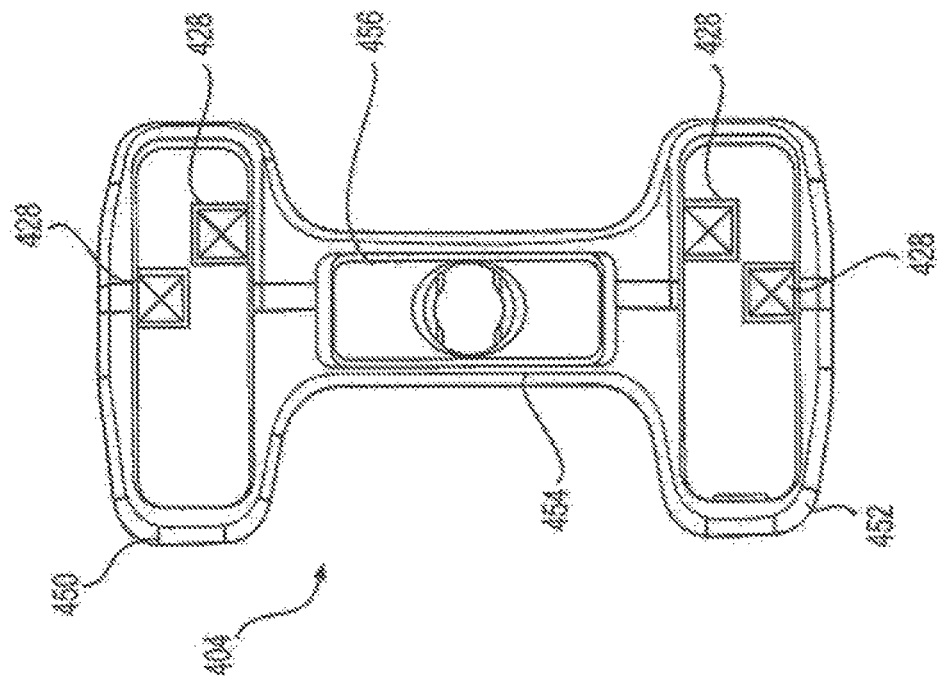
FIGS. 93 and 94 illustrate the locking plate of the medical device of FIG. 76 in accordance with one example implementation.
Figure 93:
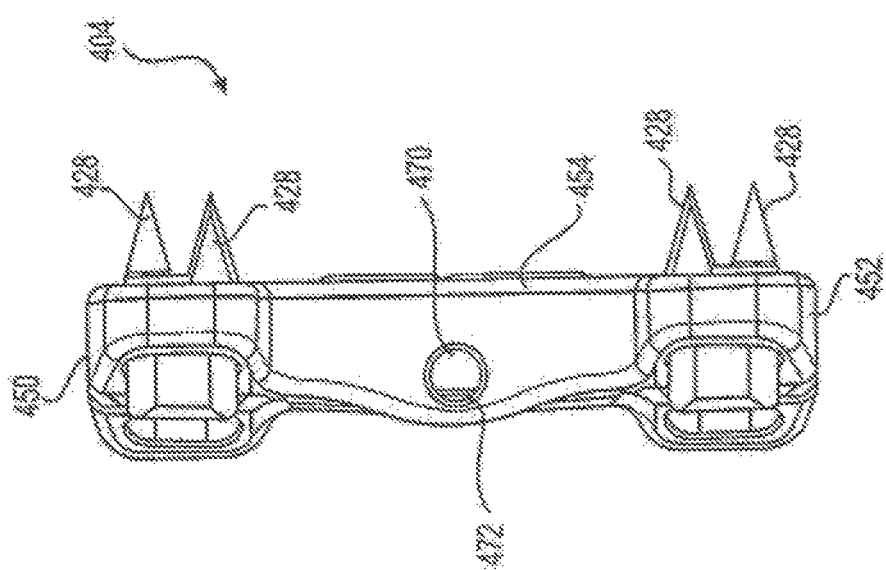

Referring to FIGS. 93 and 94, the second or locking plate 404 will now be described in more detail with respect to one example implementation. FIGS. 93 and 94 are side and front views of the locking plate 404 in accordance with example embodiments. The locking plate 404 may be inserted onto the central screw 440 after the barrel 406 has been expanded to lock the barrel 406 in position, as best seen in FIG. 78. As illustrated by FIGS. 93 and 94, the locking plate 404 may comprise an upper portion 450 and a lower portion 452. A central portion 454 may connect the upper portion 450 to the lower portion 452. The upper portion 450, lower portion 452, and central portion 454 may be integrally formed as a single plate component in some embodiments. The central portion 454 includes an opening (e.g., a central opening) to receive trunion assembly 456. The locking plate 404 may rotate about the trunion assembly 456 and can be locked at various angles at any position within its range of motion. In some embodiments, the trunion assembly 456 may be configured so that the locking plate 404 rotates about its center. The locking plate 404 may include spikes 428 on both the upper portion 450 and the lower portion 452.

Figure 96:
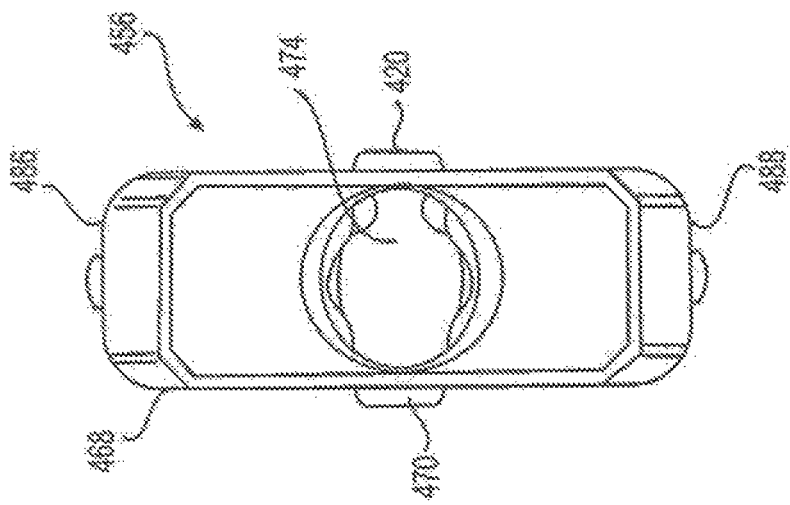
FIGS. 95 and 96 illustrate the trunion assembly for use with a locking plate in accordance with one example implementation.
Figure 95:
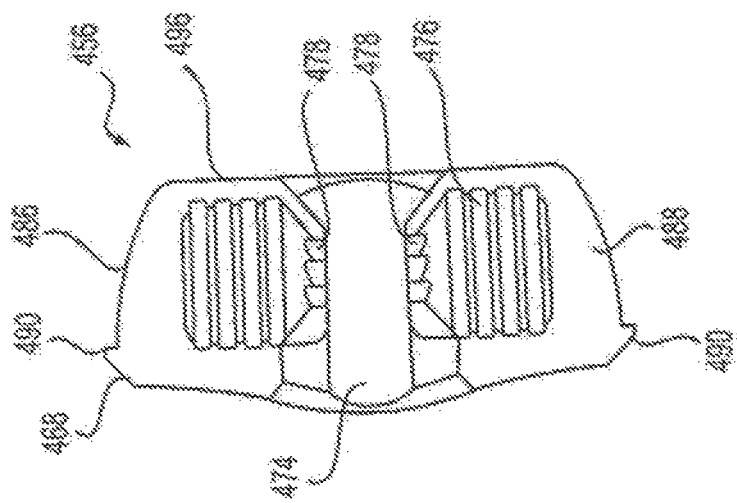

With additional reference to FIGS. 95 and 96, the trunion assembly 456 will described in more detail with respect to one example implementation. As illustrated, the trunion assembly 456 may comprise a housing 468. The housing 468 may have laterally extending projections 470 for rotatably coupling the trunion assembly 468 to the central portion 454 of the locking plate 404 while allowing the locking plate 404 to rotate with respect to the trunion assembly 468. As illustrated, there may be a pair of projections 470 that extend from opposite sides of the housing 468 and are each received in corresponding openings 472 (best seen on FIG. 93) in the central portion 454. The housing 468 may further have a through bore 474 for receiving the central screw 440. The housing 468 may further comprise a pair of chambers 476 on either side of the through bore 474. The housing 468 may further include a ratchet pawl 478 in each chamber 476. Embodiments of the ratchet pawls 478 may be spring loaded so that the ratchet pawls 478 may maintain contact with the central screw 440 while the locking plate 404 rotates about the trunion assembly 468. The ratchet pawls 478 may be assembled from the side of the housing 468. The ratchet pawls 478 may each have spring cuts to allow the ratchet pawls 478 to compress further into the chambers 476. The spring cuts may be the height of an electric discharge machining wire to create a small gap within each leaf of the ratchet pawls 478 being self-limiting as it collapses upon itself. Insertion of the central screw 440 into the through bore 474 (e.g., from right to left of FIG. 78) should cause the teeth (or threading) of the central screw 440 to engage the ratchet pawls 478 causing the ratchet pawls 478 to recess into the chambers 476. The angling of the teeth on the ratchet pawls 478 should resist backwards motion of the central screw 440 after insertion into the through bore 474. In this manner, the ratchet pawls 478 may be operable to secure the trunion assembly 468 and thus the locking plate 404 onto the central screw 440.

Figure 97:
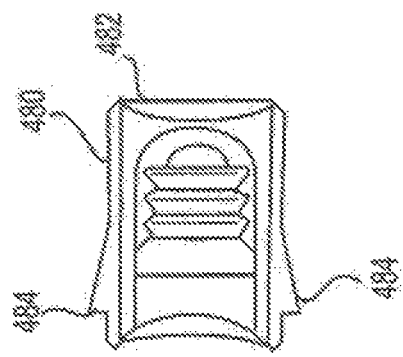
FIG. 97 illustrates a tube that can be used with the trunion assembly in accordance with one example implementation.

FIG. 97 illustrates a tube 480 that can be used to release the ratchet pawls 478 in accordance to one example implantation. The tube 480 may be sized to fit over the central screw 440. The tube 480 may be advanced over the central screw 440 and into the back end of the through bore 474 until the leading end or nose 482 of the tube 480 engages the ratchet pawls 478. Pressure from the tube 480 combined with large chamfers on the ratchet pawls should cause the ratchet pawls 478 to compress. When fully inserted, the tube 480 includes one or more teeth 484 configured to snap into the ratchet pawls 478 allowing complete release of the central screw 440.

As illustrated by FIG. 96, the housing 468 may have an upper surface 486 and a lower surface 488. In embodiments, the upper and lower surfaces 486 and 488 may each be curved. As illustrated, the upper and lower surfaces 486 and 488 may be sloped inward from the rear to the front of the housing 468. In some embodiments, the upper and lower surfaces 486 and 488 may each comprise a projection 490. The projection 490 may engage the locking plate 404 to limit its rotation about the trunion assembly 456.

Figure 99:
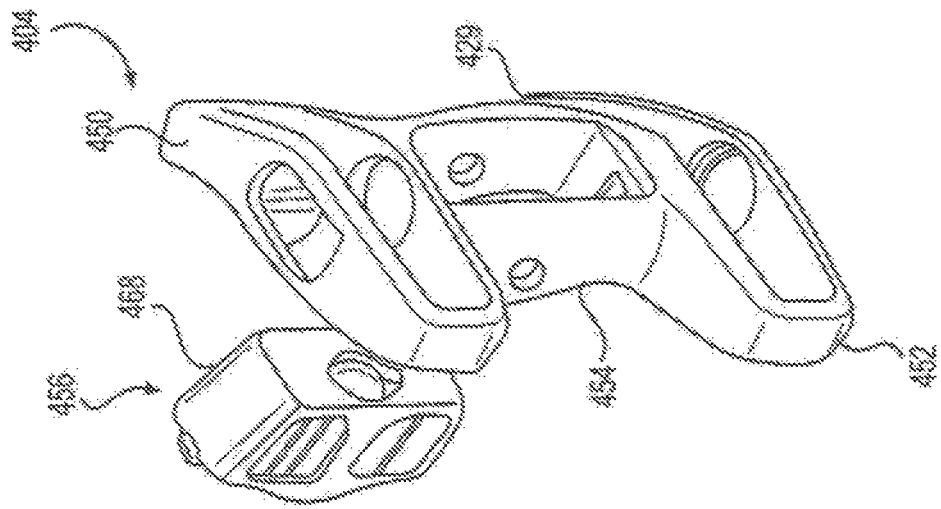
FIGS. 98-100 illustrate assembly of a locking plate in accordance with one example implementation.
Figure 98:
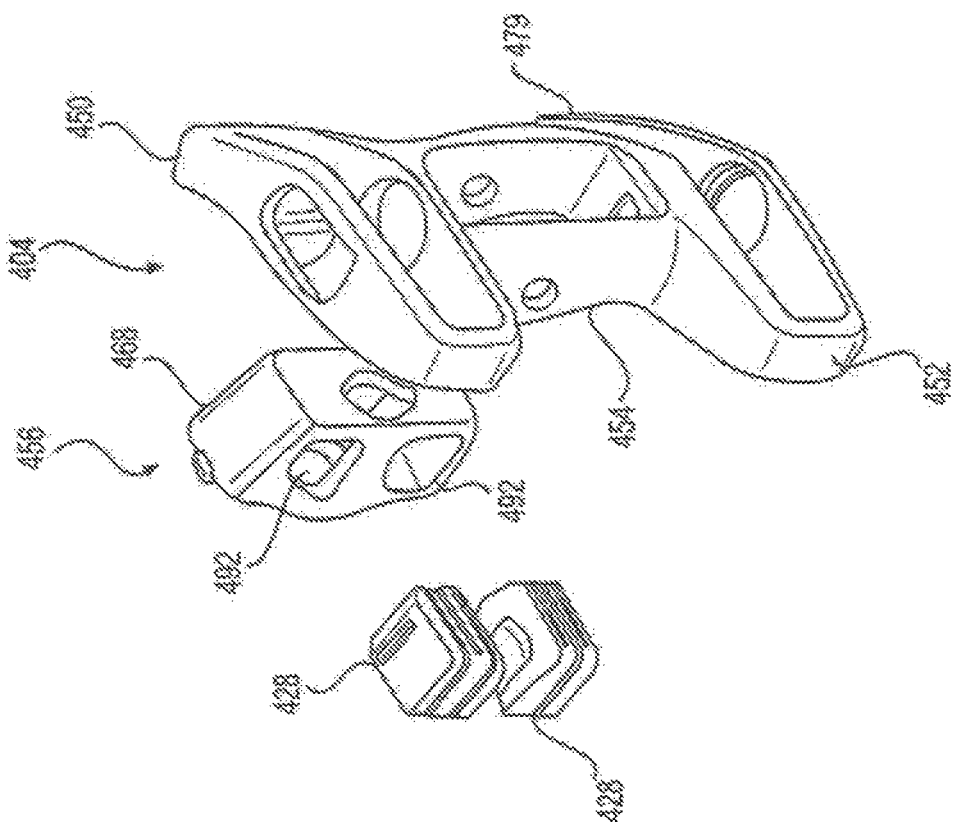
Figure 100:
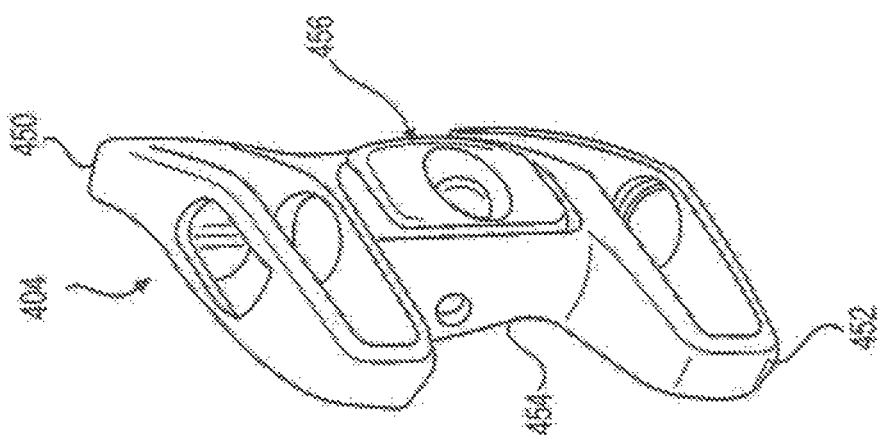

Referring to FIGS. 98-100, assembly of the locking plate 404 shown on FIGS. 93 and 94 will now be described according to an example implementation. As illustrated, the locking plate 404 may comprise an upper portion 450, a lower portion 452, and a central portion 454 coupling the upper portion 450 and the lower portion 452. The trunion assembly 456 may comprise a housing 468 and a pair of ratchet pawls 478. The housing 468 may comprise a pair of windows 492 for receiving the ratchet pawls 478 into chambers 476 (FIG. 95). The ratchet pawls 478 may be inserted into the housing 468 from the side via windows 492, as shown on FIG. 99. The trunion assembly 456 comprising the housing 468 having the ratchet pawls 478 disposed therein may then be inserted into the opening 479 in the central portion 454 of the locking plate 404, as best seen in FIG. 100.

Figure 101:
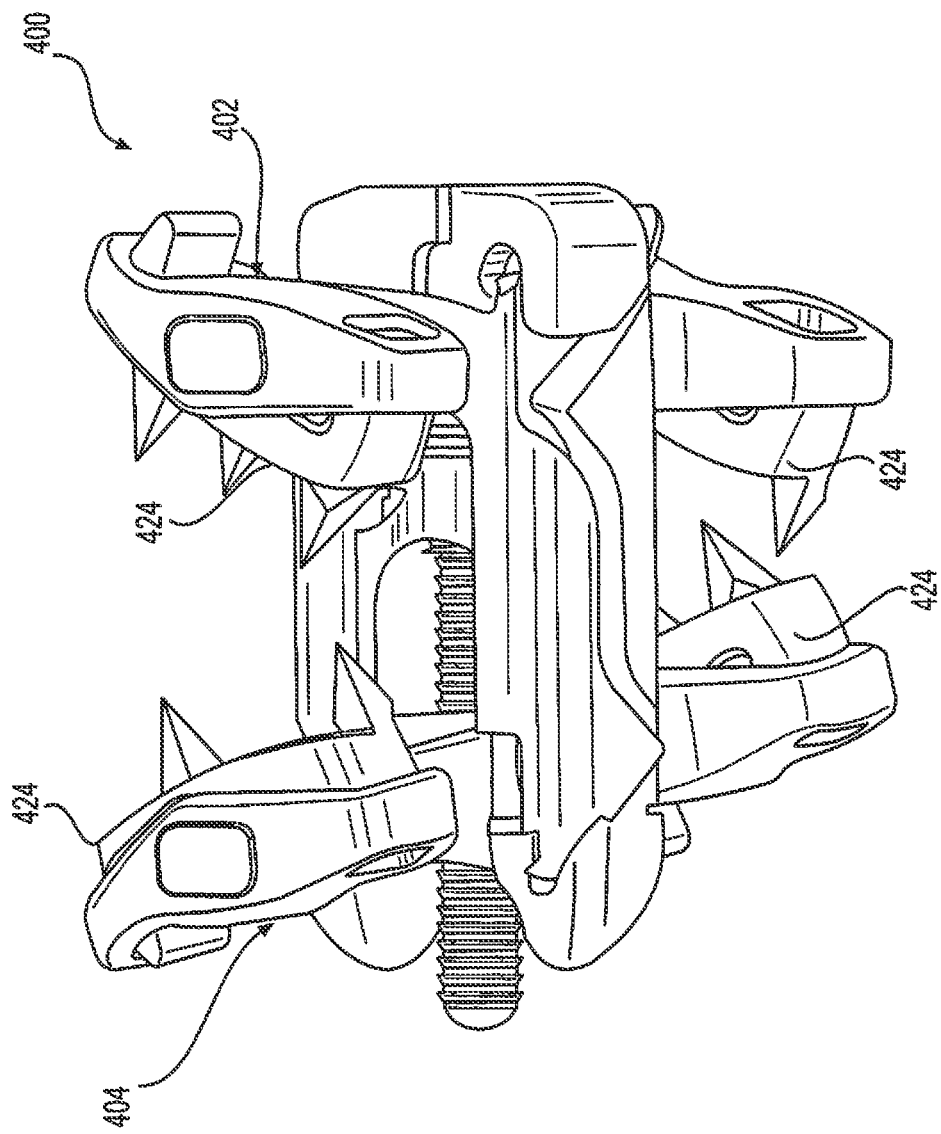
FIG. 101 illustrates rotation of a locking plate in accordance with one example implementation.

As previously mentioned, the locking plate 404 may be free to rotate about the trunion assembly 456 even where the trunion assembly 456 is in engagement with central screw 440. FIG. 101 is a view of the medical device 400 showing rotation of the locking plate 404 according to one example implementation. The locking plate 404 may also include a pivoting spike assembly 424 that may be assembled and function in a manner similar to that described above for the first plate 402. As illustrated, the pivoting spike assemblies 424 of the first plate 402 and the locking plate 404 may also be free to articulate with respect to the locking plate 404. Rotation of the locking plate 404 and/or articulation of the pivoting spike assemblies 424 can provide an adaptable medical device 400 that can accommodate variances in spinous process geometry, for example, with the goal of anterior and secure placement.

An embodiment for using the medical device 400 will now be described in accordance with one example implementation. For example, a method may comprise inserting the barrel 406 of the medical device 400 into an interspinous space. The method may further comprise expanding the barrel 406 from a collapsed form having a first height to an expanded form having a second height, where the second height is greater than the first height. As discussed above, the central screw 440 may be rotated to expand the barrel 406 from a collapsed form to an expanded form in the interspinous space. The process may further include inserting the locking plate 404 onto the central screw 440 and moving the locking plate 404 towards the first plate such that the locking plate 404 and the first plate 402 engage a spinous process. The locking plate 404 may be free to rotate about its center (e.g., the trunion assembly 456) to accommodate spinous process geometry. In addition, the pivoting spike assembly 424, the first plate 402, and the locking plate 404, respectively, may also be free to articulate for accommodation of spinous process geometry. The pivoting spike assembly 424 may be locked into place during compression into the spinous process.

The various components of the medical device 10, medical device 100, medical device 300, and medical device 400, described herein can be formed with any biocompatible material used for such a medical device. For example, each of the various components can be formed with one or more biocompatible plastics and/or one or more biocompatible metals such as, for example, titanium and stainless steel.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A method for implanting a medical device in a patient, comprising:
   inserting a medical device including:
   a barrel having an upper portion and a lower portion;
   an actuator assembly disposed in the barrel, the actuator assembly including a front ramped actuator in engagement with the barrel, a rear ramped actuator in engagement with the barrel, and a central screw that extends from the rear ramped actuator through the front ramped actuator; and
   a first plate having a first portion that extends from the upper portion, a second portion that extends from the lower portion, and a first pivoting spike assembly disposed in the first plate and adapted to pivot relative to the first plate, the first pivoting spike assembly including one or more spikes extending from a first side of the first plate;

rotating the central screw disposed in the barrel to cause the barrel to transition from a collapsed form having a first height to an expanded form having a second height;

inserting onto the central screw a second plate having multiple spikes extending from a first side of the second plate; and pivotally attaching the first pivoting spike assembly to the first plate with a fastener, wherein the first pivoting spike assembly includes a spring disposed to face the fastener such that when the spring is in an uncompressed state, the first pivoting spike assembly is free to move about the fastener.

2. The method of claim 1, wherein when a compression force applied to the first pivoting spike assembly, the spring collapses upon the fastener to immobilize the first pivoting spike assembly relative to the first plate.

3. The method of claim 2, wherein the first pivoting spike assembly includes serrations and the fastener includes corresponding serrations that mesh with the serrations of the first pivoting spike assembly to immobilize the first pivoting spike assembly relative to the first plate when the compression force is applied to the first pivoting spike assembly.

4. The method of claim 1, further comprising movably attaching the first pivoting spike assembly to the first plate with a fastener, wherein:

the first pivoting spike assembly includes a spring disposed to face the fastener such that when the spring is in an uncompressed state, the first pivoting spike assembly is free to move about the fastener, and when a compression force is applied to the first pivoting spike assembly, the spring collapse upon the fastener to immobilize the first pivoting spike assembly relative to the first plate.

5. The method of claim 4, wherein the first pivoting spike assembly includes serrations and the fastener includes corresponding serrations that mesh with the serrations of the first pivoting spike assembly to immobilize the first pivoting spike assembly relative to the first plate when the compression force is applied to the first pivoting spike assembly.

6. The method of claim 1, wherein the upper portion of the barrel comprises ramped upper sidewalls in engagement with the rear ramped actuator and the front ramped actuator, and wherein the lower portion of the barrel comprises ramped lower sidewalls in engagement with the rear ramped actuator and the front ramped actuator.

7. The method of claim 6, wherein the ramped upper sidewalls and the ramped lower sidewalls define a central opening configured to receive graft packing material.

8. The method of claim 1, wherein the first portion of the first plate is integrally formed with the upper portion of the barrel, and wherein the second portion of the first plate is integrally formed with the lower portion of the barrel.

9. The method of claim 1, wherein the second plate is a locking plate.

10. A method for implanting a medical device in a patient, comprising:

inserting a medical device including:
a barrel, the barrel having an upper portion and a lower portion;
an actuator assembly disposed in the barrel;

a first plate, formed integrally with the barrel, including a first portion that extends from the upper portion, a second portion that extends form the lower portion, and a first pivoting spike assembly disposed in the first plate and adapted to pivot relative to the first plate, the first pivoting spike assembly including one or more spikes extending from a first side of the first plate; and a locking plate having multiple spikes extending from a first side of the locking plate, the locking plate configured to be received on a central screw disposed in the actuator assembly;

rotating the central screw disposed in the barrel to cause the barrel to transition from a collapsed form having a first height to an expanded form having a second height;

inserting onto the central screw the locking plate; and pivotally attaching the first pivoting spike assembly to the first plate with a fastener, wherein the first pivoting spike assembly includes a spring disposed to face the fastener such that when the spring is in an uncompressed state, the first pivoting spike assembly is free to move about the fastener.

11. The method of claim 10, wherein when a compression force applied to the first pivoting spike assembly, the spring collapses upon the fastener to immobilize the first pivoting spike assembly relative to the first plate.

12. The method of claim 11, wherein the first pivoting spike assembly includes serrations and the fastener includes corresponding serrations that mesh with the serrations of the first pivoting spike assembly to immobilize the first pivoting spike assembly relative to the first plate when the compression force is applied to the first pivoting spike assembly.

13. The method of claim 10, further comprising movably attaching the first pivoting spike assembly to the first plate with a fastener, wherein:

the first pivoting spike assembly includes a spring disposed to face the fastener such that when the spring is in an uncompressed state, the first pivoting spike assembly is free to move about the fastener, and when a compression force is applied to the first pivoting spike assembly, the spring collapse upon the fastener to immobilize the first pivoting spike assembly relative to the first plate.

14. The method of claim 13, wherein the first pivoting spike assembly includes serrations and the fastener includes corresponding serrations that mesh with the serrations of the first pivoting spike assembly to immobilize the first pivoting spike assembly relative to the first plate when the compression force is applied to the first pivoting spike assembly.

15. The method of claim 10, wherein the actuator assembly comprises a front ramped actuator and a rear ramped actuator, and wherein the upper portion of the barrel comprises ramped upper sidewalls in engagement with the rear ramped actuator and the front ramped actuator, and wherein the lower portion of the barrel comprises ramped lower sidewalls in engagement with the rear ramped actuator and the front ramped actuator.

16. The method of claim 15, wherein the ramped upper sidewalls and the ramped lower sidewalls define a central opening configured to receive graft packing material.

* * * * *